(12) United States Patent
Marx et al.

(10) Patent No.: US 10,227,643 B2
(45) Date of Patent: Mar. 12, 2019

(54) MUTATED DNA POLYMERASES WITH HIGH SELECTIVITY AND ACTIVITY

(71) Applicant: Universitaet Konstanz, Constance (DE)

(72) Inventors: Andreas Marx, Constance (DE); Matthias Drum, Constance (DE); Ramon Kranaster, Constance (DE)

(73) Assignee: UNIVERSITAET KONSTANZ (DE)

( * ) Notice: Subject to any disclaimer, the term of this patent is extended or adjusted under 35 U.S.C. 154(b) by 23 days.

(21) Appl. No.: 15/100,560

(22) PCT Filed: Dec. 2, 2014

(86) PCT No.: PCT/EP2014/076208
§ 371 (c)(1),
(2) Date: May 31, 2016

(87) PCT Pub. No.: WO2015/082449
PCT Pub. Date: Jun. 11, 2015

(65) Prior Publication Data
US 2016/0298174 A1    Oct. 13, 2016

(30) Foreign Application Priority Data
Dec. 2, 2013 (LU) .......................................... 92320

(51) Int. Cl.
*C12N 9/12* (2006.01)
*C12Q 1/686* (2018.01)

(52) U.S. Cl.
CPC ........... *C12Q 1/686* (2013.01); *C12N 9/1252* (2013.01); *C12Y 207/07007* (2013.01)

(58) Field of Classification Search
CPC combination set(s) only.
See application file for complete search history.

(56) References Cited

U.S. PATENT DOCUMENTS

2011/0027833 A1    2/2011    Hogrefe

FOREIGN PATENT DOCUMENTS

| DE | 102006025154 A1 | 12/2007 |
|---|---|---|
| WO | 2007137700 A2 | 12/2007 |
| WO | 2007137701 A1 | 12/2007 |

OTHER PUBLICATIONS

Yoshida, Katushi et al., "Arg660Ser mutation in Thermus aquaticus DNA polymerase I suppresses T to C transitions: implication of wobble base pair formation at the nucleotide incorporation step", Nucleic Acids research, Oxford University Press, GB, Oct. 1, 2001. 29(20):4206-4214.

*Primary Examiner* — Kagnew H Gebreyesus
(74) *Attorney, Agent, or Firm* — Riverside Law LLP

(57) ABSTRACT

The present invention provides DNA polymerases and their use in various applications. The present invention also relates to uses and methods utilizing the DNA polymerase of the present invention for discriminating between matched and mismatched primers or detecting SNP or methylated cytosine. The present invention also relates to kits comprising such DNA polymerases.

9 Claims, 9 Drawing Sheets

Specification includes a Sequence Listing.

A　　　　　　　　Match:

Primer F20:　　　　5'-----GGAT⌐-dATP
Template F33A:　　3'-----CCTATCCA------

$k_A$

B　　　　　　　　Mismatch:

Primer F20:　　　　5'-----GGA $^T$ ⌐-dATP
Templat F33G:　　3'-----CCT $_G$ TCCA------

$k_G$

A

P —A   P —G
T —U——   T —U——

P —A   P —G
T —5mC——   T —5mC——

B

C

FIGURE 8 (cont')
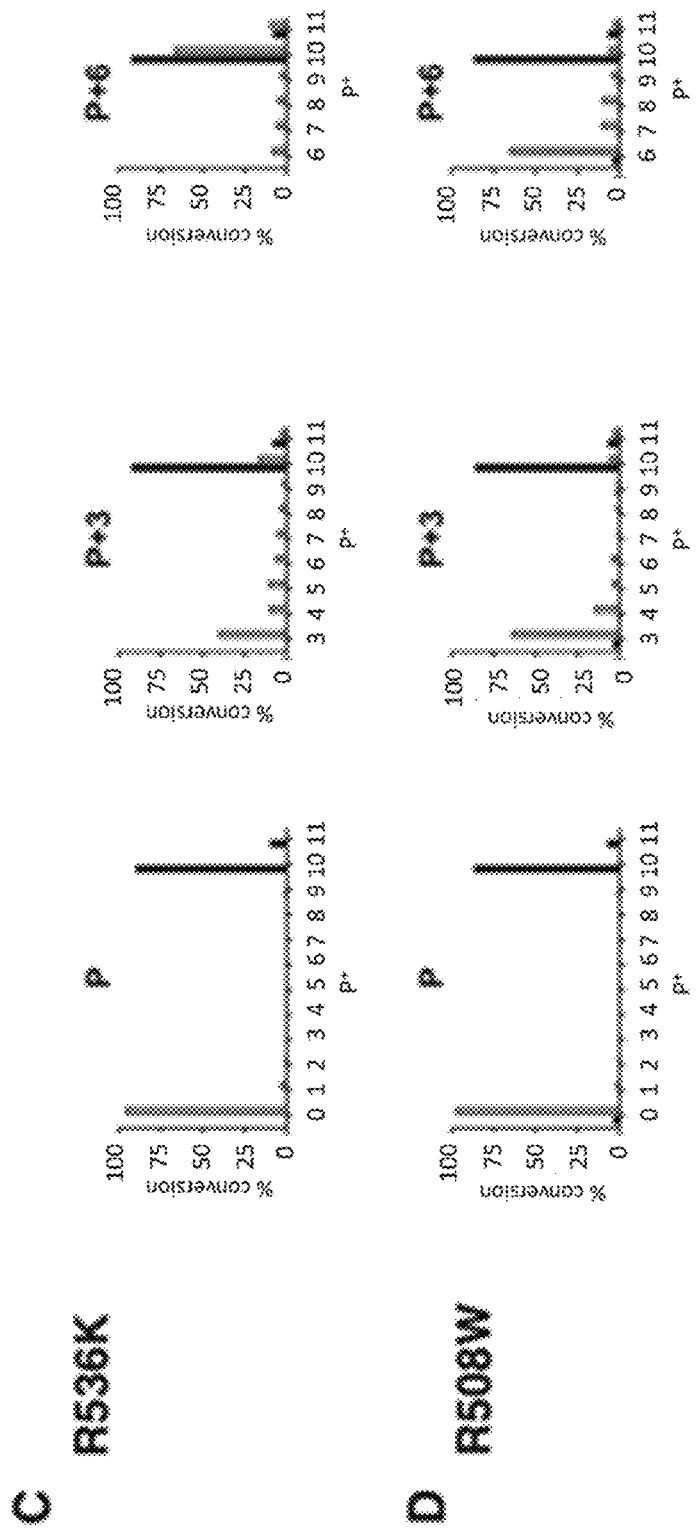

MUTATED DNA POLYMERASES WITH HIGH SELECTIVITY AND ACTIVITY

CROSS-REFERENCE TO RELATED APPLICATIONS

This application is the U.S. national phase application filed under 35 U.S.C. § 371 claiming benefit to International Patent Application No. PCT/EP2014/076208, filed on Dec. 2, 2014, which is entitled to priority to LU provisional application no. 92320, filed Dec. 2, 2013, the disclosures of which are incorporated herein by reference in their entirety.

FIELD OF THE PRESENT INVENTION

The present invention provides DNA polymerases and their use in various applications. The present invention also relates to uses and methods utilizing the DNA polymerase of the present invention for discriminating between matched and mismatched primers or detecting SNP or methylated cytosine. The present invention also relates to kits comprising such DNA polymerases.

BACKGROUND OF THE PRESENT INVENTION

Personalized medicine providing therapies, adapted to each patient's genetic predisposition (Roses 2002; Roses 2002A; Roses 2002B; Willard 2012; Lutz et al., 2011), is supported by the analysis of single nucleotide polymorphisms (SNPs) (Roses 2000). SNPs are single base variations and besides copy number variations the most abundant type of genetic variation found between members of one species (Shi 2001, Syvänen 2001; Venter et al., 2001). SNPs located in coding sequences can lead to structural and functional changes in the affected protein, enzymes or receptors. For example, the prothrombin G20210A mutation (PTM) is one of the most common genetic polymorphisms known to predispose to a first episode of venous thromboembolism (Marchiori et al., 2007). Most SNPs, however, are found in non-coding intergenic regions and often show no phenotypic effect. Intergenic SNPs present interesting markers for the determination of parentage (Hacia et al., 1999; Jorde et al., 2000), anthropology (Novembre et al., 2008; Schlebusch et al., 2012) or forensic tasks e.g. genetic fingerprinting. Many of these variations can affect predispositions for diseases or responses to drugs, chemicals and vaccines (Roses 2000; Kathiresan et al., 2009), which makes them especially interesting for pharmacogenomics (McCarthy and Hilfiker 2000; Relling and Dervieux 2001). The human genome project contributed to personalized medicine by identifying more than 2.4 million SNPs in 2001 (Lander et al., 2001; Venter et al., 2001). This created a basis for the first human haplotype map (HapMap) project with more than one million SNPs for which accurate and complete genotypes have been obtained in 269 DNA samples from four populations (International HapMap Consortium 2005). In a second step additional 2.1 million SNPs were added (Frazer et al., 2007). Phase III could further improve the quality with an extended set of 1,184 samples from 11 populations (International HapMap Consortium 2010). With the 1000 Genomes Project, a validated haplotype map of 38 million SNPs was published in 2012 (Consortium T1GP 2012). Genomes of 1,092 individuals sampled from 14 populations drawn from Europe, East Asia, sub-Saharan Africa and the Americas were analysed through a combination of low-coverage whole-genome sequence data, targeted deep exome sequence data and dense SNP genotype data (Consortium T1GP 2012).

It is most likely that SNP genotyping will be one of the future key technologies to diagnose these genetic variations between whole populations as well as in single patients. Different techniques can be used for the analysis of SNPs such as selective primer extension e.g. minisequencing (Pastinen et al., 2000; Syvänen 1999; Wartiovaara and Syvänen 2002), pyrosequencing (Ronaghi 2001) or allele specific amplification (ASA) (Myakishev et al., 2001; Pastinen et al., 2000; Shi, Bleavins and Ia iglesia 1999). Allele specific amplification (ASA) and selective primer extension (Pastinen et al., 2000) depend on the inefficient extension of a mismatched primer/template complex. Therefore highly selective DNA polymerases are urgently needed. Allele specific amplification through real-time PCR (ASA) allows detecting SNPs in a very efficient way. As unlike most other methods for SNP detection it does not require preliminary amplification of the target genetic material (Newton et al., 1989; Wu et al., 1989).

Another area of relevance is methylation-specific PCR (MSP). MSP is a widespread method used for the analysis of methylation patterns of cytosines at the C-5 position (5mC)—the most abundant DNA modification in vertebrates. 5-Methylcytosine is an important epigenetic mark and has a crucial role for activating or silencing genes (Ehrlich and Wang 1981; Jones 2012; Dawson and Kouzarides 2012). Methylation patterns alter during development and carcinogenesis (Feltus et al., 2006). Alterations of epigenetic marks like DNA methylation play a crucial role in the onset of diseases like cancer and therefore are important early stage cancer biomarkers (Dawson and Kouzarides 2012; Feltus et al., 2006, Heichmann and Warren 2012; Heyn and Esteller 2012; Deng, Liu and Du 2012). In general, it appears that the detection of epigenetic alterations is a promising and emerging tool for cancer diagnostics, prognostics, and prediction of response to therapies that awaits broad application in the future. In combination with genetic mutation analysis, epigenetic analysis will result in a very powerful approach along these lines for early diagnostics of cancer and other diseases such as neuro-developmental and metabolic disorders as well as auto-immune diseases (Heyn and Esteller 2012; Deng, Liu and Du 2012; Deng, Liu and Du 2010).

MSP, as well ASA, is a very cost-effective method that does not require specialized equipment and can be performed in almost any laboratory. Selectivity is the most important factor in ASA and MSP and can be increased by the use of modified primer probes (Strerath et al., 2002; Strerath and Marx 2005; Johnson 2004) or by the employment of mutated DNA polymerases possessing a higher mismatch extension selectivity as compared to the wild type enzyme. A selective polymerase would enable reliable ASA and MSP without the need of any substrate modifications and can thus be the most cost and work efficient solution.

Several DNA polymerases with increased DNA replication fidelity are known (Suzuki et al., 2000), e.g. for the Klenow fragment of *E. coli* DNA polymerase I and the thermostable *Thermus aquaticus* (Taq) DNA polymerase (Summerer et al., 2005) or the *Pyrococcus furiosus* (Pfu) DNA polymerase (Biles and Connolly 2004). It is known that the exchange of amino acids, affecting the interaction between polymerase and primer/template complex or the binding pocket's geometry, can lead to a change in selectivity of DNA polymerases (Kunkel and Bebenek 2000). In previous studies for instance, an increase in Taq DNA polymerase selectivity by changing the polar amino acids Q and H (Gln, and His) of motif C into two unipolar amino acids (Q to L and H to L) was achieved. Motif C is highly conserved in the palm domain within the family A, B, X and Y polymerases and plays a role in the identification of mismatched bases in the primer/template complex (Loh and Loeb 2005; Franklin, Wang and Streitz 2001). While discovered with Taq DNA polymerase, a member of family A, in further studies (Rudinger, Kranaster and Marx 2007) this concept to increase mismatch extension selectivity could be transferred to the B family Pfu DNA polymerase. The respective amino acids are found in the highly conserved motives YGDTD and KXY in eukaryotes, bacteria, archaea and viruses (Blasco et al., 1995).

Along this line, WO 2005/074350 describes DNA polymerases of the family A, with increased mismatch discrimination and therefore increased selectivity.

US2012/0258501 describes a *Thermus* sp. Z05 DNA polymerase, which can tolerate a 3' primer mismatch.

WO 2011/157435 describes DNA polymerase with increased 3' mismatch discrimination.

DE 10 2006 025 153 describes DNA polymerase with increased mismatch discrimination.

Therefore, the technical problem underlying the present invention can be seen in the provision of alternative DNA polymerases with increased mismatch discrimination. In other words, the DNA polymerases of the present invention have increased selectivity.

The technical problem is solved by the embodiments reflected in the claims, described in the description, and illustrated in the Examples and Figures.

Surprisingly, it has been found that by mutation of basic amino acids (arginine and lysine) that are in direct contact to the phosphate backbone of the primer strand in the closed conformation of the Klenow fragment of the Taq polymerase (KlenTaq) leads to the generation of DNA polymerases with advantageous properties which make the DNA polymerases of the present invention particularly suitable for, e.g. various diagnostic applications.

Specifically, the present inventors demonstrated that the selectivity of a DNA polymerase can be altered by substituting a polar amino acid residue that interacts with the backbone of the primer strand. They identified interesting mutants with increased mismatch selectivity for each examined amino acid position.

More specifically, the present inventors found that the DNA polymerase mutants described herein are suitable for diagnostic purposes, while, however, uses of the DNA polymerases described herein are not limited to diagnostic purposes. By way of example, the inventors selected the mutant (R660V) which showed best performance on genomic DNA templates to demonstrate its high mismatch selectivity. In order to further speed up detection, the inventors set-up a multiplexing assay with both allele-specific primers present in one reaction followed by an allele-identification melting curve readout. With this the SNP detection is possible in one single reaction well, as at least the presence of one allele-specific amplificate is serving as a positive control indicating both a sufficient template quality and polymerase activity. Hence, multiplexing applications are a preferred embodiment of the methods and uses of the present invention. Additionally, in particular KlenTaq R660V is able to perform ASA in the presence of whole blood sample with no previous DNA purification. This fast and easy system allows SNP genotyping in multiwell format in less than two hours with minimal costs, circumventing time and cost intensive sample preparations. However, the present invention also provides other DNA polymerase mutants that have similar or even identical properties like KlenTaq R660V. Finally they could show that the DNA polymerases described herein, in particular, KlenTaq R660V, is suitable for MSP.

The above being said, the present invention relates to a DNA polymerase, comprising an amino acid sequence comprising at one or more positions corresponding to position(s) 487, 508, 536, 587 and/or 660 of the amino acid sequence of the Taq polymerase shown in SEQ ID NO:1 or at corresponding positions of a Klenow fragment thereof, an amino acid substitution.

The present invention also relates to a DNA polymerase, comprising an amino acid sequence comprising at one or more positions corresponding to position(s) 210, 231, 259, 310 and/or 383 of the amino acid sequence of the KlenTaq polymerase shown in SEQ ID NO:2 an amino acid substitution.

Additionally, the present invention relates to the use of the DNA polymerase of the present invention, for detection of at least one SNP, which SNP is comprised in a target sequence.

The present invention further relates to the use of the DNA polymerase of the present invention, for detection of a methylation status of a target sequence.

The present invention also relates to the use of a DNA polymerase of the present invention, for discrimination between as matched and a mismatched primer, wherein said primers hybridize to a target sequence, and wherein the mismatched primer comprises a non-canonical nucleotide in a position of up to seven bases from its 3' end in relation to the target sequence to which it hybridizes.

The present invention further relates to the use of a DNA polymerase of the present invention as a diagnostic for diagnosing a disease of a subject, which disease is associated with a SNP or a methylation status of a target sequence, which target sequence is comprised in the genomic DNA of the subject.

In addition, the present invention relates to the use of a DNA polymerase of the present invention, in the presence of a dye that binds to double stranded DNA at a concentration of 10×-60× e.g., SYBRGreenI The present invention further relates to the use of a DNA polymerase of the present invention in the presence of blood.

The present invention also relates to the use of a DNA polymerase of the present invention, at a concentration of 25 nM-600 nM.

Additionally, the present invention relates to a DNA polymerase for use in in vitro diagnosis of a disease of a subject, which disease is associated with a SNP in a target sequence, which target sequence, is comprised in the genomic DNA of a subject.

Also, the present invention relates to a DNA polymerase for use in in vitro diagnosis of a disease of a subject, which disease is associated with a methylation status of a target sequence, which target sequence is comprised in the genomic DNA of a subject.

The present invention further relates to an in vitro method for detecting at least one SNP in at least one template comprising contacting the DNA polymerase of the present invention with
  i) the at least one template;
  ii) at least one matched and/or at least one mismatched primer,
    wherein said primers hybridize to the target sequence, and wherein the mismatched primer comprises a non-canonical nucleotide in a position of up to seven bases from its 3' end in relation to the target sequence to which it hybridizes; and iii) nucleoside triphosphates.

In addition, the present invention relates to an in vitro method for detecting at least one methylated nucleotide, preferably cytosine in at least one template comprising contacting the DNA polymerase of the present invention with i) the at least one template;
ii) at least one matched and/or at least one mismatched primer,
   wherein said primers hybridize to the target sequence, and
   wherein the mismatched primer comprises a non-canonical nucleotide in a position of up to seven bases from its 3' end in relation to the target sequence to which it hybridizes; and
iii) nucleoside triphosphates.

Further, the present invention relates to a nucleic acid molecule coding for a DNA polymerase of the present invention.

Also, the present invention relates to a vector comprising the nucleic acid of the present invention.

The present invention additionally relates to a host cell comprising the vector of the present invention and/or the nucleic acid of the present invention.

The present invention also relates to a kit comprising the DNA polymerase of the present invention.

Further, the present invention relates to a kit-of-parts comprising the DNA polymerase of the present invention.

DETAILED DESCRIPTION OF THE PRESENT INVENTION

Figure 1:
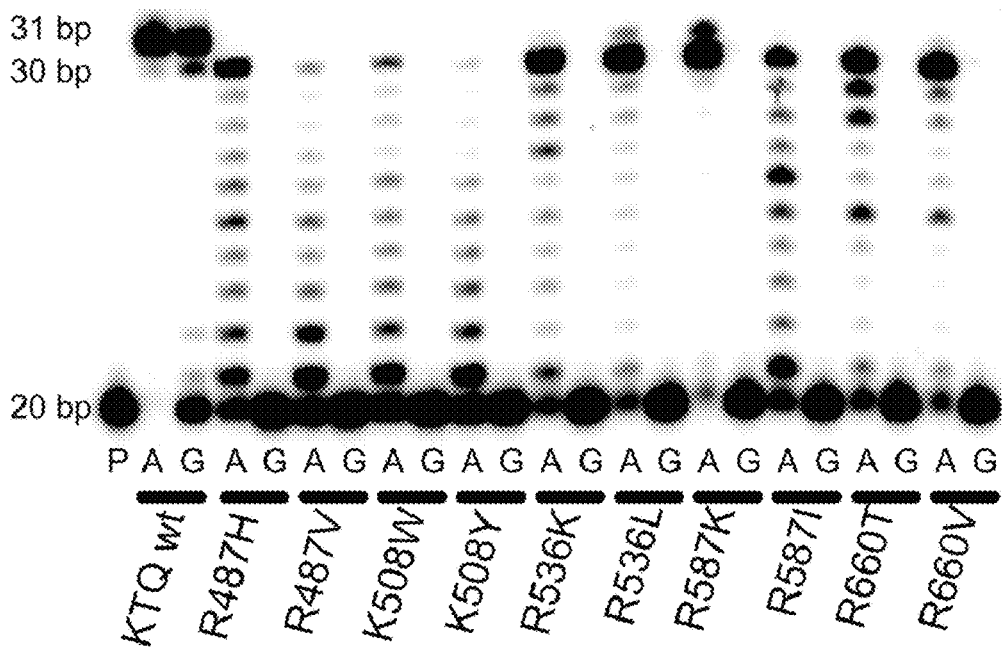
FIG. 1: Primer extension experiments with KlenTaq wt and mutants. A) Primer and Template Sequence. The radioactively labelled primer is either 3' matched or mismatched depending on the template. B) PAGE gel of primer extension. P=primer, A=match case template, G=mismatch case template. Mutants and KTQ (KlenTaq) wt as indicated.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The invention provides for a DNA polymerase, comprising an amino acid sequence comprising at one or more positions corresponding to position(s) 487, 508, 536, 587 and/or 660 of the amino acid sequence of the Taq polymerase shown in SEQ ID NO:1 or at corresponding positions of a Klenow fragment thereof, an amino acid substitution.

A "DNA polymerase" can add free nucleotides only to the 3' end of the template strand; this results in elongation of the newly forming strand in a 5'→3' direction. DNA polymerase can add a nucleotide only on to a pre-existing 3'-OH group, and, therefore, needs a primer or oligonucleotide at which it can add the first nucleotide. The directionality of the newly forming strand (the daughter strand) is opposite to the direction in which DNA polymerase moves along the template strand. The term "DNA polymerase" as used herein includes DNA polymerases that have been modified by e.g. natural process such as posttranslational processing, or non-natural process such as chemical modification. Such modifications can occur on the peptide backbone, amino acid side chains, or the N- or C-terminus. Modifications include e.g. acetylations, acylations, ADP-ribosylations, amidations, covalent attachment of flavines, haem-groups, nucleotides or nucleotide derivatives, lipids or lipid derivatives, cyclizations, disulfide bridges, methylations and demethylations, cystine linkages, formylations, γ-carboxylations, glycosylations, hydroxylations, phosphorylations and the tRNA-mediated addition of amino acids.

A polymerase can generally experimentally be analyzed by two types of reactions, first the steady state kinetic measurements and second the pre-steady state kinetic methods. The steady state measurements give an impression on the kinetic parameter $K_M$ (Michealis-Menten constant) and $V_{max}$ or $K_{cat}$ (maximal velocity of reaction; $k_{cat}=V_{max}/c$ (enzyme)). This reaction is generating a mean over the whole reaction from binding of the primer/template or target sequence complex to the implementation of the nucleotide. This reaction has to be taking place under single completed hit conditions, so that every primer/template complex is maximally hit one time by the DNA polymerase so that the generated data only mirror the conversion mediated by the DNA polymerase and not the conversion mediated by many DNA polymerases on one template. In real experiments this objective is achieved by mixing a template in excess in relation to the enzyme and a maximal implementation rate of 20% of the primers (Creighton, Bloom and Goodman 1995; Boosalis, Petruska and Goodman 1987). In the pre-steady state kinetic methods (stopped flow or quench flow) single turnover conditions are generated so that the influence of association and dissociation does not affect the kinetic parameters. Here an excess of the enzyme in relation to the substrate are mixed, such that every primer/template or target sequence complex is occupied with a polymerase. Then the reaction is initiated by the addition of dNTPs and stopped within a short period of time (rapid quench flow) or is monitored during the course of the reaction via fluorescence methods (stopped flow). In this way the kinetic parameters of the affinity of the dNTP to the polymerase-DNA complex (KD) and the maximal implementation rate (kpol) can be determined (Johnson 1993; Bryant, Johnson and Benkovic 1983).

In one embodiment, the DNA polymerase of the present invention has an amino acid sequence of any of SEQ ID NO: 3-24.

The term "Taq polymerase" or "Taq" as used herein, is a thermostable DNA polymerase named after the thermophilic bacterium *Thermus aquaticus* from which it was originally isolated (Chien, Edgar and Trela 1976). *T. aquaticus* is a bacterium that lives in hot springs and hydrothermal vents, and Taq polymerase was identified as an enzyme able to withstand the protein-denaturing conditions (high temperature) required during PCR (Chien, Edgar and Trela 1976). Taq's optimum temperature for activity is 75-80° C., with a half-life of greater than 2 hours at 92.5° C., 40 minutes at 95° C. and 9 minutes at 97.5° C., and can replicate a 1000 base pair strand of DNA in less than 10 seconds at 72° C. (Lawyer et al., 1993). It lacks a 3'→5' exonuclease proofreading activity (Lawyer et al., 1993) and has an error rate measured at about 1 in 9,000 nucleotides (Tindall and Kunkel 1988). Use of the thermostable Taq for example enables running the PCR at high temperature (~60° C. and above) (Saiki et al., 1988). The amino acid sequence shown in SEQ ID NO: 1 in the context of Taq polymerase serves as reference sequence.

In another embodiment, the DNA polymerase (Taq) of the present invention has an amino acid sequence of any of SEQ ID NO: 3-13.

In another embodiment the DNA polymerase (Taq) of the present invention has an amino acid sequence of SEQ ID NO: 3.

In another embodiment the DNA polymerase (Taq) of the present invention has an amino acid sequence of SEQ ID NO: 4.

In yet another embodiment the DNA polymerase (Taq) of the present invention has an amino acid sequence of SEQ ID NO: 5.

In a further embodiment the DNA polymerase (Taq) of the present invention has an amino acid sequence of SEQ ID NO: 6.

In another embodiment the DNA polymerase (Taq) of the present invention has an amino acid sequence of SEQ ID NO: 7.

In yet another embodiment the DNA polymerase (Taq) of the present invention has an amino acid sequence of SEQ ID NO: 8.

In a further embodiment the DNA polymerase (Taq) of the present invention has an amino acid sequence of SEQ ID NO: 9.

In another embodiment the DNA polymerase (Taq) of the present invention has an amino acid sequence of SEQ ID NO: 10.

In yet another embodiment the DNA polymerase (Taq) of the present invention has an amino acid sequence of SEQ ID NO: 11.

In yet another embodiment the DNA polymerase (Taq) of the present invention has an amino acid sequence of SEQ ID NO: 12.

In a further embodiment the DNA polymerase (Taq) of the present invention has an amino acid sequence of SEQ ID NO: 13.

A "Klenow fragment thereof" as used herein is any C-terminal fragment of a DNA polymerase that retains its polymerase activity. In addition, it retains the 3'→5' exonuclease activity for removal of preceeding nucleotides and proofreading, but loses its 5'→3' exonuclease activity. However, the present invention embraces also Klenow fragments derived from a DNA polymerase such as the Taq polymerase, wherein the 5'→3' exonuclease activity was removed by e.g. removal of a small amino-terminal region of the polymerase. The 5'→3' exonuclease activity can also be greatly reduced in a Klenow fragment of the present invention.

In one embodiment of the present invention, the Klenow fragment is obtained from the Taq polymerase, preferably the Klenow fragent of the Taq polymerase is a Klen Taq e.g. a Klen Taq of SEQ ID NO: 2. Thus in one embodiment, the Klenow fragment of the Taq polymerase is the KlenTaq shown in SEQ ID NO: 2. Accordingly, the amino acid sequence shown in SEQ ID NO:2 serves as reference sequence.

A "Klen Taq" or "KTQ" polymerase as used herein is a Taq polymerase lacking the 5'→3' exonuclease function. As the Klen Taq per se does not comprise a 3'→5' exonuclease function it comprises its polymerase function. The KlenTaq overts a higher (about twice) thermostability and lower (about half; $5 \times 10^{-5}$) error rate than the Taq (Villbrandt, Sagner and Schomburg, 1997; Barnes 1992; Lawyer et al. 1993).

The invention further relates to a DNA polymerase, comprising an amino acid sequence comprising at one or more positions corresponding to position(s) 210, 231, 259, 310 and/or 383 of the amino acid sequence of the KlenTaq polymerase shown in SEQ ID NO:2 an amino acid substitution.

In one embodiment, the DNA polymerase (KlenTaq) of the present invention has an amino acid sequence of any of SEQ ID NO: 14-24.

In another embodiment the DNA polymerase (KlenTaq) of the present invention has an amino acid sequence of SEQ ID NO: 14.

In another embodiment the DNA polymerase (KlenTaq) of the present invention has an amino acid sequence of SEQ ID NO: 15.

In yet another embodiment the DNA polymerase (KlenTaq) of the present invention has an amino acid sequence of SEQ ID NO: 16.

In a further embodiment the DNA polymerase (KlenTaq) of the present invention has an amino acid sequence of SEQ ID NO: 17.

In another embodiment the DNA polymerase (KlenTaq) of the present invention has an amino acid sequence of SEQ ID NO: 18.

In yet another embodiment the DNA polymerase (KlenTaq) of the present invention has an amino acid sequence of SEQ ID NO: 19.

In a further embodiment the DNA polymerase (KlenTaq) of the present invention has an amino acid sequence of SEQ ID NO: 20.

In another embodiment the DNA polymerase (KlenTaq) of the present invention has an amino acid sequence of SEQ ID NO: 21.

In yet another embodiment the DNA polymerase (KlenTaq) of the present invention has an amino acid sequence of SEQ ID NO: 22.

In a further embodiment the DNA polymerase (KlenTaq) of the present invention has an amino acid sequence of SEQ ID NO: 23.

In another embodiment the DNA polymerase (KlenTaq) of the present invention has an amino acid sequence of SEQ ID NO: 24.

In one embodiment, the DNA polymerase of the present invention comprises an amino acid substitution, wherein one or more of the amino acids are substituted with a basic, polar and uncharged or hydrophobic amino acid.

An "amino acid" refers to any monomer unit that can be incorporated into a peptide, polypeptide, or protein. As used herein, the term "amino acid" includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). The structures of these twenty natural amino acids are shown in, e.g., Stryer et al., *Biochemistry.* $5^{th}$ ed., Freeman and Company (2002). Additional amino acids, such as selenocysteine and pyrrolysine, can also be genetically coded for (Stadtman (1996) "Selenocysteine," *Annu Rev Biochem.* 65:83-100 and Ibba et al. (2002) "Genetic code: introducing pyrrolysine," *Curr Biol.* 12(13):R464-R466). The term "amino acid" also includes unnatural amino acids, modified amino acids (e.g., having modified side chains and/or backbones), and amino acid analogs. An amino acid is typically an organic acid that includes a substituted or unsubstituted amino group, a substituted or unsubstituted carboxy group, and one or more side chains or groups, or analogs of any of these groups. Exemplary side chains include, e.g., thiol, seleno, sulfonyl, alkyl, aryl, acyl, keto, azido, hydroxyl, hydrazine, cyano, halo, hydrazide, alkenyl, alkynl, ether, borate, boronate, phospho, phosphono, phosphine, heterocyclic, enone, imine, aldehyde, ester, thioacid, hydroxylamine, or any combination of these groups. Other representative amino acids include, but are not limited to, amino acids comprising photoactivatable cross-linkers, metal binding amino acids, spin-labeled amino acids, fluorescent amino acids, metal-containing amino acids, amino acids with novel functional groups, amino acids that covalently or noncovalently interact with other molecules, photocaged and/or photoisomerizable amino acids, radioactive amino acids, amino acids comprising biotin or a biotin analog, glycosylated amino acids, other carbohydrate modified amino acids, amino acids comprising polyethylene glycol or polyether, heavy atom substituted amino acids, chemically cleavable and/or photocleavable amino acids, carbon-linked sugar-containing amino acids, redox-active amino acids, amino thioacid containing amino acids, and amino acids comprising one or more toxic moieties.

An "amino acid substitution" means a replacement of an amino acid relative to a corresponding naturally-occurring or unmodified DNA polymerase. In one embodiment, the replacement is an amino acid substitution of an amino acid relative to a polymerase of SEQ ID NO: 1. In another embodiment, the replacement is an amino acid substitution of an amino acid relative to a polymerase of SEQ ID NO: 2.

A "basic amino acid" has basic side chains at neutral pH. Their pKa's are high enough that they tend to bind protons, gaining a positive charge in the process. Examples include histidine, lysine and arginine. In one embodiment, the basic amino acid of the present invention is histidine. In one embodiment, the basic amino acid of the present invention is arginine or lysine. In another embodiment, the basic amino acid of the present invention is arginine. In yet another embodiment the basic amino acid of the present invention is lysine.

Thus, in one embodiment, the substitution with a basic amino acid is from Arg to His or Lys or from Lys to His or Arg.

In another embodiment, the substitution with a basic amino acid is from Arg to His or Lys.

In another embodiment, the substitution with a basic amino acid is from Lys to His or Arg.

In one embodiment, the substitution with a basic amino acid is from R (Arg) to H (His).

In another embodiment, the substitution with a basic amino acid is from R (Arg) to K (Lys).

A "polar and uncharged amino acid" can have side chains of a spectrum of functional groups. However, most have at least one atom (nitrogen, oxygen, or sulfur) with electron pairs available for hydrogen bonding to water and other molecules except for glycine. Examples of polar and uncharged amino acids are glycine, serine, cysteine, threonine, tyrosine, asparagine, and glutamine. In one embodiment, the polar and uncharged amino acid is selected from threonine and tyrosine. In another embodiment, the polar and uncharged amino acid of the present invention is threonine. In yet another embodiment, the polar and uncharged amino acid of the present invention is tyrosine.

Thus, in one embodiment, the substitution with a polar and uncharged amino acid is from R (Arg) or Lys (K) to glycine, serine, cysteine, threonine, tyrosine, asparagine or glutamine.

In another embodiment, the substitution with a polar and uncharged amino acid is from R (Arg) or Lys (K) to threonine or tyrosine.

In another embodiment, the substitution with a polar and uncharged amino acid is from R (Arg) to T (Thr).

In another embodiment, the substitution with a polar and uncharged amino acid is from Lys (K) to T (Thr) or Y (Tyr).

In one embodiment, the substitution with a polar and uncharged amino acid is from Lys (K) to T (Thr).

In another embodiment, the substitution with a polar and uncharged amino acid is from Lys (K) to Y (Tyr).

A "hydrophobic amino acid" has a side chain that is composed mostly of carbon and hydrogen, have very small dipole moments, and tend to be repelled from water. Examples include alanine, valine, leucine, isoleucine, proline, phenylalanine, tryptophan, cysteine, tyrosine, histidine, threonine, serine and methionine. In one embodiment, the hydrophobic amino acid is selected from the group consisting of valine, leucine, isoleucine, threonine, tyrosine, histidine or tryptophan. In one embodiment, the hydrophobic amino acid is a more hydrophobic amino acid.

In one embodiment, the hydrophobic amino acid is valine. In another embodiment, the hydrophobic amino acid of the present invention is leucine. In yet another embodiment the hydrophobic amino acid is isoleucine. In a further embodiment the hydrophobic amino acid is tryptophan. In a further embodiment the hydrophobic amino acid is histidine. In a further embodiment the hydrophobic amino acid is tyrosine. In a further embodiment the hydrophobic amino acid is threonine.

Hydrophobicity scales are values that define relative hydrophobicity of amino acid residues. The more positive the value, the more hydrophobic are the amino acids located in that region of the protein. The most common method of measuring amino acid hydrophobicity is partitioning between two immiscible liquid phases. Nozaki and Tanford proposed a hydrophobicity scale for nine amino acids (Nozaki and Tanford, 1971). Two scales have been developed using micellar phases (Fendler, Nome and Nagyvary 1975; Leodidas and Hatton 1990). Also, amino acid side chain affinity for water can be measured using vapor phases (Wolfenden, Andersson and Cullis, 1981).

Hydrophobicity scales can also be obtained by calculating the solvent accessible surface areas for amino acid residues in the expended polypeptide chain (Chothia 1976) or in alpha-helix and multiplying the surface areas by the empirical solvation parameters for the corresponding types of atoms (Kallol et al., 2003). A differential solvent accessible surface area hydrophobicity scale based on proteins as compacted networks near a critical point, due to self-organization by evolution, was constructed based on asymptotic power-law (self-similar) behavior (Moret and Zebende, 2007; Phillips 2009). This scale is based on a bioinformatic survey of 5526 high-resolution structures from the Protein Data Bank. Reversed phase liquid chromatography (RPLC) is a chromatographic method for measuring solute hydrophobicity (Kallol et al., 2003; Hodges et al., 1994).

Another hydrophilicity scale, which used normal phase liquid chromatography and showed the retention of 121 peptides on an amide-80 column, is also available (Plass, Valko and Abraham 1998). The absolute values and relative rankings of hydrophobicity determined by chromatographic methods can be affected by a number of parameters. These parameters include the silica surface area and pore diameter, the choice and pH of aqueous buffer, temperature and the bonding density of stationary phase chains (Kallol et al., 2003).

In another embodiment, the DNA polymerase, of the present invention comprises an amino acid substitution, wherein one or more of the amino acids are substituted with a more hydrophobic amino acid.

The term "more hydrophobic amino acid" is a substitution of an amino acid with an amino acid of greater hydrophobicity. Hydrophobicity, however, is a relative expression, as also described above. The skilled artesian knows how to measure hydrophobicity and also knows that it can change due to e.g. the pH. A rude classification is given in the table below:

TABLE

| Hydrophobicity | |
| --- | --- |
| High hydrophobicity | Val, Ile, Leu, Met, Phe, Trp, Cys |
| Median hydrophobicity | Ala, Tyr, His, Thr, Ser, Pro, Gly |
| Low hydrophobicity | Arg, Asp, Lys, Glu |

In one embodiment, the substitution with a more hydrophobic amino acid is from Arg or Lys to His, Ala, Tyr, Thr, Ser, Pro, Gly, Val, Ile, Leu, Met, Phe, Trp or Cys.

In one embodiment, the substitution with a more hydrophobic amino acid is from Arg to His, Ala, Tyr, Thr, Ser, Pro, Gly, Val, Ile, Leu, Met, Phe, Trp or Cys.

In another embodiment, the substitution with a more hydrophobic amino acid is from Lys to His, Ala, Tyr, Thr, Ser, Pro, Gly, Val, Ile, Leu, Met, Phe, Trp or Cys.

In one embodiment, the substitution with a more hydrophobic amino acid is from R (Arg) to H (His), V (Val), L (Leu), I (Ile) or T (Thr) or from K (Lys) to W (Trp) or Y (Tyr).

In one embodiment, the substitution with a more hydrophobic amino acid is from R (Arg) to H (His), V (Val), L (Leu), I (Ile) or T (Thr).

In one embodiment, the substitution with a more hydrophobic amino acid is from R (Arg) to H (His).

In another embodiment, the substitution with a more hydrophobic amino acid is from R (Arg) to V (Val).

In a further embodiment, the substitution with a more hydrophobic amino acid is from R (Arg) to L (Leu).

In another embodiment, the substitution with a more hydrophobic amino acid is from R (Arg) to I (Ile).

In a further embodiment, the substitution with a more hydrophobic amino acid is from R (Arg) to T (Thr).

In another embodiment, the substitution with a more hydrophobic amino acid is from K (Lys) to W (Trp) or Y (Tyr).

In still another embodiment, the substitution with a more hydrophobic amino acid is from K (Lys) to W (Trp).

In a further embodiment, the substitution with a more hydrophobic amino acid is from K (Lys) to Y (Tyr).

The term "mutant," in the context of DNA polymerases of the present invention, means a polypeptide, typically recombinant, that comprises one or more amino acid substitutions relative to a corresponding, naturally-occurring or unmodified DNA polymerase. In one embodiment, the one or more substitution is present relative to a DNA polymerase of SEQ ID NO: 1. In another embodiment, the one or more substitution is present relative to a DNA polymerase of SEQ ID NO: 2. The mutant can have a sequence of any of SEQ ID NO: 3-24. A mutation can be introduced in the desired position by techniques known to the skilled in the art. For example a skilled artesian, when starting from a protein of SEQ ID NO: 2 willing to introduce an amino acid substitution at position number 210, will first analyze, which nucleotide triplet encodes for this amino acid. One approach would include e.g. site-directed mutagenesis, for mutation of the triplet code, so that it encodes for another amino acid than the one present in the wildtype polymerase. Site-directed mutagenesis is a molecular biology method that is used to make specific and intentional changes to the DNA sequence of a gene and any gene products (Cormack B. (1994) Introduction of a point mutation by sequential PCR steps. Curr. Protoc. Mol. Biol., 2, 8.5.7-8.5.9; Aiyar A., Xiang, Y. and Leis, J. (1996) Site-directed mutagenesis using overlap extension PCR. Methods Mol. Biol., 57, 177-191; Ishii T. M., Zerr, P., Xia, X. M., Bond, C. T., Maylie, J. and Adelman, J. P. (1998) Site-directed mutagenesis. Methods Enzymol., 293, 53-71; Ling M. M. and Robinson, B. H. (1997) Approaches to DNA mutagenesis: an overview. Anal. Biochem., 254, 157-178). The altered nucleotide sequence can then be expressed in a host cell e.g. *E. coli*. The desired protein can then be obtained and/or purified. In one embodiment the one or more substitutions are present relative to a DNA polymerase of SEQ ID NO: 1. In another embodiment, the one or more substitutions are present relative to a DNA polymerase of SEQ ID NO: 2.

When used herein, the term "polypeptide" or "protein" (both terms are used interchangeably herein) means a peptide, a protein, or a polypeptide which encompasses amino acid chains of a given length, wherein the amino acid residues are linked by covalent peptide bonds. However, peptidomimetics of such proteins/polypeptides wherein amino acid(s) and/or peptide bond(s) have been replaced by functional analogs are also encompassed by the invention as well as other than the 20 gene-encoded amino acids, such as selenocysteine. Peptides, oligopeptides and proteins may be termed polypeptides. The terms polypeptide and protein are often used interchangeably herein. The term polypeptide also refers to, and does not exclude, modifications of the polypeptide, e.g., glycosylation, acetylation, phosphorylation and the like. Such modifications are well described in basic texts and in more detailed monographs, as well as in the research literature.

In one embodiment, the DNA polymerase of the present invention has an amino acid sequence of any of SEQ ID NO: 3-24. In another embodiment, the DNA polymerase of the present invention has an amino acid sequence of any of SEQ ID NO: 3-13. In yet another embodiment, the DNA polymerase of the present invention has an amino acid sequence of any of SEQ ID NO: 14-24. In another embodiment, the DNA polymerase of the present invention has an amino acid sequence of any of SEQ ID NO: 3-12. In another embodiment, the DNA polymerase of the present invention has an amino acid sequence of any of SEQ ID NO: 14-23.

The term "position" when used in accordance with the present invention means the position of an amino acid within an amino acid sequence depicted herein. The term "corresponding" as used herein also includes that a position is not only determined by the number of the preceding amino acids. The position of a given amino acid in accordance with the present invention which may be substituted may vary due to deletions or additional nucleotides elsewhere in a (mutant or wild-type) polymerase-untranslated region (UTR) including the promoter and/or any other regulatory sequences or gene (including exons and introns). Similarly, the position of a given amino acid in accordance with the present invention which may be substituted may vary due to deletion or addition of amino acids elsewhere in a (mutant or wild-type) polymerase polypeptide.

Thus, under a "corresponding position" in accordance with the present invention it is preferably to be understood that amino acids may differ in the indicated number but may still have similar neighboring amino acids. Said amino acids which may be exchanged, deleted or added are also comprised by the term "corresponding position". Specifically, the skilled person may, when aligning the reference sequence (subject sequence) for example SEQ ID No:1 or 2, preferably SEQ ID NO: 1 with an amino acid sequence of interest (query sequence), for example, inspect a sequence of interest for the sequence of SEQ ID NO: 1 (or the corresponding amino acid sequence encoding this protein, respectively) when looking for the amino acid position as specified herein (i.e., a position corresponding to position 487 and/or 508 of the amino acid sequence shown in SEQ ID No: 1.

More specifically, the amino acid "R" or "K" respectively of said position is subject to substitution. Said "R" or "K" is then replaced in a by another amino acid. In one embodiment, the "R" of said position is substituted by an amino acid other than "R". In another embodiment, the "K" of said position is substituted by an amino acid other than "K".

In order to determine whether an amino acid residue in a given (mutant or wild-type) polymerase amino acid sequence corresponds to a certain position in the amino acid sequence of SEQ ID No: 1 or the amino acid sequence of SEQ ID No: 2, preferably SEQ ID NO: 1, the skilled person can use means and methods well-known in the art, e.g., alignments, either manually or by using computer programs such as BLAST2.0, which stands for Basic Local Alignment Search Tool or ClustalW or any other suitable program which is suitable to generate sequence alignments.

In one embodiment the DNA polymerase of the present invention has at least 80%, preferably 90%, more preferably 95%, even more preferred 99%, and still more preferred 100% identity to the Taq polymerase shown in SEQ ID NO:1 or its Klenow fragment KlenTaq shown in SEQ ID NO: 2.

"Percent (%) nucleotide sequence identity" with respect to (mutant or wild-type) polymerase amino acid sequences identified herein is defined as the percentage of amino acids in a candidate sequence (sequence of interest) that are identical with the amino acids in the polymerase protein sequence shown in SEQ ID No:1 or the amino acid sequences shown in SEQ ID NO: 2 after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared. The degree of identity is preferably over the entire length with the amino acid sequence of SEQ ID NO: 1 or 2. For example, an amino acid sequence of interest is aligned with amino acid sequence of SEQ ID No: 1 or 2 and the identical amino acid residues are determined.

In order to determine whether an amino acid sequence has a certain degree of identity to the amino acid sequence encoding a (mutant or wild-type) polymerase protein of the present invention, the skilled person can use means and methods well-known in the art, e.g., alignments, either manually or by using computer programs such as those mentioned further down below in connection with the definition of the term "hybridization" and degrees of homology.

For example, BLAST2.0, which stands for Basic Local Alignment Search Tool (Altschul, Nucl. Acids Res. 25 (1997), 3389-3402; Altschul, J. Mol. Evol. 36 (1993), 290-300; Altschul, J. Mol. Biol. 215 (1990), 403-410), can be used to search for local sequence alignments. BLAST produces alignments of both nucleotide and amino acid sequences to determine sequence similarity. Because of the local nature of the alignments, BLAST is especially useful in determining exact matches or in identifying similar sequences. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

Analogous computer techniques using BLAST (Altschul (1997), cited herein; Altschul (1993), cited herein; Altschul (1990), cited herein) are used to search for identical or related molecules in nucleotide databases such as GenBank or EMBL. This analysis is much faster than multiple membrane-based hybridizations. In addition, the sensitivity of the computer search can be modified to determine whether any particular match is categorized as exact or similar. The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1-2% error; and at 70, the match will be exact. Similar molecules are usually identified by selecting those which show product scores between 15 and 40, although lower scores may identify related molecules.

Along this line, in one embodiment, the DNA polymerase of the present invention comprises one or more amino acid substitutions with regard to the amino acid sequence shown in SEQ ID NO: 1 selected from the group consisting of R487H/V, K508W/Y, R536K/L, R587K/I, R660T/V. In another embodiment, the DNA polymerase of the present invention comprises one or more amino acid substitutions selected from the group consisting of R536K/L, R587K/I, R660T/V. Here, the number identifies the position of the amino acid in regard to SEQ ID NO: 1. By the description of an amino acid substitution being e.g. R487H/V it is meant that at position 487 the substitution is from R to H or from R to V at position 487 with regard to SEQ ID NO: 1. Similarly, an amino acid substitution such as K508W/Y includes an amino acid substitution from K to W or from K to Y at position 508 with regard to SEQ ID NO: 1.

In one embodiment, one substitution is selected from the group consisting of R487H, K508W, R536K, R587I, R660T, R487V, K508Y, R536L, R587I or R660V.

In one embodiment, one substitution is selected from the group consisting of R536K, R587K, R660V, R536L, R587I or R660V.

In one embodiment, the DNA polymerase of the present invention comprises one or more amino acid substitutions with regard to the amino acid sequence shown in SEQ ID NO: 1, wherein one amino acid substitution is R487H.

In another embodiment, the DNA polymerase of the present invention comprises one or more amino acid substitutions with regard to the amino acid sequence shown in SEQ ID NO: 1, wherein one amino acid substitution is R487V.

In yet another embodiment, the DNA polymerase of the present invention comprises one or more amino acid substitutions with regard to the amino acid sequence shown in SEQ ID NO: 1, wherein one amino acid substitution is K508W.

In a further embodiment, the DNA polymerase of the present invention comprises one or more amino acid substitutions with regard to the amino acid sequence shown in SEQ ID NO: 1, wherein one amino acid substitution is K508Y.

In another embodiment, the DNA polymerase of the present invention comprises one or more amino acid substitutions with regard to the amino acid sequence shown in SEQ ID NO: 1, wherein one amino acid substitution is R536K.

In yet another embodiment, the DNA polymerase of the present invention comprises one or more amino acid substitutions with regard to the amino acid sequence shown in SEQ ID NO: 1, wherein one amino acid substitution is R536L.

In a further embodiment, the DNA polymerase of the present invention comprises one or more amino acid substitutions with regard to the amino acid sequence shown in SEQ ID NO: 1, wherein one amino acid substitution is R587K.

In a another embodiment, the DNA polymerase of the present invention comprises one or more amino acid substitutions with regard to the amino acid sequence shown in SEQ ID NO: 1, wherein one amino acid substitution is R587I.

In another embodiment, the DNA polymerase of the present invention comprises one or more amino acid substitutions with regard to the amino acid sequence shown in SEQ ID NO: 1, wherein one amino acid substitution is R660T.

In yet another embodiment, the DNA polymerase of the present invention comprises one or more amino acid substitutions with regard to the amino acid sequence shown in SEQ ID NO: 1, wherein one amino acid substitution is R660V.

Also, in another embodiment, the DNA polymerase of the present invention comprises one or more amino acid substitutions with regard to the amino acid sequence shown in SEQ ID NO: 2 from the group consisting of R210H/V, K231W/Y, R259K/L, R310K/I, R383T/V. Here, the number identifies the position of the amino acid in regard to SEQ ID NO: 2. By the description of an amino acid substitution being e.g. R210H/V it is meant that at position 210 the substitution is from R to H or from R to V at position 210 with regard to SEQ ID NO: 2. Similarly, an amino acid substitution such as K231W/Y includes an amino acid substitution from K to W or from K to Y at position 231 with regard to SEQ ID NO: 2.

In one embodiment, one substitution is selected from the group consisting of R210H, K231W, R259K, R310K, R383T, R210V, K231Y, R259L, R310I or R383V.

In another embodiment, the DNA polymerase of the present invention comprises one or more amino acid substitutions from the group consisting of R259K/L, R310K/I, R383T/V.

In one embodiment one substitution is selected from the group consisting of R259K, R310K, R383T/V R259K, R310I or R383V.

In one embodiment, the DNA polymerase of the present invention comprises one or more amino acid substitutions with regard to the amino acid sequence shown in SEQ ID NO: 2, wherein one amino acid substitution is R210H.

In another embodiment, the DNA polymerase of the present invention comprises one or more amino acid substitutions with regard to the amino acid sequence shown in SEQ ID NO: 2, wherein one amino acid substitution is R210V.

In yet another embodiment, the DNA polymerase of the present invention comprises one or more amino acid substitutions with regard to the amino acid sequence shown in SEQ ID NO: 2, wherein one amino acid substitution is K231W.

In a further embodiment, the DNA polymerase of the present invention comprises one or more amino acid substitutions with regard to the amino acid sequence shown in SEQ ID NO: 2, wherein one amino acid substitution is K231Y.

In another embodiment, the DNA polymerase of the present invention comprises one or more amino acid substitutions with regard to the amino acid sequence shown in SEQ ID NO: 2, wherein one amino acid substitution is R259K.

In yet another embodiment, the DNA polymerase of the present invention comprises one or more amino acid substitutions with regard to the amino acid sequence shown in SEQ ID NO: 2, wherein one amino acid substitution is R259L.

In a further embodiment, the DNA polymerase of the present invention comprises one or more amino acid substitutions with regard to the amino acid sequence shown in SEQ ID NO: 2, wherein one amino acid substitution is R310K.

In a another embodiment, the DNA polymerase of the present invention comprises one or more amino acid substitutions with regard to the amino acid sequence shown in SEQ ID NO: 2, wherein one amino acid substitution is R310I.

In another embodiment, the DNA polymerase of the present invention comprises one or more amino acid substitutions with regard to the amino acid sequence shown in SEQ ID NO: 2, wherein one amino acid substitution is R383T.

In yet another embodiment, the DNA polymerase of the present invention comprises one or more amino acid substitutions with regard to the amino acid sequence shown in SEQ ID NO: 2, wherein one amino acid substitution is R383V.

The DNA polymerase of the present invention comprises one or more amino acid substitutions with regard to the amino acid sequence shown in SEQ ID NO: 1 or SEQ ID NO: 2. In another embodiment, the DNA polymerase comprises 2, 3, 4, 5, 6, 7, 8, 9, 10, 11, 12, 13, 14, 15, 16, 17, 18, 19, 20 or more amino acid substitutions with regard to the amino acid sequence shown in SEQ ID NO: 1 or SEQ ID NO: 2. In one embodiment, the DNA polymerase comprises 1 amino acid substitution with regard to the amino acid sequence shown in SEQ ID NO: 1 or SEQ ID NO: 2.

NO: 2. In one embodiment, the DNA polymerase comprises 2 amino acid substitution with regard to the amino acid sequence shown in SEQ ID NO: 1 or SEQ ID NO: 2.

In another embodiment, the DNA polymerase comprises 3 amino acid substitutions with regard to the amino acid sequence shown in SEQ ID NO: 1 or SEQ ID NO: 2.

In yet another embodiment, the DNA polymerase comprises 4 amino acid substitutions with regard to the amino acid sequence shown in SEQ ID NO: 1 or SEQ ID NO: 2.

In a further embodiment, the DNA polymerase comprises 5 amino acid substitutions with regard to the amino acid sequence shown in SEQ ID NO: 1 or SEQ ID NO: 2.

In another embodiment, the DNA polymerase comprises 6 amino acid substitutions with regard to the amino acid sequence shown in SEQ ID NO: 1 or SEQ ID NO: 2.

In yet another embodiment the DNA polymerase comprises 7 amino acid substitutions with regard to the amino acid sequence shown in SEQ ID NO: 1 or SEQ ID NO: 2.

In a further embodiment, the DNA polymerase comprises 8 amino acid substitutions with regard to the amino acid sequence shown in SEQ ID NO: 1 or SEQ ID NO: 2.

In another embodiment, the DNA polymerase comprises 9 amino acid substitutions with regard to the amino acid sequence shown in SEQ ID NO: 1 or SEQ ID NO: 2.

In yet another embodiment, the DNA polymerase comprises 10 amino acid substitutions with regard to the amino acid sequence shown in SEQ ID NO: 1 or SEQ ID NO: 2.

In a further embodiment, the DNA polymerase comprises 15 amino acid substitutions with regard to the amino acid sequence shown in SEQ ID NO: 1 or SEQ ID NO: 2.

In a further embodiment, the DNA polymerase comprises 20 amino acid substitutions with regard to the amino acid sequence shown in SEQ ID NO: 1 or SEQ ID NO: 2.

In one embodiment, the one or more amino acid substitutions are present with regard to the amino acid sequence shown in SEQ ID NO: 1. In another embodiment, the one or more amino acid substitutions are present with regard to the amino acid sequence shown in SEQ ID NO: 2.

The term "nucleoside triphosphate" refers to a "nucleic acid base", or "nucleotide" or "base" including modification, derivations, or analogues of conventional bases, nucleosides, or nucleotides that naturally occur in a particular polynucleotide. Certain unconventional nucleotides are modified at the 2' position of the ribose sugar in comparison to conventional dNTPs. Thus, although for RNA the naturally occurring nucleotides are ribonucleotides (i.e., ATP, GTP, CTP, UTP, collectively rNTPs), because these nucleotides have a hydroxyl group at the 2' position of the sugar, which, by comparison is absent in dNTPs, as used herein, ribonucleotides are unconventional nucleotides as substrates for DNA polymerases. As used herein, nonconventional nucleotides include, but are not limited to, compounds used as terminators for nucleic acid sequencing. Exemplary terminator compounds include but are not limited to those compounds that have a 2',3' dideoxy structure and are referred to as dideoxynucleoside triphosphates. The dideoxynucleoside triphosphates ddATP, ddTTP, ddCTP and ddGTP are referred to collectively as ddNTPs. Additional examples of terminator compounds include 2'-$PO_4$ analogs of ribonucleotides (see, e.g., U.S. Application Publication Nos. 2005/0037991 and 2005/0037398). Other unconventional nucleotides include phosphorothioate dNTPs ([[a]-S] dNTPs), 5'[a]-borano-dNTPs, [a]-methyl-phosphonate dNTPs, and ribonucleoside triphosphates (rNTPs). Unconventional bases may be labeled with radioactive isotopes such as $^{32}P$, $^{33}P$, or $^{35}S$; fluorescent labels; chemiluminescent labels; bioluminescent labels; hapten labels such as biotin; or enzyme labels such as streptavidin or avidin. Fluorescent labels may include dyes that are negatively charged, such as dyes of the fluorescein family, or dyes that are neutral in charge, such as dyes of the rhodamine family, or dyes that are positively charged, such as dyes of the cyanine family.

The term "nucleic acid" or "polynucleotide" or "nucleic acid molecule" refers to a polymer that can be corresponded to a ribose nucleic acid (RNA) or deoxyribose nucleic acid (DNA) polymer, or an analog thereof. This includes polymers of nucleotides such as RNA, DNA, cDNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (*Science* 254:1497-1500, 1991). A nucleic acid can be or can include, e.g., a chromosome or chromosomal segment, a gene, a vector (e.g., an expression vector), an expression cassette, a naked DNA, cDNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

The term "oligonucleotide" refers to a nucleic acid that includes at least two nucleic acid monomer units (e.g., nucleotides). An oligonucleotide typically includes from 5 to 175 nucleic acid monomer units, more typically from eight to 100 nucleic acid monomer units, and still more typically from 10 to 50 nucleic acid monomer units (e.g., about 15, about 20, about 25, about 30, about 35, or more nucleic acid monomer units). The exact size of an oligonucleotide will depend on many factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (*Meth. Enzymol.* 68:90-99, 1979); the phosphodiester method of Brown et al. (*Meth. Enzymol.* 68:109-151, 1979); the diethylphosphoramidite method of Beaucage et al. (*Tetrahedron Lett.* 22:1859-1862, 1981); the triester method of Matteucci et al. *Am. Chem. Soc.* 103: 3185-3191, 1981); automated synthesis methods; or the solid support method of U.S. Pat. No. 4,458,066, or other methods known to those skilled in the art.

In one embodiment, the DNA polymerase of the present invention discriminates between a mismatched primer and a matched primer, wherein said primers hybridize to a target sequence, and wherein the mismatched primer comprises a non-canonical nucleotide at its 3' end in relation to the target sequence to which it hybridizes.

In another embodiment, the DNA polymerase of the present invention discriminates between a mismatched primer and a matched primer, wherein said primers hybridize to a target sequence, and
wherein the mismatched primer comprises a non-canonical nucleotide in a position of up to seven nucleotides from its 3' end in relation to the target sequence to which it hybridizes, preferably said mismatched primer comprises a non-canonical in the fourth and seventh position from its 3' end in relation to the target sequence.

The term "primer" as used herein refers to a oligonucleotide capable of acting as a point of initiation of template-directed nucleic acid synthesis when placed under conditions in which polynucleotide extension is initiated (e.g., under conditions comprising the presence of requisite nucleoside triphosphates (as dictated by the template that is copied) and a polymerase in an appropriate buffer and at a suitable temperature or cycle(s) of temperatures (e.g., as in a polymerase chain reaction). Primers can also be used in a variety of other oligonucleotide-mediated synthesis processes, including as initiators of de novo RNA synthesis and in vitro transcription-related processes (e.g., nucleic acid sequence-based amplification (NASBA), transcription mediated amplification (TMA), etc.). A primer is typically a single-stranded oligonucleotide (e.g., oligodeoxyribonucleotide). The appropriate length of a primer depends on the intended use of the primer but typically ranges from 6 to 60 nucleotides, more typically from 15 to 35 nucleotides. In one embodiment, the primer has 20 nucleotides. Short primer molecules generally require cooler temperatures to form sufficiently stable hybrid complexes with the target sequence on a template.

A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in ELISA assays), biotin, or haptens and proteins for which antisera or monoclonal antibodies are available. In one embodiment, the primer is a Lux primer. In another embodiment, the primer is a scorpion primer. In another embodiment, the primer is radiolabelled. In one embodiment, the primer is a Lux primer, a scorpion primer or is radiolabelled.

Also envisaged by the present invention is a primer that hybridizes to a template. Also envisaged by the present invention is a primer that hybridizes to a target sequence.

The term "hybridizes" as used in accordance with the present invention may relate to hybridizations under stringent or non-stringent conditions. If not further specified, the conditions are preferably non-stringent. Said hybridization conditions may be established according to conventional protocols described, for example, in Sambrook, Russell "Molecular Cloning, A Laboratory Manual", Cold Spring Harbor Laboratory, N.Y. (2001); Ausubel, "Current Protocols in Molecular Biology", Green Publishing Associates and Wiley Interscience, N.Y. (1989), or Higgins and Hames (Eds.) "Nucleic acid hybridization, a practical approach" IRL Press Oxford, Washington D.C., (1985). The setting of conditions is well known within the skill of the artisan and can be determined according to protocols described in the art. Thus, the detection of only specifically hybridizing sequences will usually require stringent hybridization and washing conditions such as 0.1×SSC, 0.1% SDS at 65° C. Non-stringent hybridization conditions for the detection of homologous or not exactly complementary sequences may be set at 6×SSC, 1% SDS at 65° C. As is well known, the length of the probe and the composition of the nucleic acid to be determined constitute further parameters of the hybridization conditions. Notably variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Additionally, a hybridization complex refers to a complex between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., Cot or Rot analysis) or between one nucleic acid sequence present in solution and another nucleic acid sequence immobilized on a solid support (e.g., membranes, filters, chips, pins or glass slides to which, e.g., cells have been fixed).

The terms "complementary" or "complementarity" refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands.

A "matched" primer is a hybridizing oligonucleotide that does not need to reflect the exact sequence of the target sequence but must be sufficiently complementary to hybridize to a target sequence. The term "hybridizing oligonucleotide" preferably refers to oligonucleotides, which display a complementary sequence of at least 30 or 40%, preferably at least 50%, more preferably at least 60%, even more preferably at least 70%, particularly preferred at least 80%, more particularly preferred at least 90%, even more particularly preferred at least 95%, 96%, 97% or 98% and most preferably at least 99% or 100% complementary to a target nucleic acid sequence.

In one embodiment, the matched primer comprises a canonical nucleotide at its 3' end in relation to the target sequence to which it hybridizes.

The term "canonical nucleotide" or "complementary nucleotide" means the standard Watson-Crick base pairs, which are A-U, A-T and G-C.

In another embodiment, the matched primer comprises a canonical nucleotide at its 3' end and/or in a position of up to seven nucleotides (bases) from its 3' end in relation to the target sequence to which it hybridizes and is at least 70% complementary to a target sequence. In another embodiment, the matched primer comprises a canonical nucleotide at its 3' end and/or in a position of up to seven nucleotides (bases) from its 3' end in relation to the target sequence to which it hybridizes and is at least 80% complementary to a target sequence. In another embodiment, the matched primer comprises a canonical nucleotide at its 3' end and/or in a position of up to seven nucleotides (bases) from its 3' end in relation to the target sequence to which it hybridizes and is at least 90% complementary to a target sequence. In another embodiment, the matched primer comprises a canonical nucleotide at its 3' end and/or in a position of up to seven nucleotides (bases) from its 3' end in relation to the target sequence to which it hybridizes and is at least 95% complementary to a target sequence. In another embodiment, the matched primer comprises a canonical nucleotide at its 3' end and/or in a position of up to seven nucleotides (bases) from its 3' end in relation to the target sequence to which it hybridizes and is at least 99% complementary to a target sequence. In another embodiment, the matched primer is 100% complementary to a target sequence.

In one embodiment, the matched primer comprises one, two, three, four, five six or seven canonical nucleotides in a position of up to seven nucleotides (bases) from its 3' end region in relation to the target sequence to which it hybridizes. In another embodiment, the matched primer comprises one, two, three, four, five six or seven canonical nucleotides in a position of up to seven nucleotides (bases) from its 3' end region in relation to the target sequence to which it hybridizes and is at least 80%, 90%, 95%, 99% complementary to a target sequence. In one embodiment, the matched primer is fully complementary (100% complementary) to the target sequence to which it hybridizes.

The "3' end region" comprises the last 5 nucleotides of the 3' end of a primer (matched and mismatched). In one embodiment, the matched primer comprises proxy-3'-terminally or a canonical nucleotide in its 3' end region in relation to the target sequence to which it hybridizes. "Proxy-3'-terminally" means the nucleotide, which is connected via a phosphate group with the 5' end with the nucleotide at the 3' end of the primer (matched or mismatched).

In another embodiment, the matched primer is able to hybridize to bisulfite treated DNA.

In one embodiment, the DNA polymerase of the present invention amplifies a template strand with the matched primer e.g. a fully complementary matched primer as efficient as the KlenTaq of SEQ ID NO: 2. In one embodiment, the DNA polymerase of the present invention amplifies a template strand with the matched primer e.g. a fully complementary matched primer as efficient as the Taq of SEQ ID NO: 1.

Such an efficiency can e.g. be measured by real-time PCR under equal conditions for every DNA polymerase tested. The efficiency can mean how fast a template is amplified by a given DNA polymerase.

In one embodiment, the DNA polymerase of the present invention amplifies a template strand with the matched primer e.g. a fully complementary matched primer with reduced activity when compared to the KlenTaq of SEQ ID NO: 2. In another embodiment, the DNA polymerase of the present invention amplifies a template strand with the matched primer e.g. a fully complementary matched primer with reduced activity when compared the Taq of SEQ ID NO: 1. In another embodiment, the DNA polymerase of the present invention amplifies a template strand with the matched primer e.g. a fully complementary matched primer with increased activity when compared to the KlenTaq of SEQ ID NO: 2. In another embodiment, the DNA polymerase of the present invention amplifies a template strand with the matched primer e.g. a fully complementary matched primer, with increased activity when compared the Taq of SEQ ID NO: 1.

In another embodiment, the DNA polymerase of the present invention amplifies the mismatched primer comprising at least one non-canonical nucleotide (base) in a position of two to seven (nucleotides) bases from the 3' primer end in relation to the target sequence with lesser efficiency than the matched primer e.g. a fully complementary matched primer. In another embodiment, the DNA polymerase of the present invention amplifies the mismatched primer comprising at least one non-canonical nucleotide (base) in a position of two to seven (nucleotides) bases from the 3' primer end in relation to the target sequence with lesser efficiency than a polymerase shown in SEQ ID NO: 1 or 2.

A "mismatched primer" is a hybridizing oligonucleotide that does not reflect the exact sequence of the target sequence but must be sufficiently complementary to hybridize to a target sequence. In one embodiment, the mismatched primer comprises a non-canonical nucleotide at its 3' end in relation to the target sequence to which it hybridizes. In another embodiment, the mismatched primer comprises at least one non-canonical nucleotide (base) in a position of up to seven (nucleotides) bases from the 3' primer end in relation to the target sequence. The non-canonical nucleotide or the mismatch can therefore be in the first, second, third fourth, sixth or seventh position. For example with a third position it is meant, when counted from the 3' end, the third position in 5' direction. This "position" is counted from the 3' end of the primer, wherein the position at the 3' end is position number 1 and the proxy-3'-terminally nucleotide is nucleotide number 2. This also holds true for the matched primer. Thus, with a mismatched primer comprising a non-canonical nucleotide in the first position from its 3' end in relation to the target sequence to which it hybridizes, it is meant a primer comprising a non-canonical nucleotide at its 3' end region in relation to the target sequence to which it hybridizes.

In one embodiment, the mismatched primer comprises a non-canonical nucleotide in a position of up to seven bases from its 3' end in relation to the target sequence to which it hybridizes. The mismatched primer can comprise 1, 2, 3, 4, 5, 6 or 7 non-canonical nucleotide (base) in a position of up to seven (nucleotides) bases from the 3' primer end in relation to the target sequence.

Alternatively, the nomenclature can be P+6, wherein P refers to a mismatched primer which comprises a non-canonical nucleotide (mismatch) at its 3' end in relation to the target sequence, and the number +1 indicates an elongation of the 3'-mismatched primer terminus by 1 canonically matched base (nucleotide) in the 3' direction. The elongation of the 3'-mismatched primer terminus can include 1, 2, 3, 4, 5, 6, 7, 8, 9 or 10 canonically matched bases. Preferably, the mismatched primer is a P+3 or P+6 primer (see also example 11).

In one embodiment, the DNA polymerase of the present invention discriminates between the matched primer e.g. fully complementary matched primer and a P+1, P+2, P+3, P+4, P+5 and/or P+6 mismatched primer. In one embodiment, the DNA polymerase of the present invention discriminates between the matched primer e.g. a fully complementary matched primer and the P+3 and/or P+6 mismatched primer.

The term "non-canonical" or "non-complementary" means a base pairing other than a Watson-Crick base pair, such as e.g. A-C, A-G, G-U, G-T, T-C, T-U, A-A, G-G, T-T, U-U, C-C, C-U.

In one embodiment, the mismatched primer comprises a non-canonical nucleotide at its 3' end region in relation to the target sequence to which it hybridizes. In another embodiment, the mismatched primer comprises proxy-3'-terminally a non-canonical nucleotide or in its 3' end region in relation to the target sequence to which it hybridizes.

In one embodiment, the mismatched primer comprises a non-canonical nucleotide at its 3' end and/or in a position of up to seven bases (nucleotides) from its 3' end in relation to the target sequence to which it hybridizes. In another embodiment, the mismatched primer comprises a non-canonical nucleotide at its 3' end and/or in a position of up to seven bases (nucleotides) from its 3' end in relation to the target sequence to which it hybridizes and is at least 70% complementary to a target sequence. In another embodiment, the mismatched primer comprises a non-canonical nucleotide at its 3' end and/or in a position of up to seven bases (nucleotides) from its 3' end in relation to the target sequence to which it hybridizes and is at least 80% complementary to a target sequence. In another embodiment, the mismatched primer comprises a non-canonical nucleotide at its 3' end and/or in a position of up to seven bases (nucleotides) from its 3' end in relation to the target sequence to which it hybridizes and is at least 90% complementary to a target sequence. In another embodiment, the mismatched primer comprises a non-canonical nucleotide at its 3' end and/or in a position of up to seven bases (nucleotides) from its 3' end in relation to the target sequence to which it hybridizes and is at least 95% complementary to a target sequence. In another embodiment, the mismatched primer comprises a non-canonical nucleotide at its 3' end and/or in a position of up to seven bases (nucleotides) from its 3' end in relation to the target sequence to which it hybridizes and is at least 99% complementary to a target sequence. In another embodiment, the mismatched primer comprises a non-canonical nucleotide at its 3' end and/or in a position of up to seven bases (nucleotides) from its 3' end in relation to the target sequence to which it hybridizes and is 100% complementary to a target sequence at the other positions. In another embodiment, the mismatched primer comprises one, two, three, four, five six or seven non-canonical nucleotides in a position of up to seven nucleotides (bases) from its 3' end region in relation to the target sequence to which it hybridizes and is at least 80%, 90%, 95%, 99% complementary to a target sequence. In another embodiment, the mismatched primer is able to hybridize to bisulfite treated DNA. In another embodiment, the mismatched primer comprises a non-canonical nucleotide at its 3' end in relation to the target sequence to which it hybridizes.

In one embodiment, the DNA polymerase of the present invention amplifies a template strand with the mismatched primer as efficient as the KlenTaq of SEQ ID NO: 2. In another embodiment, the DNA polymerase of the present invention amplifies a template strand with the mismatched primer as efficient as the Taq of SEQ ID NO: 1. In another embodiment, the DNA polymerase of the present invention amplifies a template strand with the mismatched primer with reduced activity when compared to the KlenTaq of SEQ ID NO: 2. In another embodiment, the DNA polymerase of the present invention amplifies a template strand with the mismatched primer with reduced activity when compared the Taq of SEQ ID NO: 1. In another embodiment, the DNA polymerase of the present invention amplifies a template strand with the mismatched primer with increased activity when compared to the KlenTaq of SEQ ID NO: 2. In another embodiment, the DNA polymerase of the present invention amplifies a template strand with the mismatched primer with increased activity when compared the Taq of SEQ ID NO: 1.

The present invention also relates to the use of a DNA polymerase of the present invention, for discrimination between matched and mismatched primers, wherein said primers hybridize to a target sequence, and wherein the mismatched primer comprises a non-canonical nucleotide at its 3' end in relation to the target sequence to which it hybridizes.

The present invention also relates to the use of a DNA polymerase of the present invention, for discrimination between matched and mismatched primers, wherein said primers hybridize to a target sequence, and wherein the mismatched primer comprises a non-canonical nucleotide in a position of up to seven bases from its 3' end in relation to the target sequence to which it hybridizes.

In one embodiment, the DNA polymerase of the present invention, exhibits amplification of a target sequence with a matched primer with a lower threshold crossing (c(t)) cycle number value than with a mismatched primer, wherein said primers hybridize to a target sequence, and wherein the mismatched primer comprises a non-canonical nucleotide at its 3' end and/or in a position of up to seven bases/nucleotides from its 3' end in relation to the target sequence to which it hybridizes.

"Discrimination between matched and mismatched primer" as used herein refers to the ability of the DNA polymerase of the present invention to distinguish the matched primer (sequence) from the mismatched primer (sequence) when extending a nucleic acid in a template-dependent manner by attaching (e.g., covalently) one or more nucleotides to matched and/or mismatched primer.

In another embodiment, the DNA polymerase of the present invention, exhibits amplification of a target sequence with a matched primer with a lower threshold crossing (c(t)) cycle number value than with a mismatched primer, wherein said primers hybridize to a target sequence, and wherein the mismatched primer comprises a non-canonical nucleotide at its 3' end in relation to the target sequence to which it hybridizes, wherein the difference between the c(t) value of the matched and the c(t) value of the mismatched primer is at least 9, preferably at least 10, 11, 12, 13, 14, 15, 16, 17, 18, 19, 20.

Further the DNA polymerase of the present invention can distinguish the fully complementary sequence of a matched primer (sequence) and the mismatched primer comprising a non-canonical nucleotide at its 3' end in relation to the target sequence to which it hybridizes. Also, the DNA polymerase of the present invention can distinguish the fully complementary sequence of a matched primer (sequence) and the mismatched primer comprising a non-canonical nucleotide in a position of up to seven bases/nucleotides from its 3' end in relation to the target sequence to which it hybridizes.

In one embodiment, the DNA polymerase of the present invention distinguishes between the fully complementary sequence of a matched primer (sequence) and the mismatched primer comprising a non-canonical nucleotide in a P+3 and/or P+6 positions relative to the target sequence to which it hybridizes.

For example, in one embodiment, the DNA polymerase can extend the matched primer with greater efficiency than the mismatched primer in a target sequence-dependent manner by attaching (e.g., covalently) one or more nucleotides to the primer. Here, a greater efficiency can for example mean that e.g. in RT-PCR lower threshold crossing cycle c(t) values (numbers) are observable for the matched primer than for the mismatched primer. In one embodiment, the difference between the c(t) value of the matched primer and the c(t) value of the mismatched primer is between 9-20, preferably, between 10-19, more preferably between 11-18, even more preferably between 13 and 18. In one embodiment, the difference between the c(t) value of the matched primer and the c(t) value of the mismatched primer is between 15-18.

Other experimental settings that can be used to determine the difference between the matched and the mismatched primer are also disclosed in the examples of the present invention.

A greater efficiency can also mean that the product formed with standard PCR using e.g. a matched forward and reverse primer in one reaction and a mismatched forward and a matched reverse primer in a second reaction in the same experimental setting is greater for the one reaction than for the second reaction, when quantitatively analyzed by western blot or agarose gel and optionally compared to a control such as actin.

The DNA polymerase can also extend a mismatched primer with greater efficiency than a matched primer in a target sequence-dependent manner by attaching (e.g., covalently) one or more nucleotides to the primer.

In another embodiment, the DNA polymerase of the present invention extends the matched primer and does not extend the mismatched primer, when extending the primer in a target sequence-dependent manner by attaching (e.g., covalently) one or more nucleotides to the primer.

In yet another embodiment, the DNA polymerase of the present invention extends the mismatched primer and does not extend the matched primer, when extending the primer in a target sequence-dependent manner by attaching (e.g., covalently) one or more nucleotides to the primer.

In one embodiment, the elongation of the matched primer is increased by 14-fold when compared to the mismatched primer.

"Threshold crossing (c(t)) cycle number" as used herein refers to a method of DNA quantification by quantitative PCR relying on plotting fluorescence against the number of cycles on a logarithmic scale. A threshold for detection of DNA-based fluorescence is set at minimum slightly above background. The number of cycles at which the fluorescence exceeds the threshold is called the threshold (crossing) cycle ($C_t$) or, according to the MIQE guidelines, quantification cycle ($C_q$). The threshold is either manually selected or auto-selected to fall several standard deviations above base-line fluorescence and below the plateau phase, where the amplification begins to attenuate. Typically, the threshold is adjusted to the mid-point of the exponential phase of the PCR, at a location suitable for all samples in the experiment. The $C_T$ or c(t) (cycles to threshold) value for a given reaction is defined as the cycle number at which the fluorescence emission intersects the fixed threshold. For example, SYBR Green I and fluorescent probes can be used in real-time PCR for template DNA quantification. Fluorescence from each sample is collected once each cycle during PCR, and plotted against the cycle number. The starting template concentration correlates inversely to the time of first appearance of fluorescence signal. Signal appear earlier (at lower cycle number) the higher the concentration of a template. Because PCR is exponential, the correlation is logarithmic.

The terms "amplification" or "amplification reaction" means the replication or increase in the number of copies of nucleic acids such as DNA, cDNA or RNA, preferably DNA. Preferably, such amplification is primer-dependent.

The present invention also relates to the use of a DNA polymerase of the present invention, for detection of at least one single nucleotide polymorphism (SNP), which SNP is comprised in a target sequence.

The term "template" means the piece of a nucleic acid molecule which is to be analyzed or amplified e.g. by PCR. Such a template comprises the target sequence. As such the template can be of the same type as the target sequence. For example it can be DNA, cDNA RNA, preferably genomic DNA, more preferably genomic DNA of a bacterium or a vertebrate, more preferably human genomic DNA. In one embodiment, the target sequence is the template. Usually, templates can be in a range of 5-200 nucleotides, preferably in the range of 10-150 nucleotides, more preferably in the range of 25-100 nucleotides, even more preferably in the range of 23-60 nucleotides. In one embodiment, the template has a length of 33 nucleotides. However, a template may also comprise much larger sequences e.g. genomic DNA. In another embodiment, the template has been treated with bisulfite.

In one embodiment, the template is purified. In another embodiment, the template is not purified. Such "purification" can be done by e.g. ethanol precipitation phenol-chloroformextraction or Minicolumn purification. Purification can also comprise cell lysis. In yet another embodiment, the template comprises a gene or a part of a gene.

The term "target sequence" in accordance with the present invention means a nucleic acid such as DNA, RNA or cDNA comprising a particular region of interest to which the primers of the present invention can hybridize to. In one embodiment, a matched and a mismatched primer can bind to the same target sequence. The target sequence can be of different lengths. Usually, a target sequence can be in a range of 5-200 nucleotides, preferably in the range of 10-150 nucleotides, more preferably in the range of 10-50 nucleotides. In one embodiment, the target sequence of the mismatched primer is different to the target sequence of the matched primer. In another embodiment, the target sequence of the mismatched primer is equal to the target sequence of the matched primer. In another embodiment of the present invention, the target sequence is a DNA sequence that has been treated with bisulfite.

The target sequence is preferably comprised in genomic DNA. In one embodiment, the target sequence is comprised in the genomic DNA of a subject. In one embodiment, the target sequence is comprised in the genomic DNA of a bacterium or a vertebrate. In another embodiment, the target sequence is comprised in the genomic DNA of a bacterium.

In another embodiment, different target sequences are analyzed at the same time, e.g. in the same reaction tube.

A "subject" in accordance with the present invention means a bacterium, invertebrate or vertebrate, preferably a bacterium or a vertebrate, most preferably a human subject.

A "bacterium" in the sense of the present invention includes bacteria of the genus *Escherichia* or *Pseudomonas* such as e.g. *E. coli*, *P. putila* or *P. fluorescens*; and or bacteria of the genus *Bacillus, Corynebocterium, Staphylococcus* or *Lactococcus*, such as *B. subtilis* or *B. megaterium* or of the genus *Serratia, Brevibocterium, Corynebocterium, Microbocterium*. A bacterium can also be a bacterium as defined below.

A "vertebrate" in the sense of the present invention includes vertebrate fish, dog, cat, horse, mouse, rat, rabbit, chicken, guniea pig, ape or human, preferably a human subject. In another embodiment, the target sequence is comprised in the genomic DNA of a human subject.

The target sequence can be present in a test sample, which comprises DNA, cDNA or RNA, preferably genomic DNA. In one embodiment, the test sample is a cell lysate made from a bacterium, bacterial culture or cell culture. The test sample can also be comprised in an animal, preferably a vertebrate and more preferably a human subject. In another embodiment, the test sample is selected from biopsy, blood, salvia, stool, urine. In another embodiment, the biopsy, blood, salvia, stool, urine is contained in a human subject.

The present invention also relates to the use of the DNA polymerase of the present invention, wherein the target sequence is comprised in genomic DNA, preferably the genomic DNA of a subject, preferably a bacterium or a vertebrate, most preferably a human subject.

In one embodiment, the present invention relates to the use of the DNA polymerase of the present invention, wherein the target sequence is comprised in a test sample.

In one embodiment the present invention relates to the use of the DNA polymerase of the present invention, wherein the test sample is selected from biopsy, blood, salvia, stool, urine.

A "particular region of interest" can for example be a region on a DNA comprising a SNP and/or a methylated cytosine.

The term "SNP" means a DNA sequence variation occurring when a single nucleotide—A, T, C or G—in the genome (or other shared sequence) differs between members of a biological species or paired chromosomes in a subject. For example, two sequenced DNA fragments from different subjects, AAGCCTA to AAGCTTA, contain a difference in a single nucleotide. Almost all common SNPs have only two alleles. Single-nucleotide polymorphisms may fall within coding sequences of genes, non-coding regions of genes, or in the intergenic regions (regions between genes). SNPs within a coding sequence do not necessarily change the amino acid sequence of the protein that is produced, due to degeneracy of the genetic code. SNPs in the coding region are of two types, synonymous and nonsynonymous SNPs. Synonymous SNPs do not affect the protein sequence while nonsynonymous SNPs change the amino acid sequence of protein. The nonsynonymous SNPs are of two types: missense and nonsense. SNPs that are not in protein-coding regions may still affect gene splicing, transcription factor binding, messenger RNA degradation, or the sequence of non-coding RNA. Gene expression affected by this type of SNP is referred to as an eSNP (expression SNP) and may be upstream or downstream from the gene. The skilled artesian knows databanks, which include lists of SNPs such as a data bank provided by NCBI (http:www.ncbi.nlm.nih.gov/SNP)

or wikipedia (http://www.snpedia.com/index.php/SNPedia). Every submitted variation receives a submitted SNP ID number ("ss#") (Sherry et al., 2001). This accession number is a stable and unique identifier for that submission. Unique submitted SNP records also receive a reference SNP ID number ("rs#"; "refSNP cluster").

Exemplary SNP detection methods are described in Chen et al., "Single nucleotide polymorphism genotyping: biochemistry, protocol, cost and throughput" Pharmacogenomics J. 3(2):77-96 (2003); Kwok et al., "Detection of single nucleotide polymorphisms" Curr. Issues Mol. Biol. 5(2):43-60 (April 2003); Shi, "Technologies for individual genotyping: detection of genetic polymorphisms in drug targets and disease genes" Am. J. Pharmacogenomics 2(3):197-205 (2002); and Kwok, "Methods for genotyping single nucleotide polymorphisms" Annu. Rev. Genomics Hum. Genet. 2:235-58 (2001). Exemplary techniques for high-throughput SNP detection are described in Marnellos, "High-throughput SNP analysis for genetic association studies" Curr. Opin. Drug Discov. Devel. 6(3):317-21 (May 2003). Common SNP detection methods include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted an genetic arrays, ligation with rolling circle amplification, homogeneous ligation, OLA (U.S. Pat. No. 4,988,167), multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection. Detection of multiple different alleles can also be accomplished using multiplex reactions, which allow the detection of multiple different alleles in a single reaction. In multiplex reactions, two or more allele-specific primers are used to extend and amplify SNPs or multiple nucleotide polymorphisms or alleles. Exemplary methods for multiplex detection of single and multiple nucleotide polymorphisms are described in U.S. Patent Publication No. 2006/0172324.

In one embodiment, the SNP is comprised in the target sequence. In another embodiment, the SNP is comprised in the target sequence, wherein the SNP is selected form the group consisting of SNPs associated with factor II protrombin e.g. rs6025 (R506Q), rs1799963 (G20210A); SNPs associated with ApoB e.g. rs5742904 (R3500Q), rs12713559 (R3531C) and i4000339 (R3500W); SNPs associated with alpha-1-antitrypsin-deficiency e.g. rs17580 and rs28929474; SNPs associated with lactose intolerance e.g. rs4988235, rs182549; a SNP associated with fructose-intolerance e.g. rs1800546 (A149P); SNPs associated with hemochromatosis e.g. rs1800562 (C282Y), rs1799945 (H63D), and rs1800730 (S65C); a SNP associated with chronic myeloproliferative disorders e.g. rs77375493 (JAK2-mutation V617F); a SNP associated with the methylenetetrahydrofolate reductase (MTHFR) e.g. rs1801133 (C677T); SNPs associated with cystic fibrosis e.g. i4000294 (G85E), i4000295 (R117H), rs35516286 (I148T), i4000296 (R334W), i4000297 (R347P/H), i4000291 (A455E), i4000299 (V520F), rs113993958 (D110H), rs113993959 G542X, i4000301 (S549N), i4000302 (S549R), rs75527207 (G551D), i4000306 (R553X), i4000307 (R560T), i4000308 (R1162X), i4000309 (W1282X), i4000311 (N1303K); SNPs associated with APOE e.g. rs429358, rs7412; a SNP associated with glutathione S transferase M (GSTM1) e.g. rs4147565; a SNP associated with GSTT1 e.g. rs1695 (I105V); a SNP associated with human leucocyte antigen (HLA) subtypes e.g. rs27044 (HLA-B*2705), rs1265181 (HLA-Cw0602); a SNP associated with interleukin-28B e.g. rs12979860.

The present invention also relates to the DNA polymerase of the present invention for use in in vitro diagnosis of a disease of a subject, which disease is associated with a SNP in a target sequence, which target sequence is comprised in the genomic DNA of a subject.

In one embodiment, the target sequence can also comprise at least one SNP. The target sequence can comprise 1, 2, 3, 4, 5, 6, 7, 8, 9, 10 or more SNPs. In one embodiment, the target sequence comprises one SNP. In another embodiment, the target sequence comprises two SNPs. In a further embodiment the target sequence comprises three SNPs.

In one embodiment the DNA polymerase of the present invention is for use in in vitro diagnosis of a disease of a subject, which disease is associated with a SNP in a target sequence, which disease is associated with a SNP in a target sequence, wherein the SNP is selected form the group consisting of SNPs associated with factor II protrombin, with factor V Leiden, with ApoB, with coeliac disease, with alpha-1-antitrypsin-deficiency, with lactose intolerance, with fructose-intolerance, with hemochromatosis, with chronic myeloproliferative disorders, with the methylenetetrahydrofolate reductase; with cystic fibrosis, with APOE genotypes, with glutathione S transferase M (GSTM1) genotyping, with GSTT1 genotyping, with human leucocyte antigen (HLA) subtypes or with interleukin-28B.

In another embodiment, the DNA polymerase is for use in in vitro diagnosis of a disease of a subject, which disease is associated with a SNP in a target sequence, wherein said SNP is associated with Factor V Leiden or Factor II prothrombin.

The present invention also relates to the use of a DNA polymerase of the present invention as a diagnostic for diagnosing a disease of a subject, which disease is associated with a SNP or a methylation status of a target sequence, which target sequence is comprised in the genomic DNA of the subject.

The present invention further relates to an in vitro method for detecting at least one SNP in at least one template comprising contacting the DNA polymerase of the present invention with
  i) the at least one template;
  ii) at least one matched and/or at least one mismatched primer,
    wherein said primers hybridize to the target sequence, and
    wherein the mismatched primer comprises a non-canonical nucleotide in a position of up to seven bases/nucleotides from its 3' end in relation to the target sequence to which it hybridizes; and
  iii) nucleoside triphosphates.

In one embodiment, this method includes a melting point analysis using a double-strand specific dye e.g., SYBR-GreenI.

The term "detecting at least one SNP" means the determination of the absence or presence of the at least one SNP.

The present invention additionally, also relates to the use of the DNA polymerase according the present invention for detection of a methylation status of a target sequence.

The "methylation status of a target sequence" means the presence or absence of one or more methylated cytosines in e.g. a genomic DNA. DNA methylation and chromatin structure are often altered in diseases particularly in cancer or drug sensitivity of a vertebrate (for a list of possible diseases see Heyn, Esteller 2012). The term "methylation status" also includes the presence or absence of 5-methylcytosine. 5-Methylcytosines are frequently found as symmetrical 5-methylations of the dinucleotide CpG within or nearby promoters.

They are called "CpG islands" of which there are about 30,000 in the human genome. The usual formal definition of a CpG island is a region with at least 200 bp, and a GC percentage that is greater than 50%, and with an observed-to-expected CpG ratio that is greater than 60% (see for example Gardiner-Garden et al., *Journal of Molecular Biology* 196 (2): 261-82.). The "observed-to-expected CpG ratio" is calculated by formula ((Num of CpG/(Num of C×Num of G))×Total number of nucleotides in the sequence). 88% of active promoters are associated with CpG-rich sequences and might be regulated by DNA methylation.

"5'-CpG-3'" in accordance with the present invention means that the CpG is in a position such that the "C" faces the 5' end of the target sequence and the "G" faces the 3' end of the target sequence. The "p" in CpG refers to the phosphodiester bond between the cytosine and the guanine, which indicates that the C and the G are next to each other in sequence, regardless of being single- or double-stranded. In a CpG site, both C and G are found on the same strand of DNA and are connected by a phosphodiester bond. This is a covalent bond between atoms, stable and permanent as opposed to the three hydrogen bonds established after base-pairing of C and G in opposite strands of DNA.

In addition, cytosine methylation is part of the restriction modification system of many bacteria.

Bacterial DNAs are methylated periodically throughout the genome. The methylation of native DNA acts as a sort of primitive immune system, allowing the bacteria to protect themselves from infection by bacteriophage. These restriction enzymes are the basis of restriction fragment length polymorphism (RFLP) testing, used to detect DNA polymorphisms.

In a given target sequence 1, 2, 3, 4, 5, 6, 7, 8, 9, 10 or more methylated cytosines, can be present or absent. In one embodiment, the target sequence comprises one methylated cytosine or one unmethylated cytosine. In one embodiment, the target sequence comprises one methylated cytosine or one unmethylated cytosine. In another embodiment, the target sequence comprises two methylated cytosines or two unmethylated cytosines.

Also meant by methylation status is the presence or absence of one or more methylated cytosines in e.g. a genomic DNA of a bacterium. In a given target sequence 1, 2, 3, 4, 5, 6, 7, 8, 9, 10 or more methylated cytosines can be present or absent. In one embodiment, the target sequence comprises one methylated cytosine. In one embodiment, the target sequence comprises one methylated cytosine or one unmethylated cytosine. In another embodiment, the target sequence comprises two methylated cytosine or two unmethylated cytosine.

In a particular embodiment, the target sequence comprises at least one defined 5'-CpG-3'. The target sequence can also comprise 2, 3, 4, 5, 6, 7, 8, 9, 10 or more 5'-CpG-3'. Thus, in one embodiment, the target sequence comprises one 5'-CpG-3'. In another embodiment, the target sequence comprises two 5'-CpG-3'. In yet another embodiment, the target sequence comprises 3 5'-CpG-3'.

Thus, in one embodiment the present invention relates to the use of the DNA polymerase of the present invention for detection of the methylation status of a gene, which gene is comprised in a target sequence, wherein said gene is selected form the group consisting of APC, AR, BMAL1, BRACA1, CDH1, CDH11, CDH13, CDKN2A, CDKN2B, DAPK1, EMP3, ESR1, GSTP1, IGFBP3, LGALS3, MASPIN, MGMT, MLH1, NORE1A, NSD1, PYCARD, RARB, RASSF1A, RBP1, RIZ1, S100P, SEPT9, SFRP1, SFRP2, SNCG, SOCS1, TFPI2, THBS1, TIG1, TMP2, TP73, TSHR, VHL, WIF, WRN, SEPT9.

A "gene" when used herein is, so to say, a species of a nucleotide sequence and comprises a coding sequence for a gene and, optionally a 5'-UTR (containing, for example, expression control elements such as a promoter) and/or 3'-UTR (containing, for example, a termination signal sequence). The gene may be composed of exons and introns or may be free of introns, thus merely composed of exons. It may be composed of DNA, preferably genomic DNA. In another embodiment, the target sequence comprises at least one defined 5'-CpG-3' in the SEPT9 gene.

In another embodiment, the target sequence comprises at least one defined 5'-CpG-3' in the SEPT9 gene.

In another embodiment, the DNA polymerase is for use in in vitro diagnosis of a disease of a subject, which disease is associated with methylation status of a target sequence wherein said methylation status is associated with the drug sensitivity of said subject.

The term "drug intolerance" or "drug sensitivity" refers to a lower threshold to the normal pharmacologic action of a drug.

Therefore, in one embodiment, of the present invention, the methylation status of a target sequence is associated with cancer.

A "cancer" the term "cancer" and "cancerous" refer to or describe the physiological as used by the present invention means a condition in mammals that is typically characterized by unregulated cell growth as also described above. Different genes can be hypermethylated upon cancer (for a list please see Heyn and Esteller 2012).

Cancers are classified by the type of cell that the tumor cells resemble and is therefore presumed to be the origin of the tumor. These types include: carcinoma, sarcoma, lymphoma and leukemia, germ cell tumors, blastoma.

A "carcinoma" means cancers derived from epithelial cells. This group includes cancers like e.g. prostate, lung, pancreas, breast, ovaries and colon. Examples include adenocarcinoma, squamous cell carcinoma, adenosquamous carcinoma, anaplastic carcinoma, large cell carcinoma, small cell carcinoma. There are also a large number of rare subtypes of anaplastic, undifferentiated carcinoma. Examples include Askin's tumor, sarcoma botryoides, chondrosarcoma, Ewing's, malignant hemangioendothelioma, malignant schwannoma, osteosarcoma, soft tissue sarcomas such as cystosarcoma, angiosarcoma, epithelioid sarcoma, liposarcoma, and the like.

A "lymphoma and leukemia" means two classes of cancer arising from hematopoietic (blood-forming) cells that leave the marrow and tend to mature in the lymph nodes and blood, respectively. Leukemia means bone marrow-derived cells that normally mature in the bloodstream and lymphoma means bone marrow-derived cells that normally mature in the lymphatic system.

Examples of a lymphoma include follicular lymphoma, diffuse large B cell lymphoma, mantle cell lymphoma, B-cell chronic lymphocytic leukemia/lymphoma, MALT lymphoma, Burkitt's lymphoma, mycosis fungoides peripheral T-cell lymphoma, not-otherwise-specified nodular sclerosis form of Hodgkin lymphoma, Hodgkin's lymphoma.

Examples of leukemia include acute lymphoblastic leukemia (ALL) for example precursor B acute lymphoblastic leukemia, precursor T acute lymphoblastic leukemia, Burkitt's leukemia, and acute biphenotypic leukemia; chronic lymphocytic leukemia (CLL) like e.g. B-cell prolymphocytic leukemia; acute myelogenous leukemia (AML) for example acute promyelocytic leukemia, acute myeloblastic leukemia, and acute megakaryoblastic leukemia; chronic myelogenous leukemia (CML) for example chronic monocytic leukemia; hairy cell leukemia (HCL) or T-cell prolymphocytic leukemia (T-PLL) Large granular lymphocytic leukemia and adult T-cell leukemia.

A "germ cell tumor" means cancers derived from pluripotent cells, most often presenting in the testicle or the ovary (seminoma and dysgerminoma, respectively). Examples include germinoma (including dysgerminoma and seminoma), dysgerminom, seminoma, embryonal carcinoma, endodermal sinus tumor, choriocarcinoma, teratoma including mature teratoma, dermoid cyst, immature teratoma, teratoma with malignant transformation, polyembryoma, gonadoblastoma. Such tumors can be localized in the head, neck, mediastinum, pelvis, ovary, testis.

A "blastoma" means cancers derived from immature "precursor" cells or embryonic tissue. Examples include hepatoblastoma, medulloblastoma, nephroblastoma, neuroblastoma, pancreatoblastoma, pleuropulmonary blastoma, retinoblastoma, glioblastoma multiforme.

"Metastasis or metastases" refers to the process by which cancer spreads from the location at which the cancer initiated as a tumor to one or more distant locations in the body by migration of one or more cancerous cells. These terms also include micro-metastasis wherein the formation of tumors at distal locations correspond to small aggregates of cancer cells that are visible microscopically. These terms also refer to the secondary cancerous growth resulting from the spread of the primary tumor from the original location.

Thus in a particular embodiment the methylation status of a target sequence is associated, wherein the cancer is a carcinoma, sarcoma, lymphoma or leukemia, germ cell tumors, blastoma or metastasis.

Thus in a particular embodiment the methylation status of a target sequence is associated with a cancer, wherein the cancer is a adenocarcinoma, squamous cell carcinoma, adenosquamous carcinoma, anaplastic carcinoma, large cell carcinoma, small cell carcinoma, Askin's tumor, sarcoma botryoides, chondrosarcoma, Ewing's, malignant hemangioendothelioma, malignant schwannoma, osteosarcoma, soft tissue sarcomas, follicular lymphoma, diffuse large B cell lymphoma, mantle cell lymphoma, B-cell chronic lymphocytic leukemia/lymphoma, MALT lymphoma, Burkitt's lymphoma, mycosis fungoides peripheral T-cell lymphoma, not-otherwise-specified nodular sclerosis form of Hodgkin lymphoma, Hodgkin's lymphoma, follicular lymphoma, diffuse large B cell lymphoma, mantle cell lymphoma, B-cell chronic lymphocytic leukemia/lymphoma, MALT lymphoma, Burkitt's lymphoma, mycosis fungoides peripheral T-cell lymphoma, not-otherwise-specified nodular sclerosis form of Hodgkin lymphoma, Hodgkin's lymphoma, acute lymphoblastic leukemia (ALL) for example precursor B acute lymphoblastic leukemia, precursor T acute lymphoblastic leukemia, Burkitt's leukemia, and acute biphenotypic leukemia; chronic lymphocytic leukemia (CLL) like e.g. B-cell prolymphocytic leukemia; acute myelogenous leukemia (AML) for example acute promyelocytic leukemia, acute myeloblastic leukemia, and acute megakaryoblastic leukemia; chronic myelogenous leukemia (CML) for example chronic monocytic leukemia; hairy cell leukemia (HCL) or T-cell prolymphocytic leukemia (T-PLL) Large granular lymphocytic leukemia and adult T-cell leukemia, germinoma (including dysgerminoma and seminoma), dysgerminom, seminoma, embryonal carcinoma, endodermal sinus tumor, choriocarcinoma, teratoma including mature teratoma, dermoid cyst, immature teratoma, teratoma with malignant transformation, polyembryoma, gonadoblastoma, hepatoblastoma, medulloblastoma, nephroblastoma, neuroblastoma, pancreatoblastoma, pleuropulmonary blastoma, retinoblastoma, glioblastoma multiforme.

The present invention relates to a DNA polymerase of the present invention for use in in vitro diagnosis of a disease of a subject, which disease is associated with methylation status of a target sequence, which target sequence is comprised in the genomic DNA of a subject.

In one embodiment, the DNA polymerase is for use in in vitro diagnosis of a disease of a subject, which disease is associated with methylation status of a target sequence, wherein the target sequence comprises at least one 5'-CpG-3'.

In another embodiment, the DNA polymerase is for use in in vitro diagnosis of a disease of a subject, which disease is associated with methylation status of a target sequence, wherein said methylation status is associated with a disease of the group selected from Alzheimer's disease, Angelman syndrome, atherosclerosis, ATRX syndrome, Diabetes type 1, Fridrich's ataxia, immunodeficiency, centromeric region instability and facial abnormalities syndrome, Multiple sclerosis, Prader-Willi syndrome, Rett's syndrome, rheumatoid arthritis, Systemic lupus erythematosus.

In another embodiment, the DNA polymerase is for use in in vitro diagnosis of a disease of a subject, which disease is associated with methylation status of a target sequence, wherein said methylation status is associated with cancer. In one embodiment, said cancer is selected from the group consisting of prostate cancer, colon cancer, lung cancer, bladder cancer, leukemia, lymphoma, breast cancer, ovarian cancer, esophagus cancer, gastric cancer, liver cancer, head and neck cancer, colon cancer, stomach cancer, glioma, pancreas cancer, squamous cell carcinoma, endometrium cancer, thyroid cancer, neuroblastoma, kidney cancer.

Thus, in one embodiment, the DNA polymerase of the present invention is used for the detection of methylated cytosine in at least one template or target sequence. In another embodiment, the DNA polymerase of the present invention is used for the detection of the presence or absence of methylated cytosine in a template or target sequence. In one embodiment, the DNA polymerase of the present invention can be used for the detection of methylated cytosine in a template or target sequence. In another embodiment, the DNA polymerase of the present invention can be used for the detection of unmethylated cytosine in a template or target sequence.

In addition the present invention relates to an in vitro method for detecting at least one methylated nucleotide, preferably cytosine in at least one template comprising contacting the DNA polymerase of the present invention with
i) at least one template;
ii) at least one matched and/or at least one mismatched primer,
  wherein said primers hybridize to the target sequence, and
  wherein the mismatched primer comprises a non-canonical nucleotide in a position of up to seven bases (nucleotides) from its 3' end in relation to the target sequence to which it hybridizes; and
iii) nucleoside triphosphates.

In one embodiment, the in vitro method is for detecting at least one, two, three, four, five or six methylated nucleotides.

In one embodiment, the in vitro method for detecting at least one methylated nucleotide of the present invention is performed by PCR, preferably RT-PCR or isothermal amplification or methylation specific PCR.

In one embodiment, the in vitro method for detecting at least one methylated nucleotide of the present invention further comprises comparing an obtained result to a control sample or control value.

The in vitro method for detecting at least one methylated nucleotide or the in vitro method for detecting at least one SNP of the present invention can include the addition of the mismatched and the matched primer. The methods of the present invention can include the addition of the mismatched or the matched primer, for example the addition of only the mismatched or only the matched primer.

The in vitro method for detecting at least one methylated nucleotide or the in vitro method for detecting at least one SNP of the present invention can also include the addition of more than one primer. For example 1, 2, 3, 4, 5, 6, 7, 8, 9, 10, 11, or 12 primers can be added. In one embodiment one matched and one mismatched primer is added.

The in vitro method for detecting at least one methylated nucleotide or the in vitro method for detecting at least one SNP of the present invention can also include at least one template. For example, 1, 2, 3, 4, 5, 6, 7, 8, 9, 10, 11, or 12 templates can be added. In one embodiment one template is added. In another embodiment, two templates are added. The two templates can be different in only one point mutation, so only one SNP. The two templates can also be two alleles. The two templates can be different in their methylation status.

The in vitro method for detecting at least one methylated nucleotide or the in vitro method for detecting at least one SNP of the present invention can include at least one template, which comprises the target sequence. The target sequence can have different features, which are disclosed herein.

The in vitro method for detecting at least one methylated nucleotide of the present invention includes detection of methylated cytosine.

The in vitro method for detecting at least one methylated nucleotide or the in vitro method for detecting at least one SNP of the present invention can include that only specific nucleoside triphosphates are used. For example only dNTPs, ddNTPs or rNTPs may be present in the methods. It can also be that 1, 2 or 3 different types of dNTPs are present in the method. It can also be that 1, 2 or 3 different types of rNTPs are present in the methods.

In one embodiment, the method for detecting at least one methylated nucleotide or the method for detecting at least one SNP of the present invention, can include a melting point analysis using a double-strand specific dye e.g. SYBRGreenI. Such double-strand specific dyes are described herein.

Also amplicons (so amplificated templates) can be detected by e.g. double-stranded specific dyes. Also so called hydrolysis probes (TaqMan probes), dual hybridization probes, molecular beacons, scorpions can be used.

The term "melting curve analysis" means an assessment of the dissociation-characteristics of double-stranded DNA during heating. As the temperature is raised, the double strand begins to dissociate leading to a rise in the absorbance intensity, hyperchromicity. The temperature at which 50% of DNA is denatured is known as the melting point. The temperature-dependent dissociation between two DNA-strands can be measured using a DNA-intercalating fluorophore such as SYBR Green I, EvaGreen or fluorophore-labelled DNA probes. In the case of SYBR green, the dissociation of the DNA during heating is measurable by the resulting large reduction in fluorescence. It is also possible to set the software to acquire fluorescence above primer-dimers' melting temperature but below that of the target. For example, SYBR Green I or another double-strand specific dye, can be used in multiplex reactions, when these are coupled to melting point analysis—this can also be seen e.g. in the examples of the present invention (see also Arya et a., 2005)

In another embodiment, the method for detecting at least one methylated nucleotide or the method for detecting at least one SNP of the present invention can include multiplex reactions performed with different double strand specific dyes.

For example in real time PCR absolute and relative quantifications are generally possible.

In another embodiment, the method for detecting at least one SNP of present invention is performed by real time PCR, by standard PCR and subsequent analysis on agarose gel, by an allele-specific amplification through real time PCR or by tetra-primer amplification-refractory mutation system PCR or by isothermal amplification.

In another embodiment, the method for detecting at least one methylated nucleotide or the method for detecting at least one SNP of the present invention is performed by standard PCR and subsequent analysis on agarose gel.

A "standard PCR" or "polymerase chain reaction (PCR)" is a technique to amplify a single or a few copies of DNA or cDNA known to the skilled artesian. This amplification can be across several orders of magnitude, generating thousands to millions of copies of a particular DNA sequence. Almost all PCR applications employ a heat-stable DNA polymerase, such as Taq polymerase or KlenTaq. The DNA polymerase enzymatically assembles a new DNA strand from nucleotides, by using single-stranded DNA as a template and oligonucleotides (also called primers), which are required for initiation of DNA synthesis. Typically, the primers are designed as such that they hybridize to the 5' and 3' boarders of the target sequence. In the first step, the two strands of the DNA double helix are physically separated at a high temperature in a process called DNA melting. In the second step, the temperature is lowered and the two DNA strands become templates for the DNA polymerase to selectively amplify the target DNA. The selectivity of PCR results from the use of primers that are complementary to the DNA region targeted for amplification under specific thermal cycling conditions. The amplicons generated by PCR can then be analyzed e.g. on an agarose gel.

In another embodiment, the method for detecting at least one methylated nucleotide or the method for detecting at least one SNP of the present invention is performed by real time PCR.

A "real-time PCR" or "Real-time Polymerase Chain Reaction (RT-PCR)" is the ability to monitor the progress of the PCR as it occurs (i.e., in real time). Data is therefore collected throughout the PCR process, rather than at the end of the PCR. In real-time PCR, reactions are characterized by the point in time during cycling when amplification of a target is first detected rather than the amount of target accumulated after a fixed number of cycles. There are two main methods used to perform quantitative PCR: dye-based and probe-based detection. Both methods rely on calculating the initial (zero cycle) DNA concentration by extrapolating back from a reliable fluorescent signal. The basic principle of this method is known in the art (Arya et al. 2005).

The term "multiplex" refers to amplification with more than one set of primers, or the amplification of more than one polymorphism site in a single reaction.

In another embodiment, the method for detecting at least one SNP of the present invention is performed by an allele-specific amplification through real time PCR.

An "allele specific amplification PCR" or "amplification refractory mutation system (ARMS)" or "allele-specific PCR" or "PCR amplification of specific alleles (PASA)" is an amplification strategy in which a polymerase chain reaction (PCR) primer is designed in such a way that it is able to discriminate among templates that differ by a single nucleotide residue. Thus, an ARMS primer can be designed to amplify a specific member of a multi-allelic system while remaining refractory to amplification of another allele that may differ by as little as a single base from the former.

An "allele specific amplification through real time PCR" allows detecting SNPs in a very efficient way. As unlike most other methods for SNP detection it does not require preliminary amplification of the target genetic material (Newton et al., 1989; Wu et al., 1989). ASA combines amplification and detection in a single reaction, based on the discrimination of matched and mismatched primer/target sequence complexes. The increase of amplified DNA during the reaction can be monitored in real-time by the increase of a fluorescence signal caused by a dye e.g. SYBRGreen I (Wilhelm and Pingoud 2003) emitting upon binding to double-stranded DNA. The match case comprises a correct Watson-Crick base pair at the 3'-primer end, whereas the mismatch case features a non-canonical base pair. The mismatch should result in less efficient or, at best, no product amplification (Wu et al., 1989; Germer and Higuchi 1999; Germer, Holland and Higuchi 2000; Guo, Liu and Smith 1997; Ishikawa et al., 1995; Shively et al., 2003; Wilhelm et al., 2002). The in real-time followed ASA reflects this with a delayed or absent fluorescence signal for the mismatch case. In SNP diagnostics this provides information about the absence or presence of a SNP. In one embodiment, one allelic primer can have a 30-nucleotide overhanging sequence at its 5' end. In another embodiment, both alleles can be detected in the same reaction e.g. according to their different melting temperatures.

In another embodiment, the method for detecting at least one SNP of the present invention is performed by tetra-primer amplification-refractory mutation system PCR.

A "tetra-primer-amplification-refractory mutation system PCR" or "T-ARMS-PCR" amplifies both wild-type and mutant alleles, together with a control fragment, in a single tube PCR reaction. A non-allele-specific control amplicon is amplified by 2 common (outer) primers flanking the mutation region. Two allele-specific (inner) primers are designed in opposite orientation to the common primers and, in combination with the common primers, can simultaneously amplify both the wild-type and the mutant amplicons. As a result, the 2 allele-specific amplicons have different lengths and can be easily separated by standard gel electrophoresis because the mutation is asymmetrically located with respect to the common (outer) primers. The control amplicon provides an internal control with respect to false negatives as well as amplification failure and at least 1 of the 2 allele-specific amplicons are always present in T-ARMS-PCR (Piccoli et al., 2006).

In another embodiment, the method for detecting at least one methylated nucleotide or the method for detecting at least one SNP of the present invention is performed by isothermal amplification.

An "isothermal amplification" means that an amplification of a nucleic acid is achieved at lower temperatures, without being dependent on thermocyclers, preferably the temperature does not need to change during amplification. Different techniques have been developed, which are known to the skilled artesian (see e.g. Gill and Ghaemi 2008). Examples of isothermal amplification include transcription mediated amplification (TMA), nucleic acid based amplification (NASBA), signal mediated amplification of RNA technology (SMART), strand displacement amplification (SDA), loop-mediated isothermal amplification (LAMP), isothermal multiple displacement amplification (IMDA), helicase-dependent amplification (HAD), single primer isothermal amplification (SPIA). The temperature used in the isothermal amplification can be between room temperature (22-24° C.) to about 65° C., or it can be between about 60-65° C., between 45-50° C., between 37-42° C. or room temperature of 22-24° C. The product that results from the isothermal amplification can be detected by gel electrophoresis, ELISA, ELOSA (Enzyme linked oligosorbent assay), Real-time PCR, ECL (enhanced chemiluminescence), bioanalyzer, which is a chip-based capillary electrophoresis machine to analyze RNA, DNA, and protein or turbidity. RGA and HAD are also suitable for multiplex amplification.

In another embodiment, the method for detecting at least one methylated nucleotide of the present invention is performed by PCR, preferably RT-PCR or isothermal amplification or methylation specific PCR.

A "methylation-specific PCR" or "MSP" is a method to discriminately amplify and detect a methylated region of interest e.g. in a target sequence. MSP is a widespread method used for the analysis of methylation patterns of cytosines at the C-5 position (5mC)—the most abundant DNA modification in vertebrates. Several methods for detection of DNA methylation alterations are known and are employed. The most common approaches to obtain single base resolution are based on 'bisulfite treatment' of the genomic DNA sample. By bisulfite treatment cytosine (C) is converted to uracil while 5mC remains unchanged (Hayatsu et al., 1970). In MSP, after bisulfite treatment the DNA sample is amplified by the polymerase chain reaction (PCR) while primer pairs are chosen which span the CpG site. Hereby, one primer pair is designed for unmethylated DNA and the other primer pair for methylated DNA. Due to conversion of C into uracil, a mismatched primer prevents efficient PCR amplification and, optimally, only amplification from methylated DNA will occur (Kristensen, Hansen 2009).

Thus, in one embodiment, the target sequence is a DNA sequence that has been treated with bisulfite. In another embodiment, the target sequence comprises at least one "U" nucleotide. In another embodiment, the DNA polymerase is used to detect the presence or absence of an U-nucleotide.

In another embodiment, the method for detecting at least one methylated nucleotide or the method for detecting at least one SNP of the present invention further comprises comparing an obtained result to a control sample or control value.

Suitable controls are known to the skilled artesian (see e.g. Arya et al., 2005). For example, housekeeping genes can be used for normalization. Other controls can be general standards known for the specific techniques used. The control can be a negative or positive control for the reaction itself and/or a template serving as a positive or negative control.

Positive controls are needed for the verification of negative amplification results and the positive control reaction should contain the same components as the sample but include a template that is certain to amplify if the reaction goes as planned. This could be an external positive control, which is a separate sample containing the control template. Such external control reactions can help detect when a reaction fails due to cycler or reaction component problems or when an inhibitor is suppressing the reaction. Alternatively, an internal positive control (IPC) can be used. To run a reaction with an IPC, the template and primers for the control target are included in the reaction along with those for the target of interest. The control target should of course be easily distinguished (by electrophoretic migration or Tm) from the target of interest. IPCs are useful because they can pinpoint problems that are intrinsic to the sample reaction. In one embodiment, the control is a internal positive control or external positive control. In another embodiment, the control is a external control. In another embodiment, the control is an internal control. For example, a negative control can be a sample, in which no reverse transcriptase, no template or no dNTPs are added. Further possible controls are also known to the person skilled in the art (see e.g. Lion (2001) Current recommendations for positive controls in RT-PCR assays Volume 15, Number 7, Pages 1033-1037).

For example a control may be a template with a particular region of interest. The control can also be a template without a particular region of interest. The method also includes 1, 2, 3, 4, 5, or more controls. In one embodiment, one control comprises a particular region of interest, while a second control does not.

A control value can be a predetermined value, which repeatedly can be observed under specific experimental setups. Thus, a template can be analyzed with regard to such a predetermined value or control value.

Also, the present invention relates to the use of a DNA polymerase of the present invention, in the presence of a dye that binds to double stranded DNA at a concentration of 10×-60× e.g., SYBRGreenI.

A "dye that binds to double stranded DNA" or "double strand specific dye" is usable when it has (much) higher fluorescence when bound to double-stranded DNA compared to the unbound state.

Examples for such a dye include SOYTO-9, SOYTO-13, SOYTO-16, SOYTO-60, SOYTO-64, SYTO-82, ethidium bromide, SYTOX Orange, TO-PRO-1, SYBR Green I or TO-PRO-3, EvaGreen. These dyes, except for ethidium bromide and EvaGreen (Quiagen), have been tested in real time applications (see Gudnason et al., 2007). In one embodiment, the dye that binds to double stranded DNA is SYBR Green I, SYTO-13 or SYTO-82. In a particular embodiment, the dye that binds to double stranded DNA is SYBR Green I.

The dye that binds to the double stranded DNA can be present in a concentration of 10×-60×, preferably 15×-55×, preferably 20×-50×, particularly preferred 25×-45×, more particularly preferred 27×-40×, even more particularly preferred 30×-35×. In one embodiment, the dye that binds to the double stranded DNA is present at a concentration of 30×. A concentration such as 10×-60× as used in connection with the concentration of a dye, preferably SYBRGreenI, means the use of a dye in a 10×-60× concentration with respect to the recommendation given by the manufacturer. For example if the manufacturer recommends the use of the dye in 0.5×-1× concentration for a wildtype polymerase e.g. the polymerases shown in SEQ ID NO: 1 and/or SEQ ID NO: 2, then said dye can be used in a concentration of 10×-60×. Preferably, the recommendation given by the manufacturer refers to the recommendation for the concentration of the dye for staining nucleic acid gels. Therefore, the invention also envisages the use of SYBRGreen I from the manufacturer Life Technologies Corporation (catalogue number S-7585 SYBR® Green I Nucleic Acid Gel stain; http://www.lifetechnologies.com and more specifically http://www.lifetechnologies.com/order/catalog/product/S7585?CID=search-s7585). This SYBRGreen I can be used in a 1:10000 dilution of the 10000× concentrated SYBRGReen I stock solution for staining a nucleic acid gel. The DNA polymerases of the present invention can then be used in the presence of a concentration of 10×-60× of this SYBRGreen I.

The present invention further relates to the use of DNA polymerase of the present invention in the presence of blood.

The term "blood" is a bodily fluid in animals that delivers necessary substances such as nutrients and oxygen to the cells and transports metabolic waste products away from those same cells. In vertebrates, it is composed of blood cells suspended in blood plasma. Plasma, which constitutes 55% of blood fluid, is mostly water (92% by volume), and blood cells themselves. The blood cells are mainly red blood cells (also called RBCs or erythrocytes) and white blood cells, including leukocytes and platelets (thrombocytes). Blood is circulated around the body through blood vessels.

Thus, in one embodiment, the blood is plasma. In another embodiment, blood includes blood cells. In another embodiment, blood includes red blood cells. In another embodiment, blood includes leukocytes. In another embodiment, blood includes thrombocytes.

In one embodiment, the DNA polymerase is used in the presence of 0.2% v/v to 20% v/v blood. In one embodiment, the DNA polymerase is used in the presence of 0.5% v/v to 15% v/v blood. In one embodiment, the DNA polymerase is used in the presence of 1% v/v to 10% v/v blood. In another embodiment, 0,5 µl blood are dried and then 10 µl of a suitable solution is added. In another embodiment, the sample containing blood is denatured before amplification starts. In another embodiment, the blood is whole blood including plasma and blood cells.

The present invention further relates to the use of DNA polymerase of the present invention at a concentration of 25 nM-600 nM.

In one embodiment, relates to the use of DNA polymerase of the present invention at a concentration of 30 nM-500 nM.

In another embodiment, relates to the use of DNA polymerase of the present invention at a concentration of 35 nM-400 nM.

In another embodiment, relates to the use of DNA polymerase of the present invention at a concentration of 40 nM-300 nM.

In another embodiment, relates to the use of DNA polymerase of the present invention at a concentration of 45 nM-200 nM.

In another embodiment, relates to the use of DNA polymerase of the present invention at a concentration of 50 nM-100 nM.

In another embodiment, relates to the use of DNA polymerase of the present invention at a concentration of 100 nM.

In addition, the present invention also relates to a nucleic acid molecule encoding for the DNA polymerase of the present invention.

In addition, the present invention also relates to a vector comprising a nucleic acid molecule encoding for the DNA polymerase of present invention.

Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. As discussed in further details below, a cloning vector was used to isolate individual sequences of DNA. Relevant sequences can be transferred into expression vectors where expression of a particular polypeptide is required. Typical cloning vectors include pBluescript SK, pGEM, pUC9, pBR322 and pGBT9. Typical expression vectors include pTRE, pCALn-EK, pESP-1, pOP13CAT.

Preferably said vector comprises a nucleic acid sequence, which is a regulatory sequence operably linked to the nucleic acid encoding for the DNA polymerase of the present invention.

The term "regulatory sequence" refers to DNA sequences, which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

Thus, the recited vector is preferably an expression vector. An "expression vector" is a construct that can be used to transform a selected host and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the $P_L$, lac, trp or tac promoter in E. coli, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells.

Beside elements, which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the recited nucleic acid sequence and are well known in the art; see also the appended Examples. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (In-vitrogene), pEF-DHFR, pEF-ADA or pEF-neo (Mack et al. PNAS (1995) 92, 7021-7025 and Raum et al. Cancer Immunol Immunother (2001) 50(3), 141-150) or pSPORT1 (GIBCO BRL).

Preferably, the expression control sequences will be eukaryotic promoter systems in vectors capable of transforming of transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the polypeptide of the invention may follow; see, e.g., the appended examples.

Additional regulatory elements may include transcriptional as well as translational enhancers. Advantageously, the above-described vectors of the invention comprise a selectable and/or scorable marker.

Selectable marker genes useful for the selection of transformed cells and, e.g., plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149); npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from Aspergillus terreus which confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, Pl. Sci. 116

(1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule can be used alone or as part of a vector to express the polypeptide of the invention in cells, for, e.g., purification but also for gene therapy purposes. The nucleic acid molecules or vectors containing the DNA sequence(s) encoding any one of the above described polypeptide of the invention is introduced into the cells which in turn produce the polypeptide of interest.

The recited nucleic acid molecules and vectors may be designed for direct introduction or for introduction via liposomes, or viral vectors (e.g., adenoviral, retroviral) into the cell. Preferably, said cell is a germ line cell, embryonic cell, or egg cell or derived there from, most preferably said cell is a stem cell. An example for an embryonic stem cell can be, inter alia, a stem cell as described in Nagy, Proc. Natl. Acad. Sci. USA 90 (1993), 8424-8428.

The invention also provides for a host comprising a nucleic acid encoding for a DNA polymerase of the present invention. Said host may be produced by introducing the above described vector of the invention or the above described nucleic acid molecule of the invention into the host. The presence of at least one vector or at least one nucleic acid molecule in the host may mediate the expression of the DNA polymerase of the present invention.

The described nucleic acid molecule or vector of the invention, which is introduced in the host may either integrate into the genome of the host or it may be maintained extrachromosomally.

The host can be any prokaryote or eukaryotic cell.

The term "prokaryote" is meant to include all bacteria, which can be transformed or transfected with DNA or RNA molecules for the expression of a protein of the invention. Prokaryotic hosts may include gram negative as well as gram positive bacteria such as, for example, *E. coli* (particularly XI—blue, DH5α, BI21, M15 [pREP4]], SG13005 [pREP4], BL21 (DE3) pLysS), *Holomonos elongate, Coulobocter* sp., *Holobocterium holobium, S. typhimurium, Serratia marcescens* and *Bacillus subtilis*. The term "eukaryotic" is meant to include yeast, higher plant, insect and preferably mammalian cells. Depending upon the host employed in a recombinant production procedure, the protein encoded by the polynucleotide of the present invention may be glycosylated or may be non-glycosylated. Especially preferred is the use of a plasmid or a virus containing the coding sequence of the polypeptide of the invention and genetically fused thereto an N-terminal FLAG-tag and/or C-terminal His-tag. Preferably, the length of said FLAG-tag is about 4 to 8 amino acids, most preferably 8 amino acids. An above described polynucleotide can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, loc cit.).

In one embodiment, the host is a bacterium or an insect, fungal, plant or animal cell.

Also envisaged that the recited host may be a mammalian cell. Particularly preferred host cells comprise CHO cells, COS cells, myeloma cell lines like SP2/0 or NS/0. As illustrated in the appended examples, particularly preferred are CHO-cells as hosts.

In one embodiment said host cell is a human cell or human cell line, e.g. per.c6 (Kroos, Biotechnol. Prog., 2003, 19:163-168).

Another embodiment the invention relates to host cells, in particular prokaryotic or eukaryotic cells, genetically engineered with the (mutant) nucleic acids or vectors of the present invention or which are obtainable by a method for producing genetically engineered host cells, as well as to cells derived from such transformed host cells. Preferably, the host cell of the present invention is a bacterial, yeast, fungus, plant or animal cell, with a human cell being particularly preferred.

The host cell of the present invention also comprises cell extracts from a host cell or host cell culture.

In a further embodiment, the present invention thus relates to a process for the production of a DNA polymerase of the invention, said process comprising culturing a host of the invention under conditions allowing the expression of the DNA polymerase of the invention and recovering the produced polypeptide from the culture.

The transformed hosts can be grown in fermentors and cultured according to techniques known in the art to achieve optimal cell growth. The polypeptide of the invention can then be isolated from the growth medium, cellular lysates, or cellular membrane fractions. The isolation and purification of the, e.g., microbially expressed polypeptides of the invention may be by any conventional means such as, for example, preparative chromatographic separations and immunological separations such as those involving the use of monoclonal or polyclonal antibodies directed, e.g., against a tag of the polypeptide of the invention or as described in the appended examples.

The conditions for the culturing of a host, which allow the expression, are known in the art to depend on the host system and the expression system/vector used in such process. The parameters to be modified in order to achieve conditions allowing the expression of a recombinant polypeptide are known in the art. Thus, suitable conditions can be determined by the person skilled in the art in the absence of further inventive input.

Once expressed, the polypeptide of the invention can be purified according to standard procedures of the art, including ammonium sulfate precipitation, affinity columns, column chromatography, gel electrophoresis and the like; see, Scopes, "Protein Purification", Springer-publisher (Verlag), N.Y. (1982). Substantially pure polypeptides of at least about 90 to 95% homogeneity are preferred, and 98 to 99% or more homogeneity are most preferred, for pharmaceutical uses. Once purified, partially or to homogeneity as desired, the polypeptide of the invention may then be used therapeutically (including extracorporally) or in developing and performing assay procedures. Furthermore, examples for methods for the recovery of the polypeptide of the invention from a culture are described in detail in the appended examples. In one embodiment, the DNA polymerase of the present invention is purified. In another embodiment the DNA polymerase of the present invention is purified, while retaining the PCR reactivity compared to the PCR activity before the purification. In another embodiment the DNA polymerase of the present invention retains the PCR reactivity upon long term storage of six months at −20° C. when compared to the PCR activity before the storage.

The present invention further relates to a kit comprising the DNA polymerase of the present invention.

The present invention also relates to a kit-of-parts comprising the DNA polymerase of the present invention.

The present invention relates to a kit or kit-of-parts comprising at least one DNA polymerase of the present invention and optionally means to purify or enrich the DNA polymerase of the present invention and/or means to wash the DNA polymerase of the present invention; and/or means to store the polymerase of the present invention. The DNA polymerase of the present invention and the additional means are thereby preferably packaged together in one sealed package or kit.

Parts of the kit (or the "kit of parts") of the invention can be packaged individually in vials or bottles or in combination in containers or multicontainer units. The manufacture of the kits follows preferably standard procedures which are known to the person skilled in the art.

The kit or kit-of-parts may also comprise written instructions for the use of the DNA polymerase of the present invention in accordance with the methods and uses of the present invention. Said kit or kit-of-parts may further comprise a label or imprint indicating that the contents can be used for the augmentation of the DNA polymerase of the present invention and/or for using the DNA polymerase of the present invention.

It is also envisaged that the kit or kit-of-parts of the present invention, further comprises for example buffers, vials, control(s), stabilizer(s), written instructions which aid the skilled person in the preparation or use of the DNA polymerase of the present invention.

The kit or kit-of-parts of the present invention may comprise one or more container(s), optionally with a label. Suitable containers include, for example, bottles, vials, and test tubes. The containers may be formed from a variety of materials such as glass or plastic, and are preferably sterilized. The container holds a composition having an active ingredient or comprising a buffer which is effective for the detection of a SNP or methylation status of a template. Further container may hold suitable amplification primers (for example PCR-primers) which allow the specific amplification of a specific template. It is also envisaged that containers are included which hold diverse buffers, for example amplification buffers, and/or buffers for the formation of e.g. primer/template complexes etc. The active agent in the composition is preferably a DNA polymerase of the present invention, a positive control, a negative control etc. The kit may further comprise amplification primer pairs for the specific amplification of genomic DNA. The label on the container indicates that the composition is used for the detection of for example a specific SNP like the SNP Factor II G20210A and/or for the amplification of the human genomic DNA, and may also indicate directions for in vitro use or methods, such as those described above.

The DNA polymerase can also be present in a lyophilized state within the kit or the kit-of-parts of the present invention.

The present invention is further directed to kits or kit-of-parts useful in the methods and uses of the invention. The kit contains reagents for the detection and/or measurement of SNP or the methylation status of a template.

In one embodiment, the kit or kit-of-parts of the present invention further comprises the DNA polymerase of the present invention and at least one matched primer and/or at least one mismatched primer, wherein said primers hybridize to a target sequence, and
wherein the mismatched primer comprises a non-canonical nucleotide in a position of up to seven bases from its 3' end in relation to a target sequence to which it hybridizes.

For example the primer can be a scorpion primer or a lux primer.

The kit or kit-of-parts of the present invention can comprise 1, 2, 3, 4, 5, 6, 7, 8, 9, 10, 11, 12, 20, 30, 40, 50 or more primers. The primer can be both matched and mismatched. Also envisaged are kits or kit-of-parts comprising matched primers. Also envisaged are kits or kit-of-parts comprising mismatched primers. Also envisaged are kits or kit-of-parts comprising both matched and mismatched primers.

In one embodiment, the kit or kit-of-parts of the present invention can further comprise nucleoside triphosphates. For example only dNTPs or rNTPs may be present kit or kit-of-parts of the present invention. It can also be that 1, 2 or 3 different types of dNTPs are present kit or kit-of-parts of the present invention. It can also be that 1, 2 or 3 different types of rNTPs are present kit or kit-of-parts of the present invention.

In one embodiment, the kit or kit-of-parts of the present invention further optionally comprises
a) one or more buffer(s);
b) reagents for quantifications, particularly reagents that bind to double stranded DNA particularly SYBR-GreenI;
c) polymerase-blocking antibodies, in particular TaqBlock;
d) one or more control values or control sequences;
e) one or more templates.

In one embodiment, the buffer comprised in the kit or kit-of-part comprises a buffer, in which the DNA polymerase of the present invention can perform an amplification of a template.

In one embodiment, the buffer comprised in the kit or kit-of-part comprises a buffer, suitable for the formation of primer/template complexes.

In one embodiment, the buffer comprised in the kit or kit-of-part comprises a buffer, suitable for the storage of the DNA polymerase of the present invention.

The kit or kit-of-parts of the present invention further optionally comprise reagents for quantifications. The reagent for quantification includes dyes that bind to double stranded DNA, as disclosed herein.

The kit or kit-of-parts of the present invention further optionally comprises polymerase-blocking antibodies, in particular TaqBlock.

The kit or kit-of-parts of the present invention further optionally comprises one or more control values or control sequences, such as the control values or control sequences as described herein.

The kit or kit-of-parts of the present invention further optionally comprises one or more templates, such as the templates as described herein.

The kit or kit-of-parts of the present invention further optionally comprises the nucleic acid molecule of the present invention.

The kit or kit-of-parts of the present invention further optionally comprises the vector of the present invention.

The kit or kit-of-parts of the present invention further optionally comprises the host cell of the present invention.

In one embodiment, the kit or kit-of-parts of the present invention comprises the DNA polymerase of the present invention and the matched and the mismatched primer.

In another embodiment, the kit or kit-of-parts of the present invention comprises the DNA polymerase of the present invention, the matched and the mismatched primer and one buffer suitable for amplification.

In another embodiment, the kit or kit-of-parts of the present invention comprises the DNA polymerase of the present invention, the matched and the mismatched primer, one buffer suitable for amplification and a control sequence.
Sequences
The following table and sequences below provide an overview on the sequences used herein:

| | |
|---|---|
| SEQ ID NO: 1 | Taq Polymerase (Taq) |
| SEQ ID NO: 2 | KlenTaq (KTQ), Klenow fragment of the Taq Polymerase of SEQ ID NO: 1 |
| SEQ ID NO: 3 | Taq R487V |
| SEQ ID NO: 4 | Taq R487H |
| SEQ ID NO: 5 | Taq K508W |
| SEQ ID NO: 6 | Taq K508Y |
| SEQ ID NO: 7 | Taq R536K |
| SEQ ID NO: 8 | Taq R536L |
| SEQ ID NO: 9 | Taq R587I |
| SEQ ID NO: 10 | Taq R587K |
| SEQ ID NO: 11 | Taq R660V |
| SEQ ID NO: 12 | Taq R660T |
| SEQ ID NO: 13 | Taq VL22: K508Y, R587K, R660T |
| SEQ ID NO: 14 | KTQ R210V (R487V in Taq sequence) |
| SEQ ID NO: 15 | KTQ R210H (R487H in Taq sequence) |
| SEQ ID NO: 16 | KTQ K231W (K508W in Taq sequence) |
| SEQ ID NO: 17 | KTQ K231Y (K508Y in Taq sequence) |
| SEQ ID NO: 18 | KTQ R259K (R536K in Taq sequence) |
| SEQ ID NO: 19 | KTQ R259L (R536L in Taq sequence) |
| SEQ ID NO: 20 | KTQ R310L (R587L in Taq sequence) |
| SEQ ID NO: 21 | KTQ R310I (R587I in Taq sequence) |
| SEQ ID NO: 22 | KTQ R383V (R660V in Taq sequence) |
| SEQ ID NO: 23 | KTQ R383T (R660T in Taq sequence) |
| SEQ ID NO: 24 | KTQVL22: K231Y, R310K, R383T (K508Y, R587K, R660T in Taq sequence) |
| SEQ ID NO: 25 | 5'-d(CGT TGG TCC TGA AGG AGG AT)-3'      F20-for 20 nt |
| SEQ ID NO: 26 | 5'-d(CGC GCA GCA CGC GCC GCC GT)-3'      F20-rev 20 nt |
| SEQ ID NO: 27 | 5' d(CCG TCA GCT GTG CCG TCG CGC AGC ACG CGC CGC   F90A 90 nt<br>CGT GGA CAG AGG ACT GCA GAA AAT CAA CCT ATC CTC<br>CTT CAG GAC CAA CGT ACA GAG)-3'] |
| SEQ ID NO: 28 | 5' d(CCG TCA GCT GTG CCG TCG CGC AGC ACG CGC CGC   F90G 90 nt<br>CGT GGA CAG AGG ACT GCA GAA AAT CAA CCT GTC CTC<br>CTT CAG GAC CAA CGT ACA GAG)-3' |
| SEQ ID NO: 29 | 5'-[32P]-d(CGT TGG TCC TGA AGG AGG AT)-3'  DNA primer 20 nt |
| SEQ ID NO: 30 | 5'-d(AAA TCA ACC TAT CCT CCT TCA GGA CCA ACG TAC)-template<br>3'                                           F33A 33 nt |
| SEQ ID NO: 31 | 5'-d(AAA TCA ACC TGT CCT CCT TCA GGA CCA ACG TAC)-F33G 33 nt<br>3' |
| SEQ ID NO: 32 | 5'-d(CGTTGGTCCTGAAGGAGGAT)-3'             F20-for 20 nt |
| SEQ ID NO: 33 | 5'-d(CGCGCAGCACGCGCCGCCGT)-3'             F20-rev |
| SEQ ID NO: 34 | 5'-d(CCGTCAGCTGTGCCGTCGCGCAGCACGCGCCGCCGTGGACA  F90A 90 nt<br>GAGGACTGCAGAAAATCAACCTATCCTCCTTCAGGACCAACGT<br>ACAGAG)-3' |
| SEQ ID NO: 35 | 5'-d(CCGTCAGCTGTGCCGTCGCGCAGCACGCG           F90G 90 nt<br>CCGCCGTGGACAGAGGACTGCAGAAAATCAACCTGTCCTCCTT<br>CAGGACCAAC GTACAGAG)-3' |

| | | |
|---|---|---|
| SEQ ID NO: 36 | 5' d(CCC AAT AAA AGT GAC TCT CAG CG) 3' | F2forG 23 nt |
| SEQ ID NO: 37 | 5' d(CCC AAT AAA AGT GAC TCT CAG CA) 3' | F2forA 23 nt |
| SEQ ID NO: 38 | 5' d(CCA GAG AGC TGC CCA TGA AT) 3' | reverse Primer F2rev 20 nt |
| SEQ ID NO: 39 | 5'-d(CAGATCCCTGGACAGGCG)-3' | F5forG 18 nt |
| SEQ ID NO: 40 | 5'-d(CAGATCCCTGGACAGGCA)-3' | F5forA 18 nt |
| SEQ ID NO: 41 | 5'-d(GGAGACCTAACATGTTCTAGCCA)-3' | reverse Primer F5rev 23 nt |
| SEQ ID NO: 42 | 5' d(GCG CGA TTC GTT GTT TAT TAG TTA TTA TGT) 3' | forward primer MSPSEPT9con Forw 30 nt |
| SEQ ID NO: 43 | 5' d(TCG AAA TCC GAA ATA ATC CCA TCC AAC TAC G) 3' | reverse Primers MSPSEPT9con Rev G 31 nt |
| SEQ ID NO: 44 | 5' d(TCG AAA TCC GAA ATA ATC CCA TCC AAC TAC A)-3' | MSPSEPT9con Rev A 31 nt |
| SEQ ID NO: 45 | 5' d(TTC GCG CGA TTC GTT GTT TAT TAG TTA TTA TGT CGG ATT TCG CGG TTA ACG 5mCGT AGT TGG ATG GGA TTA TTT CGG ATT TCG AAG G) 3'] | Temp Sept9 Methylated 5mC 85 nt |
| SEQ ID NO: 46 | 5' d(TTC GCG CGA TTC GTT GTT TAT TAG TTA TTA TGT CGG ATT TCG CGG TTA ACG UGT AGT TGG ATG GGA TTA TTT CGG ATT TCG AAG G)-3' | Sept9 unmethylated U 85 nt |
| SEQ ID NO: 47 | 5'-[32P]-d(CGT TGG TCC TGA AGG AGG AT)-3' | Primer P 20 nt |
| SEQ ID NO: 48 | 5'-[32P]-d(CGT TGG TCC TGA AGG AGG ATA GG)-3' | Primer P + 3 23 nt |
| SEQ ID NO: 49 | 5'[32P]-d(CGT TGG TCC TGA AGG AGG ATA GGT G)-3' | Primer P + 6 26 nt |
| SEQ ID NO: 50 | 5' d(ATC CAA CTC TCT ACG CAA TGG CAC TAG AGA CCC AAT AAA AGT GAC TCT CAG CG) 3' | F2forGlang 53 nt |

SEQ ID NO: 1 - Taq
MRGMLPLFEPKGRVLLVDGHHLAYRTFHALKGLTTSRGEPVQAVYGFAKSLLKALKEDGD

AVIVVFDAKAPSFRHEAYGGYKAGRAPTPEDFPRQLALIKELVDLLGLARLEVPGYEADD

VLASLAKKAEKEGYEVRILTADKDLYQLLSDRIHVLHPEGYLITPAWLWEKYGLRPDQWA

DYRALTGDESDNLPGVKGIGEKTARKLLEEWGSLEALLKNLDRLKPAIREKILAHMDDLK

LSWDLAKVRTDLPLEVDFAKRREPDRERLRAFLERLEFGSLLHEFGLLESPKALEEAPWP

PPEGAFVGFVLSRKEPMWADLLALAAARGGRVHRAPEPYKALRDLKEARGLLAKDLSVLA

LREGLGLPPGDDPMLLAYLLDPSNTTPEGVARRYGGEWTEEAGERAALSERLFANLWGRL

EGEERLLWLYREVERPLSAVLAHMEATGVRLDVAYLRALSLEVAEEIARLEAEVFRLAGH

PFNLNSRDQLERVLFDELGLPAIGKTEKTGKRSTSAAVLEALREAHPIVEKILQYRELTK

LKSTYIDPLPDLIHPRTGRLHTRFNQTATATGRLSSSDPNLQNIPVRTPLGQRIRRAFIA

EEGWLLVALDYSQIELRVLAHLSGDENLIRVFQEGRDIHTETASWMFGVPREAVDPLMRR

AAKTINFGVLYGMSAHRLSQELAIPYEEAQAFIERYFQSFPKVRAWIEKTLEEGRRRGYV

ETLFGRRRYVPDLEARVKSVREAAERMAFNMPVQGTAADLMKLAMVKLFPRLEEMGARML

LQVHDELVLEAPKERAEAVARLAKEVMEGVYPLAVPLEVEVGIGEDWLSAKE

SEQ ID NO: 2 - KTQ wt:
MRGSHHHHHHTDPHAALEEAPWPPPEGAFVGFVLSRKEPMWADLLALAAARGGRVHRAPE

PYKALRDLKEARGLLAKDLSVLALREGLGLPPGDDPMLLAYLLDPSNTTPEGVARRYGGE

-continued

WTEEAGERAALSERLFANLWGRLEGEERLLWLYREVERPLSAVLAHMEATGVRLDVAYLR

ALSLEVAEEIARLEAEVERLAGHPFNLNSRDQLERVLFDELGLPAIGKTEKTGKRSTSAA

VLEALREAHPIVEKILQYRELTKLKSTYIDPLPDLIHPRTGRLHTRFNQTATATGRLSSS

DPNLQNIPVRTPLGQRIRRAFIAEEGWLLVALDYSQIELRVAHLSGDENLIRVFQEGRD

IHTETASWMFGVPREAVDPLMRRAAKTINFGVLYGMSAHRLSQELAIPYEEAQAFIERYF

QSFPKVRAWIEKTLEEGRRRGYVETLFGRRRYVPDLEARVKSVREAAERMAFNMPVQGTA

ADLMKLAMVKLFPRLEEMGARMLLQVHDELVLEAPKERAEAVARLAKEVMEGVYPLAVPL

EVEVGIGEDWLSAKEKA

SEQ ID NO: 3 - Taq R487V:
MRGMLPLFEPKGRVLLVDGHHLAYRTFHALKGLTTSRGEPVQAVYGFAKSLLKALKEDGD

AVIVVFDAKAPSFRHEAYGGYKAGRAPTPEDFPRQLALIKELVDLLGLARLEVPGYEADD

VLASLAKKAEKEGYEVRILTADKDLYQLLSDRIHVLHPEGYLITPAWLWEKYGLRPDQWA

DYRALTGDESDNLPGVKGIGEKTARKLLEEWGSLEALLKNLDRLKPAIREKILAHMDDLK

LSWDLAKVRTDLPLEVDFAKRREPDRERLRAFLERLEFGSLLHEFGLLESPKALEEAPWP

PPEGAFVGFVLSRKEPMWADLLALAAARGGRVHRAPEPYKALRDLKEARGLLAKDLSVLA

LREGLGLPPGDDPMLLAYLLDPSNTTPEGVARRYGGEWTEEAGERAALSERLFANLWGRL

EGEERLLWLYREVERPLSAVLAHMEATGVRLDVAYLRALSLEVAEEIARLEAEVFRLAGH

PFNLNSRDQLERVLFDELGLPAIGKTEKTGKRSTSAAVLEALREAHPIVEKILQYRELTK

LKSTYIDPLPDLIHPRTGRLHTRFNQTATATGRLSSSDPNLQNIPVRTPLGQRIRRAFIA

EEGWLLVALDYSQIELRVAHLSGDENLIRVFQEGRDIHTETASWMFGVPREAVDPLMRR

AAKTINFGVLYGMSAHRLSQELAIPYEEAQAFIERYFQSFPKVRAWIEKTLEEGRRRGYV

ETLFGRRRYVPDLEARVKSVREAAERMAFNMPVQGTAADLMKLAMVKLFPRLEEMGARML

LQVHDELVLEAPKERAEAVARLAKEVMEGVYPLAVPLEVEVGIGEDWLSAKE

SEQ ID NO: 4 - Taq R487H:
MRGMLPLFEPKGRVLLVDGHHLAYRTFHALKGLTTSRGEPVQAVYGFAKSLLKALKEDGD

AVIVVFDAKAPSFRHEAYGGYKAGRAPTPEDFPRQLALIKELVDLLGLARLEVPGYEADD

VLASLAKKAEKEGYEVRILTADKDLYQLLSDRIHVLHPEGYLITPAWLWEKYGLRPDQWA

DYRALTGDESDNLPGVKGIGEKTARKLLEEWGSLEALLKNLDRLKPAIREKILAHMDDLK

LSWDLAKVRTDLPLEVDFAKRREPDRERLRAFLERLEFGSLLHEFGLLESPKALEEAPWP

PPEGAFVGFVLSRKEPMWADLLALAAARGGRVHRAPEPYKALRDLKEARGLLAKDLSVLA

LREGLGLPPGDDPMLLAYLLDPSNTTPEGVARRYGGEWTEEAGERAALSERLFANLWGRL

EGEERLLWLYREVERPLSAVLAHMEATGVRLDVAYLRALSLEVAEEIARLEAEVFRLAGH

PFNLNSRDQLERVLFDELGLPAIGKTEKTGKRSTSAAVLEALREAHPIVEKILQYRELTK

LKSTYIDPLPDLIHPRTGRLHTRFNQTATATGRLSSSDPNLQNIPVRTPLGQRIRRAFIA

EEGWLLVALDYSQIELRVAHLSGDENLIRVFQEGRDIHTETASWMFGVPREAVDPLMRR

AAKTINFGVLYGMSAHRLSQELAIPYEEAQAFIERYFQSFPKVRAWIEKTLEEGRRRGYV

ETLFGRRRYVPDLEARVKSVREAAERMAFNMPVQGTAADLMKLAMVKLFPRLEEMGARML

LQVHDELVLEAPKERAEAVARLAKEVMEGVYPLAVPLEVEVGIGEDWLSAKE

SEQ ID NO: 5 - Taq K508W:
MRGMLPLFEPKGRVLLVDGHHLAYRTFHALKGLTTSRGEPVQAVYGFAKSLLKALKEDGD

AVIVVFDAKAPSFRHEAYGGYKAGRAPTPEDFPRQLALIKELVDLLGLARLEVPGYEADD

VLASLAKKAEKEGYEVRILTADKDLYQLLSDRIHVLHPEGYLITPAWLWEKYGLRPDQWA

DYRALTGDESDNLPGVKGIGEKTARKLLEEWGSLEALLKNLDRLKPAIREKILAHMDDLK
LSWDLAKVRTDLPLEVDFAKRREPDRERLRAFLERLEFGSLLHEFGLLESPKALEEAPWP
PPEGAFVGFVLSRKEPMWADLLALAAARGGRVHRAPEPYKALRDLKEARGLLAKDLSVLA
LREGLGLPPGDDPMLLAYLLDPSNTTPEGVARRYGGEWTEEAGERAALSERLFANLWGRL
EGEERLLWLYREVERPLSAVLAHMEATGVRLDVAYLRALSLEVAEEIARLEAEVFRLAGH
PFNLNSRDQLERVLFDELGLPAIGKTE*TGKRSTSAAVLEALREAHPIVEKILQYRELTK
LKSTYIDPLPDLIHPRTGRLHTRFNQTATATGRLSSSDPNLQNIPVRTPLGQRIRRAFIA
EEGWLLVALDYSQIELRVLAHLSGDENLIRVFQEGRDIHTETASWMFGVPREAVDPLMRR
AAKTINFGVLYGMSAHRLSQELAIPYEEAQAFIERYFQSFPKVRAWIEKTLEEGRRRGYV
ETLFGRRRYVPDLEARVKSVREAAERMAFNMPVQGTAADLMKLAMVKLFPRLEEMGARML
LQVHDELVLEAPKERAEAVARLAKEVMEGVYPLAVPLEVEVGIGEDWLSAKE

SEQ ID NO: 6 - Taq K508Y:
MRGMLPLFEPKGRVLLVDGHHLAYRTFHALKGLTTSRGEPVQAVYGFAKSLLKALKEDGD
AVIVVFDAKAPSFRHEAYGGYKAGRAPTPEDFPRQLALIKELVDLLGLARLEVPGYEADD
VLASLAKKAEKEGYEVRILTADKDLYQLLSDRIHVLHPEGYLITPAWLWEKYGLRPDQWA
DYRALTGDESDNLPGVKGIGEKTARKLLEEWGSLEALLKNLDRLKPAIREKILAHMDDLK
LSWDLAKVRTDLPLEVDFAKRREPDRERLRAFLERLEFGSLLHEFGLLESPKALEEAPWP
PPEGAFVGFVLSRKEPMWADLLALAAARGGRVHRAPEPYKALRDLKEARGLLAKDLSVLA
LREGLGLPPGDDPMLLAYLLDPSNTTPEGVARRYGGEWTEEAGERAALSERLFANLWGRL
EGEERLLWLYREVERPLSAVLAHMEATGVRLDVAYLRALSLEVAEEIARLEAEVFRLAGH
PFNLNSRDQLERVLFDELGLPAIGKTE*TGKRSTSAAVLEALREAHPIVEKILQYRELTK
LKSTYIDPLPDLIHPRTGRLHTRFNQTATATGRLSSSDPNLQNIPVRTPLGQRIRRAFIA
EEGWLLVALDYSQIELRVLAHLSGDENLIRVFQEGRDIHTETASWMFGVPREAVDPLMRR
AAKTINFGVLYGMSAHRLSQELAIPYEEAQAFIERYFQSFPKVRAWIEKTLEEGRRRGYV
ETLFGRRRYVPDLEARVKSVREAAERMAFNMPVQGTAADLMKLAMVKLFPRLEEMGARML
LQVHDELVLEAPKERAEAVARLAKEVMEGVYPLAVPLEVEVGIGEDWLSAKE

SEQ ID NO: 7 - Taq R536K:
MRGMLPLFEPKGRVLLVDGHHLAYRTFHALKGLTTSRGEPVQAVYGFAKSLLKALKEDGD
AVIVVFDAKAPSFRHEAYGGYKAGRAPTPEDFPRQLALIKELVDLLGLARLEVPGYEADD
VLASLAKKAEKEGYEVRILTADKDLYQLLSDRIHVLHPEGYLITPAWLWEKYGLRPDQWA
DYRALTGDESDNLPGVKGIGEKTARKLLEEWGSLEALLKNLDRLKPAIREKILAHMDDLK
LSWDLAKVRTDLPLEVDFAKRREPDRERLRAFLERLEFGSLLHEFGLLESPKALEEAPWP
PPEGAFVGFVLSRKEPMWADLLALAAARGGRVHRAPEPYKALRDLKEARGLLAKDLSVLA
LREGLGLPPGDDPMLLAYLLDPSNTTPEGVARRYGGEWTEEAGERAALSERLFANLWGRL
EGEERLLWLYREVERPLSAVLAHMEATGVRLDVAYLRALSLEVAEEIARLEAEVFRLAGH
PFNLNSRDQLERVLFDELGLPAIGKTEKTGKRSTSAAVLEALREAHPIVEKILQY*ELTK
LKSTYIDPLPDLIHPRTGRLHTRFNQTATATGRLSSSDPNLQNIPVRTPLGQRIRRAFIA
EEGWLLVALDYSQIELRVLAHLSGDENLIRVFQEGRDIHTETASWMFGVPREAVDPLMRR
AAKTINFGVLYGMSAHRLSQELAIPYEEAQAFIERYFQSFPKVRAWIEKTLEEGRRRGYV
ETLFGRRRYVPDLEARVKSVREAAERMAFNMPVQGTAADLMKLAMVKLFPRLEEMGARML
LQVHDELVLEAPKERAEAVARLAKEVMEGVYPLAVPLEVEVGIGEDWLSAKE

SEQ ID NO: 8 - Taq R536L:
MRGMLPLFEPKGRVLLVDGHHLAYRTFHALKGLTTSRGEPVQAVYGFAKSLLKALKEDGD
AVIVVFDAKAPSFRHEAYGGYKAGRAPTPEDFPRQLALIKELVDLLGLARLEVPGYEADD
VLASLAKKAEKEGYEVRILTADKDLYQLLSDRIHVLHPEGYLITPAWLWEKYGLRPDQWA
DYRALTGDESDNLPGVKGIGEKTARKLLEEWGSLEALLKNLDRLKPAIREKILAHMDDLK
LSWDLAKVRTDLPLEVDFAKRREPDRERLRAFLERLEFGSLLHEFGLLESPKALEEAPWP
PPEGAFVGFVLSRKEPMWADLLALAAARGGRVHRAPEPYKALRDLKEARGLLAKDLSVLA
LREGLGLPPGDDPMLLAYLLDPSNTTPEGVARRYGGEWTEEAGERAALSERLFANLWGRL
EGEERLLWLYREVERPLSAVLAHMEATGVRLDVAYLRALSLEVAEEIARLEAEVFRLAGH
PFNLNSRDQLERVLFDELGLPAIGKTEKTGKRSTSAAVLEALREAHPIVEKILQY░ELTK
LKSTYIDPLPDLIHPRTGRLHTRFNQTATATGRLSSSDPNLQNIPVRTPLGQRIRRAFIA
EEGWLLVALDYSQIELRVLAHLSGDENLIRVFQEGRDIHTETASWMFGVPREAVDPLMRR
AAKTINFGVLYGMSAHRLSQELAIPYEEAQAFIERYFQSFPKVRAWIEKTLEEGRRRGYV
ETLFGRRRYVPDLEARVKSVREAAERMAFNMPVQGTAADLMKLAMVKLFPRLEEMGARML
LQVHDELVLEAPKERAEAVARLAKEVMEGVYPLAVPLEVEVGIGEDWLSAKE

SEQ ID NO: 9 - Taq R587I:
MRGMLPLFEPKGRVLLVDGHHLAYRTFHALKGLTTSRGEPVQAVYGFAKSLLKALKEDGD
AVIVVFDAKAPSFRHEAYGGYKAGRAPTPEDFPRQLALIKELVDLLGLARLEVPGYEADD
VLASLAKKAEKEGYEVRILTADKDLYQLLSDRIHVLHPEGYLITPAWLWEKYGLRPDQWA
DYRALTGDESDNLPGVKGIGEKTARKLLEEWGSLEALLKNLDRLKPAIREKILAHMDDLK
LSWDLAKVRTDLPLEVDFAKRREPDRERLRAFLERLEFGSLLHEFGLLESPKALEEAPWP
PPEGAFVGFVLSRKEPMWADLLALAAARGGRVHRAPEPYKALRDLKEARGLLAKDLSVLA
LREGLGLPPGDDPMLLAYLLDPSNTTPEGVARRYGGEWTEEAGERAALSERLFANLWGRL
EGEERLLWLYREVERPLSAVLAHMEATGVRLDVAYLRALSLEVAEEIARLEAEVFRLAGH
PFNLNSRDQLERVLFDELGLPAIGKTEKTGKRSTSAAVLEALREAHPIVEKILQYRELTK
LKSTYIDPLPDLIHPRTGRLHTRENQTATATGRLSSSDPNLQNIP░TPLGQRIRRAFIA
EEGWLLVALDYSQIELRVLAHLSGDENLIRVFQEGRDIHTETASWMFGVPREAVDPLMRR
AAKTINFGVLYGMSAHRLSQELAIPYEEAQAFIERYFQSFPKVRAWIEKTLEEGRRRGYV
ETLFGRRRYVPDLEARVKSVREAAERMAFNMPVQGTAADLMKLAMVKLFPRLEEMGARML
LQVHDELVLEAPKERAEAVARLAKEVMEGVYPLAVPLEVEVGIGEDWLSAKE

SEQ ID NO: 10 - Taq R587K:
MRGMLPLFEPKGRVLLVDGHHLAYRTFHALKGLTTSRGEPVQAVYGFAKSLLKALKEDGD
AVIVVFDAKAPSFRHEAYGGYKAGRAPTPEDFPRQLALIKELVDLLGLARLEVPGYEADD
VLASLAKKAEKEGYEVRILTADKDLYQLLSDRIHVLHPEGYLITPAWLWEKYGLRPDQWA
DYRALTGDESDNLPGVKGIGEKTARKLLEEWGSLEALLKNLDRLKPAIREKILAHMDDLK
LSWDLAKVRTDLPLEVDFAKRREPDRERLRAFLERLEFGSLLHEFGLLESPKALEEAPWP
PPEGAFVGFVLSRKEPMWADLLALAAARGGRVHRAPEPYKALRDLKEARGLLAKDLSVLA
LREGLGLPPGDDPMLLAYLLDPSNTTPEGVARRYGGEWTEEAGERAALSERLFANLWGRL
EGEERLLWLYREVERPLSAVLAHMEATGVRLDVAYLRALSLEVAEEIARLEAEVFRLAGH
PFNLNSRDQLERVLFDELGLPAIGKTEKTGKRSTSAAVLEALREAHPIVEKILQYRELTK
LKSTYIDPLPDLIHPRTGRLHTRENQTATATGRLSSSDPNLQNIP░TPLGQRIRRAFIA
EEGWLLVALDYSQIELRVLAHLSGDENLIRVFQEGRDIHTETASWMFGVPREAVDPLMRR

-continued

AAKTINFGVLYGMSAHRLSQELAIPYEEAQAFIERYFQSFPKVRAWIEKTLEEGRRRGYV

ETLFGRRRYVPDLEARVKSVREAAERMAFNMPVQGTAADLMKLAMVKLFPRLEEMGARML

LQVHDELVLEAPKERAEAVARLAKEVMEGVYPLAVPLEVEVGIGEDWLSAKE

SEQ ID NO: 11 - Taq R660V:
MRGMLPLFEPKGRVLLVDGHHLAYRTFHALKGLTTSRGEPVQAVYGFAKSLLKALKEDGD

AVIVVFDAKAPSFRHEAYGGYKAGRAPTPEDFPRQLALIKELVDLLGLARLEVPGYEADD

VLASLAKKAEKEGYEVRILTADKDLYQLLSDRIHVLHPEGYLITPAWLWEKYGLRPDQWA

DYRALTGDESDNLPGVKGIGEKTARKLLEEWGSLEALLKNLDRLKPAIREKILAHMDDLK

LSWDLAKVRTDLPLEVDFAKRREPDRERLRAFLERLEFGSLLHEFGLLESPKALEEAPWP

PPEGAFVGFVLSRKEPMWADLLALAAARGGRVHRAPEPYKALRDLKEARGLLAKDLSVLA

LREGLGLPPGDDPMLLAYLLDPSNTTPEGVARRYGGEWTEEAGERAALSERLFANLWGRL

EGEERLLWLYREVERPLSAVLAHMEATGVRLDVAYLRALSLEVAEEIARLEAEVFRLAGH

PFNLNSRDQLERVLFDELGLPAIGKTEKTGKRSTSAAVLEALREAHPIVEKILQYRELTK

LKSTYIDPLPDLIHPRTGRLHTRFNQTATATGRLSSSDPNLQNIPVRTPLGQRIRRAFIA

EEGWLLVALDYSQIELRVAHLSGDENLIRVFQEGRDIHTETASWMFGVPREAVDPLMF

AAKTINFGVLYGMSAHRLSQELAIPYEEAQAFIERYFQSFPKVRAWIEKTLEEGRRRGYV

ETLFGRRRYVPDLEARVKSVREAAERMAFNMPVQGTAADLMKLAMVKLFPRLEEMGARML

LQVHDELVLEAPKERAEAVARLAKEVMEGVYPLAVPLEVEVGIGEDWLSAKE

SEQ ID NO: 12 - Taq R660T:
MRGMLPLFEPKGRVLLVDGHHLAYRTFHALKGLTTSRGEPVQAVYGFAKSLLKALKEDGD

AVIVVFDAKAPSFRHEAYGGYKAGRAPTPEDFPRQLALIKELVDLLGLARLEVPGYEADD

VLASLAKKAEKEGYEVRILTADKDLYQLLSDRIHVLHPEGYLITPAWLWEKYGLRPDQWA

DYRALTGDESDNLPGVKGIGEKTARKLLEEWGSLEALLKNLDRLKPAIREKILAHMDDLK

LSWDLAKVRTDLPLEVDFAKRREPDRERLRAFLERLEFGSLLHEFGLLESPKALEEAPWP

PPEGAFVGFVLSRKEPMWADLLALAAARGGRVHRAPEPYKALRDLKEARGLLAKDLSVLA

LREGLGLPPGDDPMLLAYLLDPSNTTPEGVARRYGGEWTEEAGERAALSERLFANLWGRL

EGEERLLWLYREVERPLSAVLAHMEATGVRLDVAYLRALSLEVAEEIARLEAEVERLAGH

PFNLNSRDQLERVLFDELGLPAIGKTEKTGKRSTSAAVLEALREAHPIVEKILQYRELTK

LKSTYIDPLPDLIHPRTGRLHTRFNQTATATGRLSSSDPNLQNIPVRTPLGQRIRRAFIA

EEGWLLVALDYSQIELRVAHLSGDENLIRVFQEGRDIHTETASWMFGVPREAVDPLMF

AAKTINFGVLYGMSAHRLSQELAIPYEEAQAFIERYFQSFPKVRAWIEKTLEEGRRRGYV

ETLFGRRRYVPDLEARVKSVREAAERMAFNMPVQGTAADLMKLAMVKLFPRLEEMGARML

LQVHDELVLEAPKERAEAVARLAKEVMEGVYPLAVPLEVEVGIGEDWLSAKE

SEQ ID NO: 13 - Taq VL22: K508Y, R587K, R660T:
MRGMLPLFEPKGRVLLVDGHHLAYRTFHALKGLTTSRGEPVQAVYGFAKSLLKALKEDGD

AVIVVFDAKAPSFRHEAYGGYKAGRAPTPEDFPRQLALIKELVDLLGLARLEVPGYEADD

VLASLAKKAEKEGYEVRILTADKDLYQLLSDRIHVLHPEGYLITPAWLWEKYGLRPDQWA

DYRALTGDESDNLPGVKGIGEKTARKLLEEWGSLEALLKNLDRLKPAIREKILAHMDDLK

LSWDLAKVRTDLPLEVDFAKRREPDRERLRAFLERLEFGSLLHEFGLLESPKALEEAPWP

PPEGAFVGFVLSRKEPMWADLLALAAARGGRVHRAPEPYKALRDLKEARGLLAKDLSVLA

LREGLGLPPGDDPMLLAYLLDPSNTTPEGVARRYGGEWTEEAGERAALSERLFANLWGRL

EGEERLLWLYREVERPLSAVLAHMEATGVRLDVAYLRALSLEVAEEIARLEAEVFRLAGH

```
-continued
PFNLNSRDQLERVLFDELGLPAIGKTEXTGKRSTSAAVLEALREAHPIVEKILQYRELTK

LKSTYIDPLPDLIHPRTGRLHTRENQTATATGRLSSSDPNLQNIPVXTPLGQRIRRAFIA

EEGWLLVALDYSQIELRVLAHLSGDENLIRVFQEGRDIHTETASWMFGVPREAVDPLMR

AAKTINFGVLYGMSAHRLSQELAIPYEEAQAFIERYFQSFPKVRAWIEKTLEEGRRRGYV

ETLFGRRRYVPDLEARVKSVREAAERMAFNMPVQGTAADLMKLAMVKLFPRLEEMGARML

LQVHDELVLEAPKERAEAVARLAKEVMEGVYPLAVPLEVEVGIGEDWLSAKE

SEQ ID NO: 14 - KTQ R210V:
MRGSHHHHHHTDPHAALEEAPWPPPEGAFVGFVLSRKEPMWADLLALAAARGGRVHRAPE

PYKALRDLKEARGLLAKDLSVLALREGLGLPPGDDPMLLAYLLDPSNTTPEGVARRYGGE

WTEEAGERAALSERLFANLWGRLEGEERLLWLYREVERPLSAVLAHMEATGVRLDVAYLR

ALSLEVAEEIARLEAEVFRLAGHPFNLNSXDQLERVLFDELGLPAIGKTEKTGKRSTSAA

VLEALREAHPIVEKILQYRELTKLKSTYIDPLPDLIHPRTGRLHTRFNQTATATGRLSSS

DPNLQNIPVRTPLGQRIRRAFIAEEGWLLVALDYSQIELRVLAHLSGDENLIRVFQEGRD

IHTETASWMFGVPREAVDPLMRRAAKTINFGVLYGMSAHRLSQELAIPYEEAQAFIERYF

QSFPKVRAWIEKTLEEGRRRGYVETLFGRRRYVPDLEARVKSVREAAERMAFNMPVQGTA

ADLMKLAMVKLFPRLEEMGARMLLQVHDELVLEAPKERAEAVARLAKEVMEGVYPLAVPL

EVEVGIGEDWLSAKEKA

SEQ ID NO: 15 - KTQ R210H:
MRGSHHHHHHTDPHAALEEAPWPPPEGAFVGFVLSRKEPMWADLLALAAARGGRVHRAPE

PYKALRDLKEARGLLAKDLSVLALREGLGLPPGDDPMLLAYLLDPSNTTPEGVARRYGGE

WTEEAGERAALSERLFANLWGRLEGEERLLWLYREVERPLSAVLAHMEATGVRLDVAYLR

ALSLEVAEEIARLEAEVERLAGHPFNLNSXDQLERVLFDELGLPAIGKTEKTGKRSTSAA

VLEALREAHPIVEKILQYRELTKLKSTYIDPLPDLIHPRTGRLHTRFNQTATATGRLSSS

DPNLQNIPVRTPLGQRIRRAFIAEEGWLLVALDYSQIELRVLAHLSGDENLIRVFQEGRD

IHTETASWMFGVPREAVDPLMRRAAKTINFGVLYGMSAHRLSQELAIPYEEAQAFIERYF

QSFPKVRAWIEKTLEEGRRRGYVETLFGRRRYVPDLEARVKSVREAAERMAFNMPVQGTA

ADLMKLAMVKLFPRLEEMGARMLLQVHDELVLEAPKERAEAVARLAKEVMEGVYPLAVPL

EVEVGIGEDWLSAKEKA

SEQ ID NO: 16 - KTQ K231W:
MRGSHHHHHHTDPHAALEEAPWPPPEGAFVGFVLSRKEPMWADLLALAAARGGRVHRAPE

PYKALRDLKEARGLLAKDLSVLALREGLGLPPGDDPMLLAYLLDPSNTTPEGVARRYGGE

WTEEAGERAALSERLFANLWGRLEGEERLLWLYREVERPLSAVLAHMEATGVRLDVAYLR

ALSLEVAEEIARLEAEVERLAGHPFNLNSRDQLERVLFDELGLPAIGKTEXTGKRSTSAA

VLEALREAHPIVEKILQYRELTKLKSTYIDPLPDLIHPRTGRLHTRFNQTATATGRLSSS

DPNLQNIPVRTPLGQRIRRAFIAEEGWLLVALDYSQIELRVLAHLSGDENLIRVFQEGRD

IHTETASWMFGVPREAVDPLMRRAAKTINFGVLYGMSAHRLSQELAIPYEEAQAFIERYF

QSFPKVRAWIEKTLEEGRRRGYVETLFGRRRYVPDLEARVKSVREAAERMAFNMPVQGTA

ADLMKLAMVKLFPRLEEMGARMLLQVHDELVLEAPKERAEAVARLAKEVMEGVYPLAVPL

EVEVGIGEDWLSAKEKA

SEQ ID NO: 17 - KTQ K231Y:
MRGSHHHHHHTDPHAALEEAPWPPPEGAFVGFVLSRKEPMWADLLALAAARGGRVHRAPE

PYKALRDLKEARGLLAKDLSVLALREGLGLPPGDDPMLLAYLLDPSNTTPEGVARRYGGE

WTEEAGERAALSERLFANLWGRLEGEERLLWLYREVERPLSAVLAHMEATGVRLDVAYLR
```

ALSLEVAEEIARLEAEVFRLAGHPFNLNSRDQLERVLFDELGLPAIGKTE TGKRSTSAA

VLEALREAHPIVEKILQYRELTKLKSTYIDPLPDLIHPRTGRLHTRFNQTATATGRLSSS

DPNLQNIPVRTPLGQRIRRAFIAEEGWLLVALDYSQIELRVLAHLSGDENLIRVFQEGRD

IHTETASWMFGVPREAVDPLMRRAAKTINFGVLYGMSAHRLSQELAIPYEEAQAFIERYF

QSFPKVRAWIEKTLEEGRRGYVETLFGRRRYVPDLEARVKSVREAAERMAFNMPVQGTA

ADLMKLAMVKLFPRLEEMGARMLLQVHDELVLEAPKERAEAVARLAKEVMEGVYPLAVPL

EVEVGIGEDWLSAKEKA

SEQ ID NO: 18 - KTQ R259K:
MRGSHHHHHHTDPHAALEEAPWPPPEGAFVGFVLSRKEPMWADLLALAAARGGRVHRAPE

PYKALRDLKEARGLLAKDLSVLALREGLGLPPGDDPMLLAYLLDPSNTTPEGVARRYGGE

WTEEAGERAALSERLFANLWGRLEGEERLLWLYREVERPLSAVLAHMEATGVRLDVAYLR

ALSLEVAEEIARLEAEVERLAGHPFNLNSRDQLERVLFDELGLPAIGKTEKTGKRSTSAA

VLEALREAHPIVEKILQY ELTKLKSTYIDPLPDLIHPRTGRLHTRENQTATATGRLSSS

DPNLQNIPVRTPLGQRIRRAFIAEEGWLLVALDYSQIELRVLAHLSGDENLIRVFQEGRD

IHTETASWMFGVPREAVDPLMRRAAKTINFGVLYGMSAHRLSQELAIPYEEAQAFIERYF

QSFPKVRAWIEKTLEEGRRGYVETLFGRRRYVPDLEARVKSVREAAERMAFNMPVQGTA

ADLMKLAMVKLFPRLEEMGARMLLQVHDELVLEAPKERAEAVARLAKEVMEGVYPLAVPL

EVEVGIGEDWLSAKEKA

SEQ ID NO: 19 - KTQ R259L:
MRGSHHHHHHTDPHAALEEAPWPPPEGAFVGFVLSRKEPMWADLLALAAARGGRVHRAPE

PYKALRDLKEARGLLAKDLSVLALREGLGLPPGDDPMLLAYLLDPSNTTPEGVARRYGGE

WTEEAGERAALSERLFANLWGRLEGEERLLWLYREVERPLSAVLAHMEATGVRLDVAYLR

ALSLEVAEEIARLEAEVERLAGHPFNLNSRDQLERVLFDELGLPAIGKTEKTGKRSTSAA

VLEALREAHPIVEKILQY ELTKLKSTYIDPLPDLIHPRTGRLHTRENQTATATGRLSSS

DPNLQNIPVRTPLGQRIRRAFIAEEGWLLVALDYSQIELRVLAHLSGDENLIRVFQEGRD

IHTETASWMFGVPREAVDPLMRRAAKTINFGVLYGMSAHRLSQELAIPYEEAQAFIERYF

QSFPKVRAWIEKTLEEGRRGYVETLFGRRRYVPDLEARVKSVREAAERMAFNMPVQGTA

ADLMKLAMVKLFPRLEEMGARMLLQVHDELVLEAPKERAEAVARLAKEVMEGVYPLAVPL

EVEVGIGEDWLSAKEKA

SEQ ID NO: 20 - KTQ R310L:
MRGSHHHHHHTDPHAALEEAPWPPPEGAFVGFVLSRKEPMWADLLALAAARGGRVHRAPE

PYKALRDLKEARGLLAKDLSVLALREGLGLPPGDDPMLLAYLLDPSNTTPEGVARRYGGE

WTEEAGERAALSERLFANLWGRLEGEERLLWLYREVERPLSAVLAHMEATGVRLDVAYLR

ALSLEVAEEIARLEAEVERLAGHPFNLNSRDQLERVLFDELGLPAIGKTEKTGKRSTSAA

VLEALREAHPIVEKILQYRELTKLKSTYIDPLPDLIHPRTGRLHTRFNQTATATGRLSSS

DPNLQNIPV TPLGQRIRRAFIAEEGWLLVALDYSQIELRVLAHLSGDENLIRVFQEGRD

IHTETASWMFGVPREAVDPLMRRAAKTINFGVLYGMSAHRLSQELAIPYEEAQAFIERYF

QSFPKVRAWIEKTLEEGRRGYVETLFGRRRYVPDLEARVKSVREAAERMAFNMPVQGTA

ADLMKLAMVKLFPRLEEMGARMLLQVHDELVLEAPKERAEAVARLAKEVMEGVYPLAVPL

EVEVGIGEDWLSAKEKA

SEQ ID NO: 21 - KTQ R310I:
MRGSHHHHHHTDPHAALEEAPWPPPEGAFVGFVLSRKEPMWADLLALAAARGGRVHRAPE

PYKALRDLKEARGLLAKDLSVLALREGLGLPPGDDPMLLAYLLDPSNTTPEGVARRYGGE

WTEEAGERAALSERLFANLWGRLEGEERLLWLYREVERPLSAVLAHMEATGVRLDVAYLR

ALSLEVAEEIARLEAEVERLAGHPFNLNSRDQLERVLFDELGLPAIGKTEKTGKRSTSAA

VLEALREAHPIVEKILQYRELTKLKSTYIDPLPDLIHPRTGRLHTRFNQTATATGRLSSS

DPNLQNIPVITPLGQRIRRAFIAEEGWLLVALDYSQIELRVLAHLSGDENLIRVFQEGRD

IHTETASWMFGVPREAVDPLMRRAAKTINFGVLYGMSAHRLSQELAIPYEEAQAFIERYF

QSFPKVRAWIEKTLEEGRRRGYVETLFGRRRYVPDLEARVKSVREAAERMAFNMPVQGTA

ADLMKLAMVKLFPRLEEMGARMLLQVHDELVLEAPKERAEAVARLAKEVMEGVYPLAVPL

EVEVGIGEDWLSAKEKA

SEQ ID NO: 22 - KTQ R383V:
MRGSHHHHHHTDPHAALEEAPWPPPEGAFVGFVLSRKEPMWADLLALAAARGGRVHRAPE

PYKALRDLKEARGLLAKDLSVLALREGLGLPPGDDPMLLAYLLDPSNTTPEGVARRYGGE

WTEEAGERAALSERLFANLWGRLEGEERLLWLYREVERPLSAVLAHMEATGVRLDVAYLR

ALSLEVAEEIARLEAEVERLAGHPFNLNSRDQLERVLFDELGLPAIGKTEKTGKRSTSAA

VLEALREAHPIVEKILQYRELTKLKSTYIDPLPDLIHPRTGRLHTRFNQTATATGRLSSS

DPNLQNIPVRTPLGQRIRRAFIAEEGWLLVALDYSQIELRVLAHLSGDENLIRVFQEGRD

IHTETASWMFGVPREAVDPLMFVAAKTINFGVLYGMSAHRLSQELAIPYEEAQAFIERYF

QSFPKVRAWIEKTLEEGRRRGYVETLFGRRRYVPDLEARVKSVREAAERMAFNMPVQGTA

ADLMKLAMVKLFPRLEEMGARMLLQVHDELVLEAPKERAEAVARLAKEVMEGVYPLAVPL

EVEVGIGEDWLSAKEKA

SEQ ID NO: 23 - KTQ R383T:
MRGSHHHHHHTDPHAALEEAPWPPPEGAFVGFVLSRKEPMWADLLALAAARGGRVHRAPE

PYKALRDLKEARGLLAKDLSVLALREGLGLPPGDDPMLLAYLLDPSNTTPEGVARRYGGE

WTEEAGERAALSERLFANLWGRLEGEERLLWLYREVERPLSAVLAHMEATGVRLDVAYLR

ALSLEVAEEIARLEAEVERLAGHPFNLNSRDQLERVLFDELGLPAIGKTEKTGKRSTSAA

VLEALREAHPIVEKILQYRELTKLKSTYIDPLPDLIHPRTGRLHTRFNQTATATGRLSSS

DPNLQNIPVRTPLGQRIRRAFIAEEGWLLVALDYSQIELRVLAHLSGDENLIRVFQEGRD

IHTETASWMFGVPREAVDPLMFTAAKTINFGVLYGMSAHRLSQELAIPYEEAQAFIERYF

QSFPKVRAWIEKTLEEGRRRGYVETLFGRRRYVPDLEARVKSVREAAERMAFNMPVQGTA

ADLMKLAMVKLFPRLEEMGARMLLQVHDELVLEAPKERAEAVARLAKEVMEGVYPLAVPL

EVEVGIGEDWLSAKEKA

SEQ ID NO: 24 - KTQ VL22: K231Y, R310K, R383T:
MRGSHHHHHHTDPHAALEEAPWPPPEGAFVGFVLSRKEPMWADLLALAAARGGRVHRAPE

PYKALRDLKEARGLLAKDLSVLALREGLGLPPGDDPMLLAYLLDPSNTTPEGVARRYGGE

WTEEAGERAALSERLFANLWGRLEGEERLLWLYREVERPLSAVLAHMEATGVRLDVAYLR

ALSLEVAEEIARLEAEVERLAGHPFNLNSRDQLERVLFDELGLPAIGKTEYTGKRSTSAA

VLEALREAHPIVEKILQYRELTKLKSTYIDPLPDLIHPRTGRLHTRFNQTATATGRLSSS

DPNLQNIPVKTPLGQRIRRAFIAEEGWLLVALDYSQIELRVLAHLSGDENLIRVFQEGRD

-continued

```
IHTETASWMFGVPREAVDPLMR*AAKTINFGVLYGMSAHRLSQELAIPYEEAQAFIERYF

QSFPKVRAWIEKTLEEGRRRGYVETLFGRRRYVPDLEARVKSVREAAERMAFNMPVQGTA

ADLMKLAMVKLFPRLEEMGARMLLQVHDELVLEAPKERAEAVARLAKEVMEGVYPLAVPL

EVEVGIGEDWLSAKEKA
```

EXAMPLES

The following examples illustrate the invention. These examples should not be construed as to limit the scope of this invention. The examples are included for purposes of illustration and the present invention is limited only by the claims.

Example 1

For our studies we employed KlenTaq DNA polymerase (Barnes 1992). Compared to Taq DNA polymerase, KlenTaq is approximately twice as thermostable and displays half the error rate of Taq DNA polymerase (Barnes 1992; Villbrandt, Sanger and Schomburg 1997; Lawyer et al., 1993).

In order to study the impact of basic amino acids K508, R487, R536, R587 and R660 on selectivity and activity we used saturation mutagenesis at the different positions.

Reagents and Instruments

Oligonucleotides were purchased from Biomers or Metabion, Germany. HeLa Genomic DNA was bought from New England Biolabs (N4006S). dNTPs were either from Roche or Fermentas. Phusion polymerase was purchased from Thermo Scientific, DNase I, SphI and HindIII from Fermentas, the Gel Extraction and EpiTect MSP kit from Qiagen and used according to their manuals. The KlenTaq DNA polymerase and the respective mutants were overexpressed in E. coli and purified with Ni-IDA as previously described (Gloeckner, Sauter and Marx 2007). Enzyme purity and quantity were determined by SDS-PAGE using an albumin standard dilution curve. Real-time PCR was performed on a Chromo4 instrument from Bio-Rad or on a Roche LightCycler 480 system. SYBRgreen I was purchased from Fluka. Templates were bought at NIBSC (Prothrombin Mutation G20210A, Human gDNA, 1st International Genetic Reference Panel 2005—WHO International Standard or Reference Reagent Product Number 05/130 and Factor V Leiden, Human gDNA, 1st International Genetic Reference Panel 2004—WHO International Standard or Reference Reagent Product Number 04/224).

Screening and Real-Time ASA Assay with KlenTaq Wild-Type and Mutants (Lysate or Purified Enzyme):

Reaction mixtures contained 50 mM Tris-HCl (pH 9.2), 16 mM (NH4)2SO4, 0.1% Tween20, 2.5 mM MgCl2, 250 µM of each dNTP and 0.6× SYBRgreen I. As primer F20-for [750 nM, 20 nt, 5'-d(CGT TGG TCC TGA AGG AGG AT)-3'] (SEQ ID NO: 25) and F20-rev [750 nM, 20 nt, 5'-d(CGC GCA GCA CGC GCC GCC GT)-3'] (SEQ ID NO: 26) were used. As templates, either F90A [60 pM, 90 nt, 5' d(CCG TCA GCT GTG CCG TCG CGC AGC ACG CGC CGC CGT GGA CAG AGG ACT GCA GAA AAT CAA CCT ATC CTC CTT CAG GAC CAA CGT ACA GAG) 3'] (SEQ ID NO: 27) or F90G [60 pM, 90 nt, 5' d(CCG TCA GCT GTG CCG TCG CGC AGC ACG CGC CGC CGT GGA CAG AGG ACT GCA GAA AAT CAA CCT GTC CTC CTT CAG GAC CAA CGT ACA GAG)-3'] (SEQ ID NO: 28) were used. Both templates had the same sequence except of the SNP at the indicated position. After an initial denaturation cycle (95° C. for 3 min), the product was amplified by 30 PCR cycles (95° C. for 15 s, 55° C. for 20 s and 72° C. for 30 s), and analyzed by melting curve measurement. KlenTaq DNA polymerase wild-type and the respective mutants were used either 50 nM or 350 nM as indicated. Lysates were prepared in reaction buffer and directly used after heat inactivation 40 min at 75° C. and clearance (40 min 4500 rpm).

The screen was conducted as done previously in a high-throughput format using heat-treated E. coli lysates (Gloeckner, Kranaster and Marx 2010). Entities with increased extension selectivity were identified as those variants that cause amplification curves with matched DNA substrates with lower threshold crossing (c(t)) cycle numbers than that of mismatched DNA substrates.

Interestingly at all five investigated positions (R487, K508, R536, R587 and R660), we found hits with strongly increased extension selectivity. In order to exclude expression level variations and other artefacts from the crude heat-treated E. coli lysates, we verified our findings by purifying selected hits and repeating ASA (data not shown).

While the wild-type enzyme displays no significant discrimination, employment of the selected mutants leads to significantly increased mismatch extension selectivity for all variants.

Concerning the identified hits, only in three cases the basic amino acid arginin was exchanged to another basic amino acid such as histidine (R487H) or lysine (R536K and R587K). Only two mutants with mutations to polar and uncharged amino acids as tyrosine and threonine were found (K508Y and R660T). In several cases substitutions towards hydrophobic amino acids were found: R487V, K508W, R587I, and R660V.

Example 2

In order to directly compare activity and mismatch extension selectivity of the selected mutants we performed primer extension experiments.

Primer Extension Assay with KlenTaq Wild-Type and Mutants

Reaction mixtures contained 50 mM Tris•HCl (pH 9.2), 16 mM (NH4)2SO4, 0.1% Tween 20, 2.5 mM MgCl2, 250 nM DNA polymerase wild-type or mutant, DNA primer [150 nM, 20 nt, 5'-[32P]-d(CGT TGG TCC TGA AGG AGG AT)-3'] (SEQ ID NO: 29), 300 nM template F33A [300 nM, 33 nt, 5'-d(AAA TCA ACC TAT CCT CCT TCA GGA CCA ACG TAC)-3'] (SEQ ID NO: 30) or F33G [300 nM, 33 nt, 5'-d(AAA TCA ACC TGT CCT CCT TCA GGA CCA ACG TAC)-3'] (SEQ ID NO: 31) for the match or mismatch case. After an initial denaturation and annealing step (95° C. for 2 min, 0.5° C./s cooling to 40° C. for 30 sec), a temperature of 55.0° C. was applied and the reaction was started by addition of 200 µM dNTPs. After 10 min of incubation the reactions were stopped by addition of two volumes gel loading buffer (80% formamide, 20 mM EDTA). Product mixtures were separated by 12% denaturating PAGE and visualised using a Phosphorimager.

We used a 20-nucleotides radioactively labelled primer and two 33-nucleotides templates having the same sequence except of one specific position (FIG. 1). Depending on the template the 3' end of the primer was either matched or mismatched. Reactions were incubated isothermal at 55° C. and started by addition of dNTPs and quenched after 10 min, followed by PAGE analysis. As depicted in FIG. 1, the KlenTaq wild-type shows full-length product and, as reported before for 3'-5'-exonuclease-deficient polymerases, a non-templated additional nucleotide incorporation for the match and the mismatch case (Clark 1988; Kranaster and Marx 2009; Kranaster et al., 2010). Notably not all primer is converted for the mismatch case indicating the intrinsic mismatch extension discrimination. However, none of the mutants show product formation for the mismatch case after 10 min but full-length product for the match case. Whereas some mutants as R487V or K508Y clearly show reduced activity, which is visible as intermediate product-bands, other mutants as R587K or R660V show clean full-length product formation in the match case, indicating a conserved high activity comparable to the wild-type enzyme.

Example 3

To characterize the identified mutants, the key step of the primer extension was examined for the most active variants. For this purpose the single nucleotide incorporation turnover rates (under pre-steady state conditions) were determined for the match and mismatch case.
Reaction Kinetics of KlenTaq Wild-Type and Mutants Reaction mixtures contained 20 mM Tris•HCl (pH 7.5), 50 mM NaCl, 2.0 mM MgCl2, 1 µM DNA polymerase wild-type or mutant, DNA primer [100 nM, 20 nt, 5'-[32P]-d(CGT TGG TCC TGA AGG AGG AT)-3'] (SEQ ID NO: 29), template F33A [130 nM, 33 nt, 5'-d(AAA TCA ACC TAT CCT CCT TCA GGA CCA ACG TAC)-3'] (SEQ ID NO: 30) or F33G [130 nM, 33 nt, 5'-d(AAA TCA ACC TGT CCT CCT TCA GGA CCA ACG TAC)-3'] (SEQ ID NO: 31) for the match or mismatch case. After an initial denaturation and annealing step (95° C. for 2 min, 0.5° C./s cooling to 40° C. for 30 sec), a temperature of 37.0° C. was applied and the reaction was started by addition of 600 µM dATP. After incubation for certain times the reactions were stopped by addition of 300 mM EDTA either manually or with a KinTek Rapid Quench-Flow instrument. Product mixtures were separated by 12% denaturing PAGE and visualised using a Phosphorimager. Quantification was done with Quantity One software from Biorad.

Figure 2:
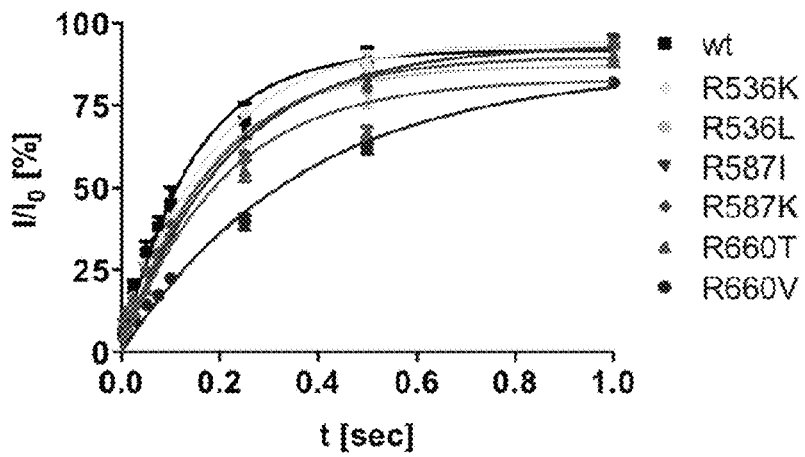
FIG. 2: Single turnover rates (pre-steady-state). A) Conversion of primer vs. time for the match case. B) Conversion of primer vs. time for the mismatch case.
Figure 2:
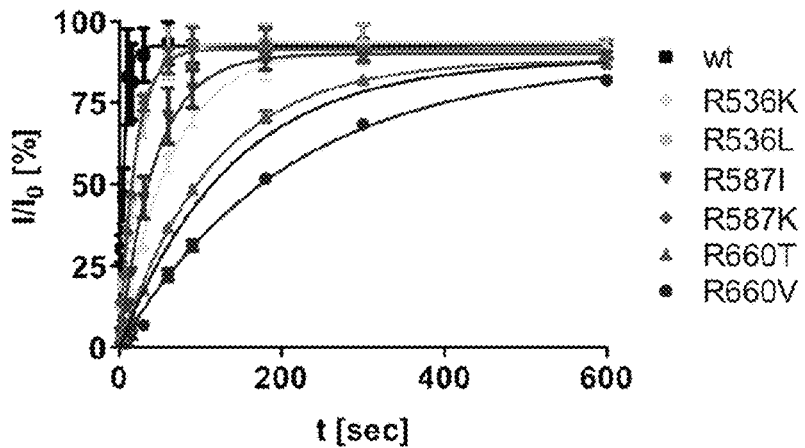

High concentrations of enzyme were used to saturate binding of the DNA substrate. At high dNTP concentrations (600 µM) the first order rate reflects kcat (Minnick et al., 1999). The results are shown in FIG. 2 and Table 1. Notably reaction times for the mismatch case were up to 600 s whereas for the match case full conversion was detected after 1 s for all polymerases.

A measure for the selectivity is kA/kG as shown in FIG. 2 and Table 1. This ratio is significantly increased in the selected mutants, compared to the wild-type enzyme, given as (kA/kG)/(kA/kG)wt. For instance, the elongation of the matched vs. mismatched primer was increased by up to 14-folds compared to KlenTaq wild-type in mutant R660T.

Example 4

Figure 3:
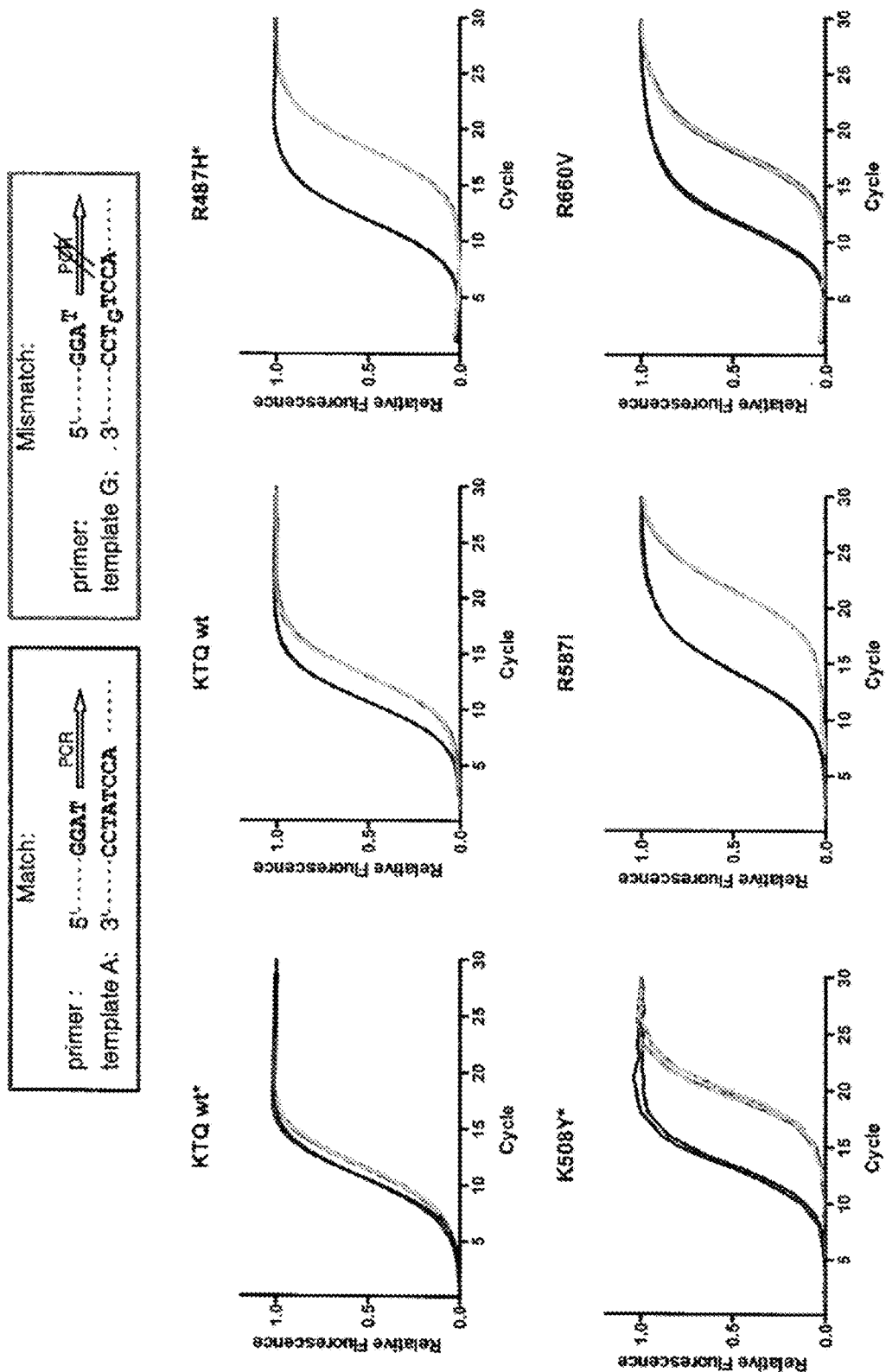
FIG. 3: RT-PCR of Klentaq wt and selected KTQ mutants are shown. The match case is black the mismatch case gray. Template concentration is 60 pM, primer 750 nM and dNTPs 250 p.M each. The polymerase concentrations are 50 nM or 350 nM as indicated with *.

To verify our findings we purified the most selective enzymes at each position and repeated the PCR with purified enzymes with different polymerase concentrations. Real-time-PCR (RT-PCR) graphs for some selected mutants are shown in FIG. 3.

Real-time PCR ASA assay with KlenTaq wt and mutants. Reaction mixtures (20 pL) contained 50 mM Tris-HCl (pH 9.2), 16 mM (NH4)2SO4, 0.1% Tween20, 2.5 mM MgCl2, 250 pM of each dNTP and 0.6× SYBRgreen I. As primer F20-for [750 nM, 20 nt, 5'-d(CGTTGGTCCTGAAGGAG-GAT)-3'] (SEQ ID NO: 32) and F20-rev [750 nM, 20 nt, 5'-d(CGCGCAGCACGCGCCGCCGT)-3'] (SEQ ID NO: 33) were used. As templates, either F90A [60 pM, 90 nt, 5'-d(CCGTCAGCTGTGCCGTCGCGCAGCACGCGC-CGCCGTGGACAGAGGACTGCAGAAAATCAAC-CTATCCTCCTT CAGGACCAACGTACA GAG)-3'] (SEQ ID NO: 34) or F9OG [60 pM, 90 nt, 5'-d(CCGTCAGCT-GTGCCGTCGCGCAGCACGCG CCGCCGTGGACA-GAGGACTGCAGAAAATCAACCTGTCCTCCTTCAG-GACCAAC GTACAGAG)-3'] (SEQ ID NO: 35) were used. Both templates had the same sequence except of the SNP at the indicated position. After an initial denaturation cycle (95° C. for 3 min), the product was amplified by 30 PCR cycles (95° C. for 15 s, 55° C. for 20 s and 72° C. for 30 s), and analyzed by melting curve measurement.

KlenTaq DNA polymerase wt and the respective mutants were used either 50 nM or 350 nM as indicated. Results can be taken from FIG. 3, showing that the new mutants show high discrimination and high activity compared to the wt and already known mutants.

We shuffled the two best mutant-genes for each position and the wild-type gene and created a new library. The best hit we could isolate contained the following mutations K508Y, R587K and R660T. Experiments with the purified enzyme showed discriminations in the range of the best single mutants.

Example 5

Next, we investigated the performance of the most active single mutants on human HeLa genomic DNA in the context of the Factor II prothrombin SNP. The prothrombin SNP is

TABLE 1

| Single turnover rates (pre-steady-state) of KlenTaq wt and mutants | | | | | | | |
|---|---|---|---|---|---|---|---|
| | wt | R536K | R536L | R587I | R587K | R660T | R660V |
| kA (s-1) | 7.0 | 5.6 | 5.7 | 4.7 | 5.3 | 4.9 | 2.7 |
| kG (s-1) | 1.7E−01 | 1.6E−02 | 4.7E−02 | 2.3E−02 | 5.3E−02 | 8.8E−03 | 9.3E−03 |
| kA/kG | 41 | 360 | 120 | 210 | 100 | 560 | 290 |
| (kA/kG)/ (kA/kG)wt | 1.0 | 8.6 | 2.9 | 5.0 | 2.4 | 14 | 7.1 | kA = kcat match primer
kG = kcat mismatch primer connected to an increased thrombosis risk and therefore of high scientific interest (Marchiori et al., 2007).

Real-Time PCR Assay with KlenTaq Wild-Type and Mutants and Human gDNA

Reaction mixtures (20 μL) contained 50 mM Tris-HCl (pH 9.2), 16 mM (NH4)2SO4, 0.1% Tween20, 2.5 mM MgCl2, 200 μM of each dNTP, 0.6× SYBRgreen I, DMSO 5% and KlenTaq polymerase 100 nM. As forward primer F2forG [100 nM, 23 nt, 5' d(CCC AAT AAA AGT GAC TCT CAG CG) 3'] (SEQ ID NO: 36) or F2forA [100 nM, 23 nt, 5' d(CCC AAT AAA AGT GAC TCT CAG CA) 3'] (SEQ ID NO: 37) was used. As reverse Primer F2rev [100 nM, 20 nt, 5' d(CCA GAG AGC TGC CCA TGA AT) 3'] (SEQ ID NO: 38) was used. (Prothrombin Mutation G20210A). Template (HeLa genomic DNA) concentration was 20 ng per reaction. For real time-PCR after an initial denaturation cycle (95° C. for 3 min), the product was amplified by 50 PCR cycles (95° C. for 20 s, 57° C. for 10 s and 72° C. for 30 s), and analyzed by melting curve measurement.

Here the mutant R660V performed best (Table 2). All mutants showed increased Δc(t) values on genomic DNA compared to KlenTaq wild-type. Most mutants show wild-type like high activity with c(t) values of 30 for the match case compared to KlenTaq wild-type with a c(t) value of 28 for the match case. The mutant R660V shows the highest mismatch extension discrimination of 18 cycles compared to 8.5 for the KlenTaq wild-type and also wild-type like high activity. Therefore further experiments were carried out with this enzyme.

TABLE 2

Threshold crossing points of real-time PCR experiments using HeLa genomic DNA as a template and Factor II prothrombin SNP

|  | wt | R536K | R536L | R587I | R587K | R680T | R660V |
|---|---|---|---|---|---|---|---|
| c (t) Match | 28 | 30 | 30 | 32 | 31 | 30 | 30 |
| c (t) Mismatch | 37 | 44 | 46 | 49 | 47 | 46 | 48 |
| Δc(t) | 8.5 | 13 | 16 | 17 | 15 | 16 | 18 |

Example 6

To test the ability of mutant R660V in ASA on human genomic DNA not only with HeLa DNA (genotype G/G) but also with the two other genotypes G/A and AA, we used control DNA standards from the National Institute for Biological Standards and Control (NIBSC). Human gDNA templates for all three naturally occurring cases are available: wild-type (genotype G/G), homozygote (genotype A/A) and heterozygote (genotype G/A).

Real-Time PCR ASP Assay with KlenTaq R660V Mutant and Human gDNA Standard

Reaction mixtures contained 50 mM Tris-HCl (pH 9.2), 16 mM (NH4)2SO4, 0.1% Tween20, 2,0 mM MgCl2, 200 μM of each dNTP, 1× SYBRgreen I and KlenTaq R660V 100 nM. As forward primer F2forG [100 nM, 23 nt, 5' d(CCC AAT AAA AGT GAC TCT CAG CG) 3'] (SEQ ID NO: 36) or F2forA [100 nM, 23 nt, 5' d(CCC AAT AAA AGT GAC TCT CAG CA) 3'] (SEQ ID NO: 37) was used. As reverse Primer F2rev [100 nM, 20 nt, 5' d(CCA GAG AGC TGC CCA TGA AT) 3'] (SEQ ID NO: 38) was used. Templates for homozygote, heterozygote and wild type were used. Template concentration was 10 ng per reaction. After an initial denaturation cycle (95° C. for 3 min), the product was amplified by 60 PCR cycles (95° C. for 20 s, 57° C. for 10 s and 72° C. for 30 s), and analyzed by melting curve measurement. For normal PCR cycling was stopped after 50 cycles and the PCR products analyzed on 2.5% agarose gel.

Figure 4:
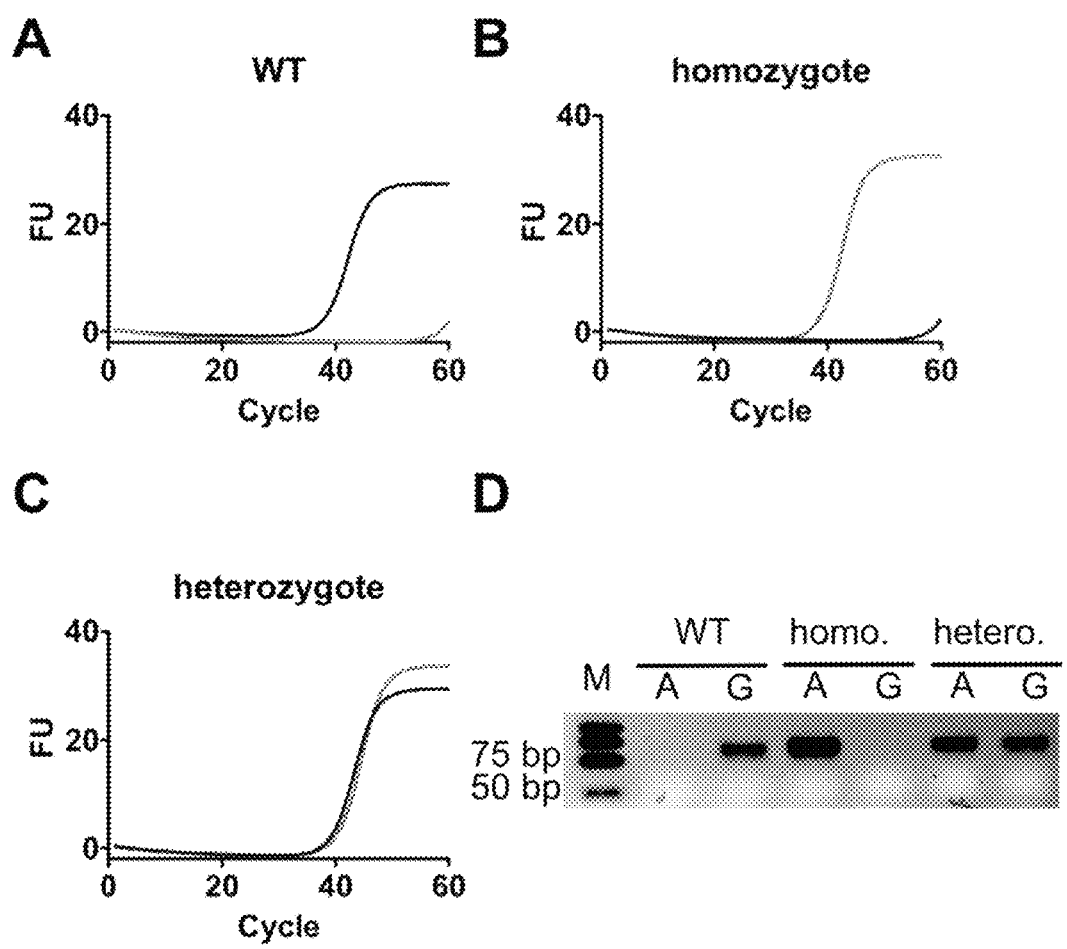
FIG. 4: ASA of Factor II prothrombin, Human gDNA (WHO International Standards) with R660V mutant. Allele-specific primers A and G result in a 3' end match or mismatch, depending on the chosen template. In black primer A is shown, in grey primer B. A) ASA Real time PCR curves of Factor II wild type (genotype G/G). B) ASA Real time PCR curves of Factor II homozygote (genotype A/A). C) ASA Real time PCR curves of Factor II heterozygote (genotype G/A). D) Agarose gel of ASA PCR. M=Marker, A=Primer A, G=Primer G. WT indicates the used wild-type template, homo. the homozygote and hetero. the heterozygote template.

As shown in FIG. 4, for both homozygote cases product formation was only detected for the corresponding match primer. The signal of the mismatched primers is shifted clearly and at the beginning of the exponential phase after 60 cycles. In the case of the heterozygote template product formation is detected for both allele specific primers, as expected. Therefore fast and reliable SNP genotyping is possible. Detection can either be performed as real-time PCR (FIGS. 4 A, B and C) or by standard PCR and subsequent analyses on agarose gel (FIG. 4 D). After 50 PCR cycles clear product bands in the expected lines are visible. As shown all three possible SNP genotypes can be clearly distinguished. This shows that the R660V KlenTaq mutant is also suitable for ASA in standard laboratories without real time-PCR cycler.

Example 7

Next we established a multiplexing ASA assay for the Factor II prothrombin SNP by incorporating into one of the allelic primers at the 5' end a 30-nucleotide overhanging sequence. Thus both alleles can be detected in the same reaction according to their different melting temperatures respectively (Papp et al., 2003).

Multiplexing ASA Assay with R660V from Standarts and Blood

Figure 5:
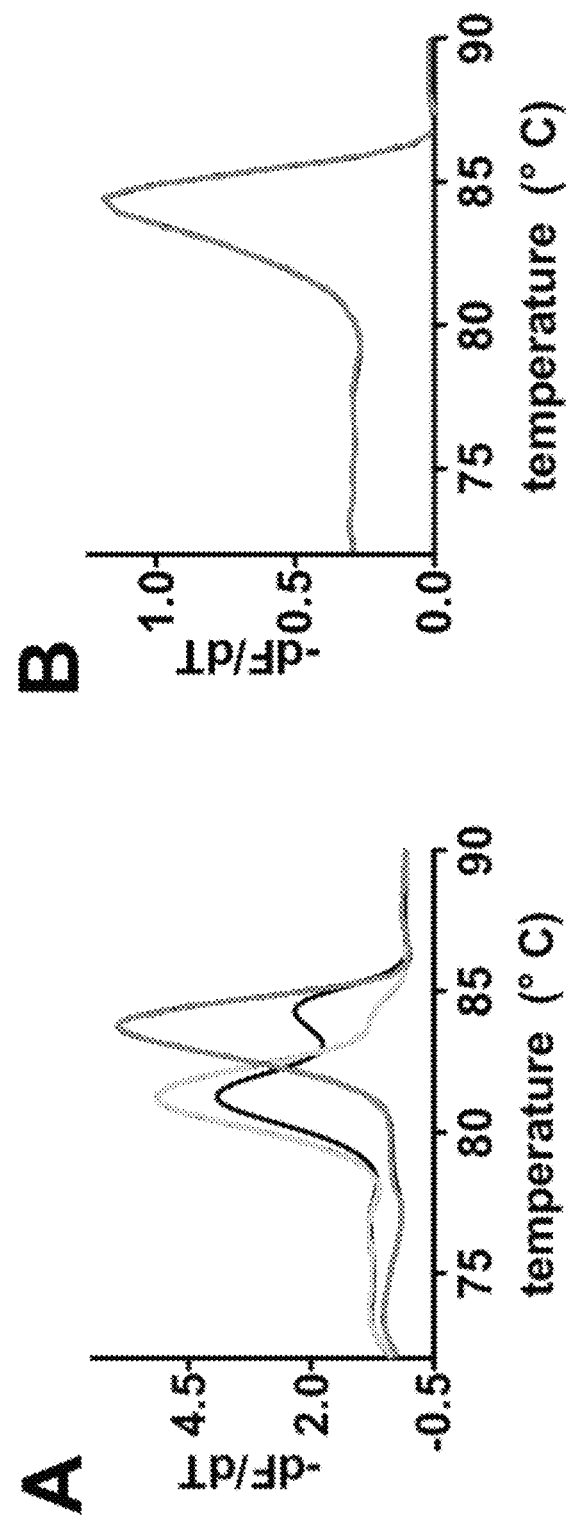
FIG. 5: Multiplexing ASA melting curve assay of Factor II prothrombin. A) Melting curves of the multiplexing ASA products resulting from three different reference gDNA samples are shown (wild-type in dark grey (genotype G/G), heterozygote in black (genotype (G/A), homozygote in light grey (A/A)). B) Resulting melting curve from a whole blood sample, which resulted in a wild-type genotype.

SNP Factor II G20210A (64 bp A-allele or G-allelel 94 bp, respectively) was detected by direct amplification from 10 ng of genomic reference DNA, using allele-specific primers forward Factor II Prothrombin G20210A Prothrombin: F2forGlang [100 nM, 53 nt, 5' d(ATC CAA CTC TCT ACG CAA TGG CAC TAG AGA CCC AAT AAA AGT GAC TCT CAG CG) 3'] (SEQ ID NO: 50) or F2forA [125 nM, 23 nt, 5' d(CCC AAT AAA AGT GAC TCT CAG CA) 3'] (SEQ ID NO: 37) and reverse primer F2rev [100 nM, 20 nt, 5' d(CCA GAG AGC TGC CCA TGA AT) 3'] (SEQ ID NO: 38). Real-time ASA contained 50 mM Tris-HCl (pH 9.2), 16 mM (NH4)2SO4, 0.1% Tween20, 2.5 mM MgCl2, 200 μM of each dNTP, 1× SYBRgreen I and KlenTaq R660V 100 nM or 30× SYBRgreen I and 500 nM KlenTaq R660V in case of a blood sample. Preceding the reaction, 0.5 μl blood per well were allowed to dry at room temperature for 5 min before adding 10 μl of the above described reaction solution. After an initial denaturation cycle (95° C. for 3 min), the product was amplified by 40 PCR cycles (95° C. for 15 s, 57° C. for 5 s and 72° C. for 15 s), and immediately analyzed by a melting curve measurement We successfully tested our assay on all three gDNA references, displaying a wild-type, homozygote or heterozygote genotype (FIG. 5A). Notably, all experiments can be conducted in any suitable real-time PCR machine able to do a melting point analysis with Sybr Green I.

As reported, Taq DNA polymerase is significantly inhibited in the presence of less than 0.2% whole blood (Abu Al-Soud and Radström 1988; Kermekchiev et al., 2009). In contrast, KlenTaq DNA polymerase exhibits an increased resistance (Kermekchiev et al., 2009). Thus, we next studied PCR performance in the presence of whole blood. Due to fluorescence quenching effects of blood on SYBRGreen I (Kermekchiev et al. 2009), a 30× increased dye concentrations was required for real-time PCR, additionally we used a 5× higher DNA polymerase concentration in comparison to ASA using purified gDNA samples. However, the genotype of the blood sample was successfully identified as wild-type (wt; G/G), as a melting peak was observed only for the G-allelic primer (FIG. 5B), concluding that the direct detection of SNPs from whole blood samples is achievable. This might pave a new way in clinical diagnostics without the need of time and cost intensive sample preparations.

Example 8

Real-time PCR ASP assay with KlenTaq R660V mutant and human gDNA standards.

Figure 6:
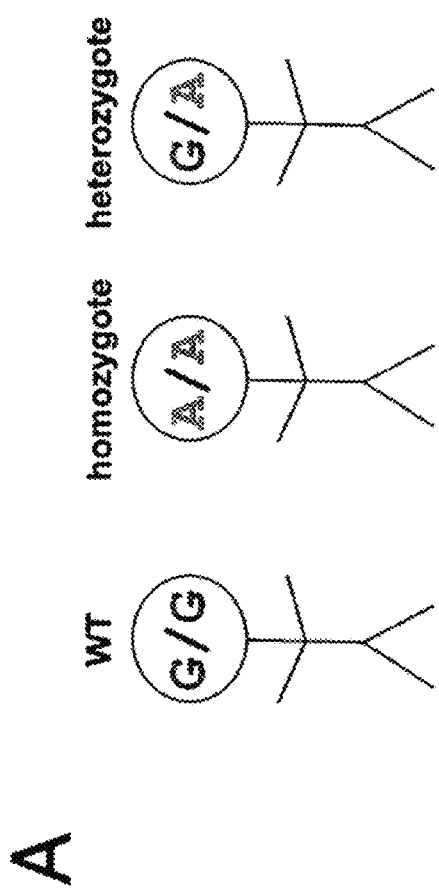
FIG. 6: Real-time PCR ASP assay with KlenTaq R660V mutant and human gDNA standarts. ASA of Factor V Leiden, Human gDNA (WHO International Standard) with R660V mutant. Allele-specific primers A and G result in a 3' end match or mismatch depending on the chosen template. B) ASA Real time PCR curves.
Figure 6:
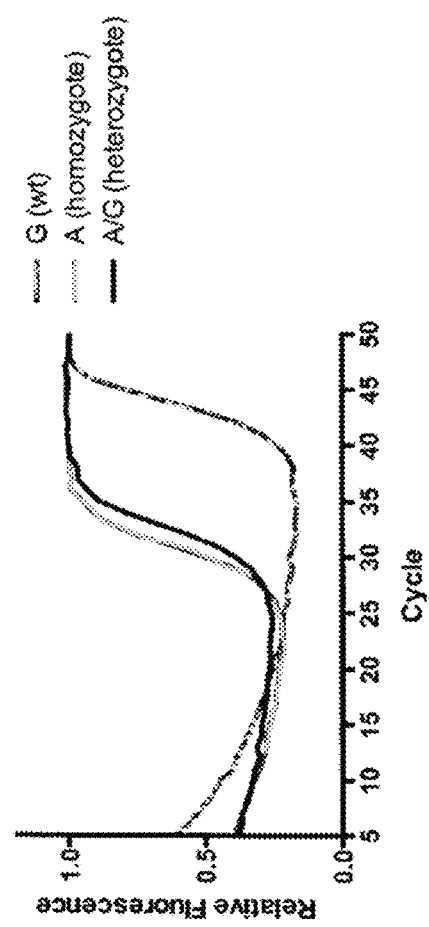
Figure 6:
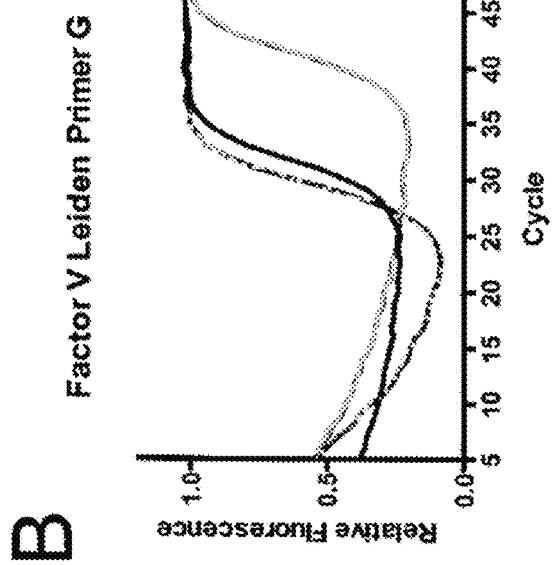

Reaction mixtures (20 pL) contained 50 mM Tris-HCl (pH 9.2), 16 mM (NH4)2SO4, 0.1% Tween20, 2.5 mM $MgCl_2$, 200 pM of each dNTP, 1× SYBRgreen I and KlenTaq R660V 100 nM. As forward primer F5forG [100 nM, 18 nt, 5'-d(CAGATCCCTGGACAGGCG)-3'] (SEQ ID NO: 39) or F5forA [100 nM, 18 nt, 5'-d(CAGATCCCTG-GACAGGCA)-3'] (SEQ ID NO: 40) was used. As reverse Primer F5rev [100 nM, 23 nt, 5'-d(GGAGACCTAACAT-GTTCTAGCCA)-3'] (SEQ ID NO: 41) was used. Templates were bought at NIBSC (Factor V Leiden, Human gDNA, 1st International Genetic Reference Panel 2004—WHO International Standard or Reference Reagent Product Number 04/224). Templates for homozygote, heterozygote and wild type Factor V Leiden (FVL) were used. Template concentration was 10 ng per reaction. After an initial denaturation cycle (95° C. for 3 min), the product was amplified by 50 PCR cycles (95° C. for 20 s, 57° C. for 10 s and 72° C. for 30 s), and analyzed by melting curve measurement. Results can be taken from FIG. 6, showing that the mutant R660V shows high discrimination and high activity and therefore is perfectly suited for ASA on gDNA.

Example 9

Finally, we explored the suitability of KlenTaq R660V for 5mC detection and performed MSP within the sequence context of Septin 9. Hypermethylation in the promoter region of the Septin 9 gene is a known colon cancer marker of high scientific interest (Warren et al., 2011).
Real-Time PCR MSP Assay with KlenTaq R660V Mutant Reaction mixtures contained 50 mM Tris-HCl (pH 9.2), 16 mM (NH4)2SO4, 0.1% Tween20, 2.0 mM MgCl2, 200 µM of each dNTP, 1× SYBRgreen I and KlenTaq R660V 50 nM. As forward primer MSP SEPT9con Forw [100 nM, 30 nt, 5' d(GCG CGA TTC GTT GTT TAT TAG TTA TTA TGT) 3'] (SEQ ID NO: 42) was used. As reverse Primers MSP SEPT9con Rev G [100 nM, 31 nt, 5' d(TCG AAA TCC GAA ATA ATC CCA TCC AAC TAC G) 3'] (SEQ ID NO: 43) and MSP SEPT9con Rev A [100 nM, 31 nt, 5' d(TCG AAA TCC GAA ATA ATC CCA TCC AAC TAC A)-3'] (SEQ ID NO: 44) were used. As templates, either Temp Sept9 Methylated 5mC [150 pM, 85 nt, 5' d(TTC GCG CGA TTC GTT GTT TAT TAG TTA TTA TGT CGG ATT TCG CGG TTA ACG CMeGT AGT TGG ATG GGA TTA TTT CGG ATT TCG AAG G) 3'] (SEQ ID NO: 45) or Sept9 unmethylated U [150 pM, 85 nt, 5' d(TTC GCG CGA TTC GTT GTT TAT TAG TTA TTA TGT CGG ATT TCG CGG TTA ACG UGT AGT TGG ATG GGA TTA TTT CGG ATT TCG AAG G)-3'] (SEQ ID NO: 46) were used. Both templates had the same sequence except of the 5mC or U at the indicated position. After an initial denaturation cycle (95° C. for 3 min), the product was amplified by 50 PCR cycles (95° C. for 20 s, 57° C. for 10 s and 72° C. for 30 s), and analyzed by melting curve measurement. Qiagen Epi-Tect MSR kit was used as described in the manual.

Figure 7:
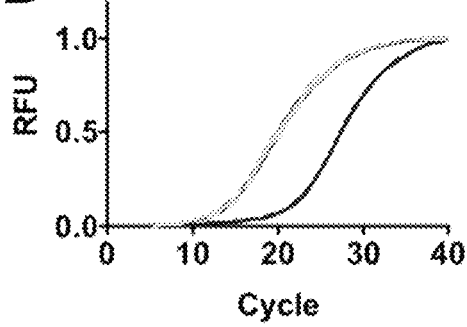
FIG. 7: Real-time PCR spectra of MSP with mutant R660V. As template either a template with 5mC or with U was used. Primers A and G result in a 3'-end match or mismatch depending on the chosen template. A) Graphic depiction of used primer (P) and template (T). B) Real-time PCR curves using a commercially available kit. C) Real-time PCR curves for KlenTaq R660V.
Figure 7:
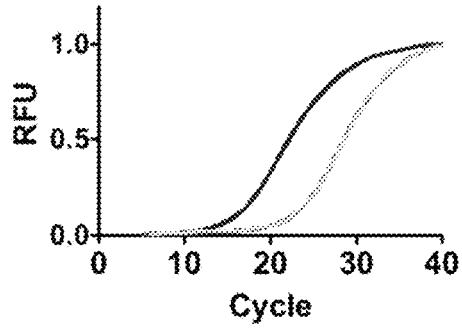
Figure 7:
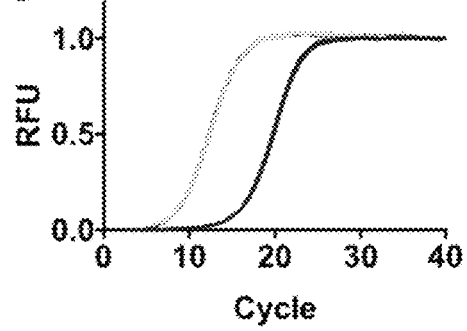
Figure 7:
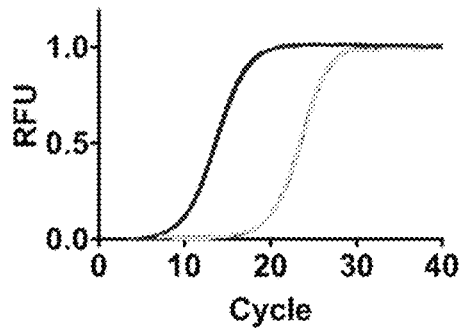

Both templates have the same sequence except of the 5mC or U at the indicated position and therefore representing the converted or unconverted DNA. To benchmark KlenTaq R660V we also used a commercially available kit with the same templates and primers. As shown in FIG. 7 KlenTaq R660V exhibits clear discrimination for both used primers with the respective mismatch template as well as high activity. Compared with the commercial kit, mutant KlenTaq R660V shows higher activity and discrimination. Thus, robust and fast detection of epigenetic methylation status is possible using KlenTaq R660V.

Example 10

Distal Mismatches

Experimental Description:
Mismatch Short Term Memory Assay with KlenTaq Wild-Type and Mutants Reaction mixtures contained 50 mM Tris*HCl (pH 9.2), 16 mM $(NH_4)_2SO_4$, 0.1% Tween 20, 2.5 mM $MgCl_2$, 350 nM DNA polymerase wild-type or mutant, one of the DNA primers ["P", 150 nM, 20 nt, 5'-[$^{32}$P]-d(CGT TGG TCC TGA AGG AGG AT)-3'] (SEQ ID NO: 47), [150 nM, ["P+3", 150 nM, 23 nt, 5'-[$^{32}$P]-d(CGT TGG TCC TGA AGG AGG ATA GG)-3'] (SEQ ID NO: 48), or ["P+6", 150 nM, 26 nt, 5'-[$^{32}$P]-d(CGT TGG TCC TGA AGG AGG ATA GGT TG)-3'] (SEQ ID NO: 49), 300 nM template F33A [300 nM, 33 nt, 5'-d(AAA TCA ACC TAT CCT CCT TCA GGA CCA ACG TAC)-3'] (SEQ ID NO: 30) or F33G [300 nM, 33 nt, 5'-d(AAA TCA ACC TGT CCT CCT TCA GGA CCA ACG TAC)-3'] (SEQ ID NO: 31) for the match or mismatch case. After an initial denaturation and annealing step (95° C. for 2 min, 0.5° C./s cooling to 40° C. for 30 sec), a temperature of 72.0° C. was applied and the reaction was started by addition of 200 µM dNTPs. After 5 min of incubation the reactions were stopped by addition of two volumes gel loading buffer (80% formamide, 20 mM EDTA). Product mixtures were separated by 12% denaturating PAGE and visualised using a Phosphorimager. Quantification was done with Quantity One software from Biorad.

Figure 8:
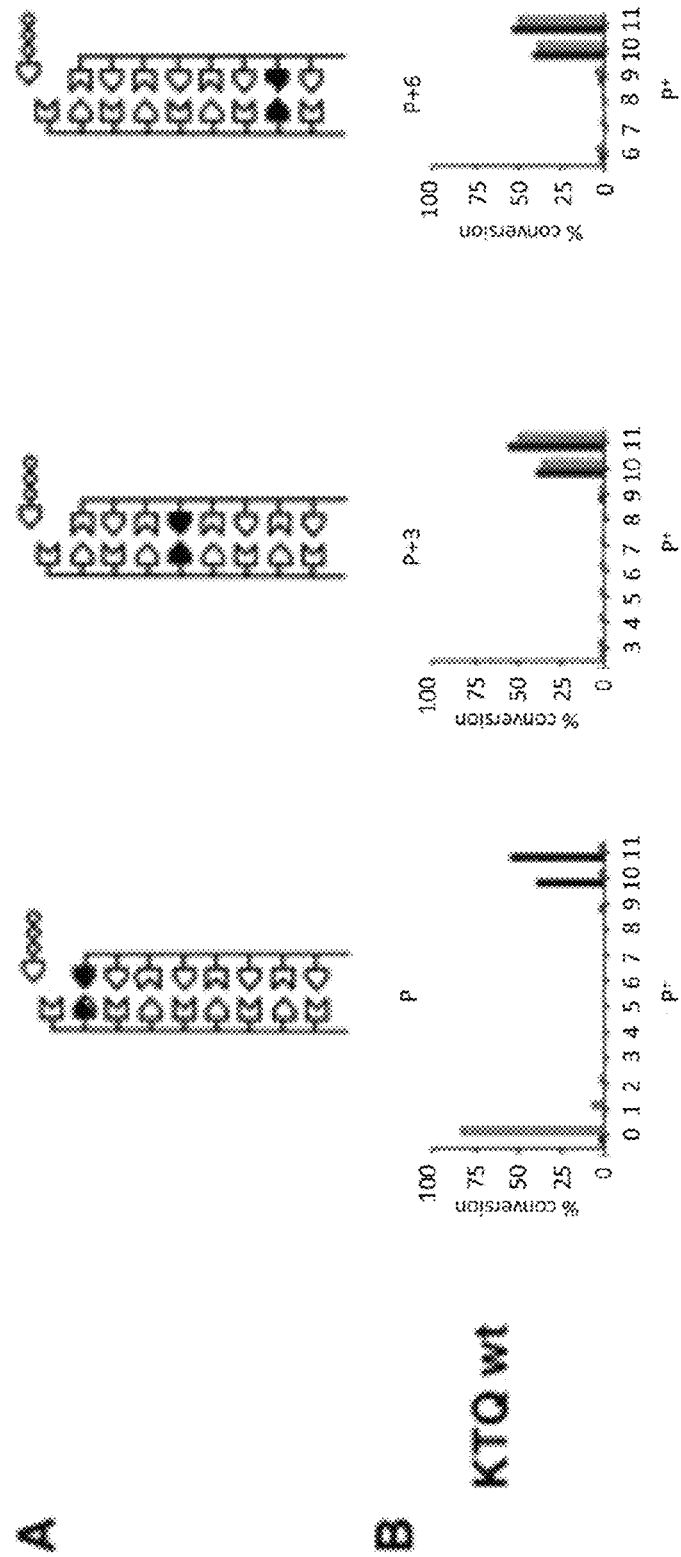
FIG. 8: Mismatch extension memory of KTQ wt and two selected mutants. A) Mismatch primers with a 3' terminal or a distal mismatch were used, as indicated here. Symbols indicate a canonical base pair, the black symbols indicate a mismatched base pair. B, C and D) Conversion [%] of matched primers (black) and mismatched primers (grey) are shown. Primer P has a 3'-mismatched end, Primer P+3 is three bases elongated after a mismatch, primer P+6 was elongated by 6 bases. On the x-axis the detected primer length is depicted, on the y-axis the conversion in % of detected primer of this specific length, e.g. "p+10" is the full-length product, and "p+11" the +1 product band.

Beside the standard elongation of a fully matched vs. a terminal 3'-mismatched primer, the elongation of a distal mismatch can also be used for mutation analysis, SNP genotyping or methylated cytosine (5mC) detection: We elongated the 3'-mismatched primer terminus by one, three, or six canonically matched bases (see FIG. 8 A, schematic drawing). In case of the KlenTaq wt only the 3'-terminal mismatched primer (P primer) is discriminated, the distal match vs. mismatches using the P+3 or the P+6 primers do not result in any significant conversion differences. In contrary, many of the mutants for instance R536K and K508W show enhanced short-term memories (See FIGS. 8 C and D), thus a clear difference in conversion rates is detectible even if the primers P+3 and P+6 are used. This shows that most of our mutants e.g. K508W can be very useful for SNP genotyping with primers with distal mismatches of up to six bases from the 3' primer end as well.

REFERENCES

Abu Al-Soud W, Rådström P (1998) Capacity of nine thermostable DNA polymerases To mediate DNA amplification in the presence of PCR-inhibiting samples. Appl. Environ. Microbiol. 64: 3748-3753.
Akey D T, Akey J M, Zhang K, Jin L (2002). "Assaying DNA methylation based on high-throughput melting curve approaches". Genomics 80 (4): 376-84. doi: 10.1006/geno.2002.6851. PMID 12376091

Altschul S F, Madden T L, Schäffer A A, Zhang J, Zhang Z, Miller W, Lipman D J. (1997) "Gapped BLAST and PSI-BLAST: a new generation of protein database search programs" Nucl. Acids Res. 25, 3389-3402.

Altschul S F "A protein alignment scoring system sensitive at all evolutionary distances" J. Mol. Evol. 36 (1993), 290-300.

Altschul, "Basic local alignment search tool" J. Mol. Biol. 215 (1990), 403-410.

Arya M, Shergill I S, Williamson M, Gommersall L, Arya N, Patel H R H "Basic principles of quantitative real time PCR" Expert Rev. Mol. Diagn. 5(2):209-219.

Ausubel, "Current Protocols in Molecular Biology", Green Publishing Associates and Wiley Interscience, N.Y. (1989), Ausubel, Current Protocols in Molecular Biology, Green Publishing Associates and Wiley Interscience, N.Y. (1989), (1994)

Barnes W M. (1992) The fidelity of Taq polymerase catalyzing PCR is improved by an N-terminal deletion. Gene 112(1):29-35

Beaucage et al. (1981) "2',5'-Oligoadenylate:antisense chimeras-synthesis and properties" Tetrahedron Lett. 22:1859-1862.

Boosalis, M. S., Petruska, J., and Goodman, M. F., (1987) "DNA polymerase insertion fidelity. Gel assay for site-specific kinetics" J Biol Chem 262 (30), 14689-96.

Bryant, F. R., Johnson, K. A., and Benkovic, S. J., (1983) "Elementary steps in the DNA polymerase I reaction pathway" Biochemistry 22 (15), 3537-46, Brown E L, Belagaje R, Ryan M J, Khorana H G. (1979) "Chemical synthesis and cloning of a tyrosine tRNA gene" Meth. Enzymol. 68:109-151.

Blasco M A, Méndez J, Lázaro J M, Blanco L, Salas M (1995) Primer terminus stabilization at the phi 29 DNA polymerase active site. Mutational analysis of conserved motif KXY. J Biol Chem 270: 2735-2740.

Biles B D, Connolly B A (2004) Low-fidelity *Pyrococcus furiosus* DNA polymerase mutants useful in error-prone PCR. Nucleic Acids Res 32: e176. doi:10.1093/nar/gnh174

Chien A, Edgar D B, Trela J M (1976). "Deoxyribonucleic acid polymerase from the extreme thermophile *Thermus aquaticus*". J. Bact. 127 (3): 1550-7. PMC 232952. PMID 8432.

Chothia C, Baker R W, Pauling (1976) "Conformation of acetylcholine at muscarinic nerve receptors: crystal and molecular structure of 2-trimethylammoniummethyl-5-methyl furan iodide (5-methylfurmethide iodide)" J. Mol. Biol. 105 (4): 517

Clark J M (1988) Novel non-templated nucleotide addition reactions catalyzed by procaryotic and eucaryotic DNA polymerases. Nucleic Acids Res 16: 9677-9686.

Copeland W C, Wang T S (1993) Mutational analysis of the human DNA polymerase alpha. The most conserved region in alpha-like DNA polymerases is involved in metal-specific catalysis. J Biol Chem 268: 11028-11040.

Consortium T1GP, The 1000 Genomes Consortium Participants are arranged by project role TBIAAFAWIEFPIA-PLAI, author C, committee S, Medicine PGBCO, et al. (2012) An integrated map of genetic variation from 1,092 human genomes. Nature 490: 56-65. doi:10.1038/nature11632

Creighton, S., Bloom, L. B., and Goodman, M. F., (1995) "Gel fidelity assay measuring nucleotide misinsertion, exonucleolytic proofreading, and lesion bypass efficiencies" Methods Enzymol 262, 232-56.

Dawson M A, Kouzarides T (2012) Cancer Epigenetics: From Mechanism to Therapy. Cell 150: 12-27. doi: 10.1016/j.cell.2012.06.013

Deng D, Liu Z, Du Y (2010) Chapter 5—Epigenetic Alterations as Cancer Diagnostic, Prognostic, and Predictive Biomarkers. 1st ed. Elsevier Inc. 125-176 pp. doi: 10.1016/B978-0-12-380864-6.00005-5

Eads C A, Danenberg K D, Kawakami K, et al. (April 2000). "MethyLight: a high-throughput assay to measure DNA methylation". Nucleic Acids Res. 28 (8): E32. doi: 10.1093/nar/28.8.e32. PMC 102836. PMID 10734209

Ehrlich M, Wang R (1981) 5-Methylcytosine in eukaryotic DNA. Science 212: 1350-1357. doi:10.1126/science.6262918

Feltus F A, Lee E K, Costello J F, Plass C, Vertino P M (2006) DNA motifs associated with aberrant CpG island methylation. Genomics 87: 572-579. doi:10.1016/j.ygeno.2005.12.016

Firth A E, Patrick W M (2005) Statistics of protein library construction. Bioinformatics 21: 3314-3315. doi:10.1093/bioinformatics/bti516

Franklin M C, Wang J, Steitz T A (2001) Structure of the Replicating Complex of a Pol α Family DNA Polymerase. Cell 105: 657-667. doi:10.1016/S0092-8674(01)00367-1

Frazer K A, Ballinger D G, Cox D R, Hinds D A, Stuve L L, et al. (2007) A second generation human haplotype map of over 3.1 million SNPs. Nature 449: 851-861. doi:10.1038/nature06258

Frommer M, McDonald L E, Millar D S, Collis C M, Watt F, et al. (1992) A genomic sequencing protocol that yields a positive display of 5-methylcytosine residues in individual DNA strands. Proc Natl Acad Sci USA 89: 1827-1831.

Gardiner-Garden M, Frommer M. (1987) "CpG islands in vertebrate genomes" Journal of Molecular Biology 196 (2): 261-82

Germer S, Higuchi R (1999) Single-tube genotyping without oligonucleotide probes. Genome Res 9: 72-78.

Germer S, Holland M J, Higuchi R (2000) High-throughput SNP allele-frequency determination in pooled DNA samples by kinetic PCR. Genome Res 10: 258-266.

Gill P, Ghaemi A "Nucleic acid isothermal amplification technologies—a review" Nucleosides, Nucleotides and Nucleic acids 27:224-243.

Gloeckner C, Kranaster R, Marx A (2010) Directed evolution of DNA polymerases: construction and screening of DNA polymerase mutant libraries. Curr Protoc Chem Biol 2: 89-109. doi:10.1002/9780470559277.ch090183

Gloeckner C, Sauter K B M, Marx A (2007) Evolving a thermostable DNA polymerase that amplifies from highly damaged templates. Angew Chem Int Ed Engl 46: 3115-3117.

Guo Z, Liu Q, Smith L M (1997) Enhanced discrimination of single nucleotide polymorphisms by artificial mismatch hybridization. Nat Biotechnol 15: 331-335. doi: 10.1038/nbt0497-331

Hacia J G, Fan J B, Ryder O, Jin L, Edgemon K, et al. (1999) Determination of ancestral alleles for human single-nucleotide polymorphisms using high-density oligonucleotide arrays. Nat Genet 22: 164-167. doi:10.1038/9674

Haukur Gudnason, Martin Dufva, 1 D. D. Bang, and Anders Wolff (2007) "Comparison of multiple DNA dyes for real-time PCR: effects of dye concentration and sequence composition on DNA amplification and melting temperature" Nucleic Acids Res 35(19): e127.

Hayatsu H, Wataya Y, Kai K, Iida S (1970) Reaction of sodium bisulfite with uracil, cytosine, and their derivatives. Biochemistry 9: 2858-2865.

Heichman K A, Warren J D (2012) DNA methylation biomarkers and their utility for solid cancer diagnostics. Clin. Chem. Lab. Med. 50: 1707-1721. doi:10.1515/cclm-2011-0935

Heyn H, Esteller M (2012) DNA methylation profiling in the clinic: applications and challenges. Nat Rev Genet 13: 679-692. doi:10.1038/nrg3270

Higgins and Hames (Eds.) "Nucleic acid hybridization, a practical approach" IRL Press Oxford, Washington D.C., (1985)

Hodges R. S., Shu B.-Y., Zhou N. E., Mant C. T., (1994) "Reversed-phase liquid chromatography as a useful probe of hydrophobic interactions involved in protein folding and protein stability" J. Chromatogr. A 29; 676(1):3-15.

International HapMap Consortium (2005) A haplotype map of the human genome. Nature 437: 1299-1320. doi: 10.1038/nature04226

International HapMap 3 Consortium, Altshuler D M, Gibbs R A, Peltonen L, Altshuler D M, et al. (2010) Integrating common and rare genetic variation in diverse human populations. Nature 467: 52-58. doi:10.1038/nature09298

Ishikawa Y, Tokunaga K, Kashiwase K, Akaza T, Tadokoro K, et al. (1995) Sequence-based typing of HLA-A2 alleles using a primer with an extra base mismatch. Hum Immunol 42: 315-318.

Jones P A (2012) Functions of DNA methylation: islands, start sites, gene bodies and beyond. Nat Rev Genet 13: 484-492. doi:10.1038/nrg3230

Johnson, K. A., (1993) "Conformational coupling in DNA polymerase fidelity" Annu Rev Biochem 62, 685-713.

Johnson M P (2004) Locked nucleic acid (LNA) single nucleotide polymorphism (SNP) genotype analysis and validation using real-time PCR. Nucleic Acids Res 32: e55-e55. doi:10.1093/nar/gnh046

Jorde L B, Watkins W S, Bamshad M J, Dixon M E, Ricker C E, et al. (2000) The distribution of human genetic diversity: a comparison of mitochondrial, autosomal, and Y-chromosome data. Am. J. Hum. Genet. 66: 979-988. doi:10.1086/302825

Kallol M. Biswas, Daniel R. DeVido, John G. Dorsey (2003) Journal of Chromatography A, 1000, 637-655.

Kathiresan S, Voight B F, Musunuru K, Ardissino D, Mannucci P M, et al. (2009) Genome-wide association of early-onset myocardial infarction with single nucleotide polymorphisms and copy number variants. Nat Genet 41: 334-341. doi:10.1038/ng.327

Kermekchiev M B, Kirilova L I, Vail E E, Barnes W M (2009) Mutants of Taq DNA polymerase resistant to PCR inhibitors allow DNA amplification from whole blood and crude soil samples. Nucleic Acids Res 37: e40-e40. doi: 10.1093/nar/gkn1055

Kranaster R, Marx A (2009) Taking fingerprints of DNA polymerases: multiplex enzyme profiling on DNA arrays. Angew. Chem. Int. Ed. 48: 4625-4628. doi:10.1002/anie.200900953

Kranaster R, Drum M, Engel N, Weidmann M, Hufert F T, et al. (2010) One-step RNA pathogen detection with reverse transcriptase activity of a mutated thermostable *Thermus aquaticus* DNA polymerase. Biotechnol J 5: 224-231. doi:10.1002/biot.200900200

Kristensen L S, Hansen L L (2009) PCR-Based Methods for Detecting Single-Locus DNA Methylation Biomarkers in Cancer Diagnostics, Prognostics, and Response to Treatment. Clin Chem 55: 1471-1483. doi:10.1373/clinchem.2008.121962

Kunkel T A, Bebenek K (2000) DNA replication fidelity. Annu. Rev. Biochem. 69: 497-529. doi:10.1146/annurev.biochem.69.1.497

Lander E S, Linton L M, Birren B, Nusbaum C, Zody M C, et al. (2001) Initial sequencing and analysis of the human genome. Nature 409: 860-921. doi:10.1038/35057062

Lawyer F C, Stoffel S, Saiki R K, Chang S Y, Landre P A, et al. (1993) High-level expression, purification, and enzymatic characterization of full-length *Thermus aquaticus* DNA polymerase and a truncated form deficient in 5" to 3" exonuclease activity. PCR Methods Appl. 2: 275-287.

Lawyer F C, et al. (1993). "High-level expression, purification, and enzymatic characterization of full-length *Thermus aquaticus* DNA polymerase" PCR Methods Appl. 2 (4): 275-87. PMID 8324500

Li Y, Korolev S, Waksman G (1998) Crystal structures of open and closed forms of binary and ternary complexes of the large fragment of *Thermus aquaticus* DNA polymerase I: structural basis for nucleotide incorporation. EMBO J 17: 7514-7525. doi:10.1093/emboj/17.24.7514

Loh E, Salk J J, Loeb L A (2010) Optimization of DNA polymerase mutation rates during bacterial evolution. Proc Natl Acad Sci USA 107: 1154-1159. doi:10.1073/pnas.0912451107

Loh E, Loeb L A (2005) Mutability of DNA polymerase I: implications for the creation of mutant DNA polymerases. DNA Repair (Amst.) 4: 1390-1398. doi:10.1016/j.dnarep.2005.09.006

Lutz M W, Crenshaw D G, Saunders A M, Roses A D (2011) The importance of being connected. J. Alzheimers Dis. 24: 247-251. doi:10.3233/JAD-2010-101765

Matteucci et al. (1981) Am. Chem. Soc. 103:3185-3191

Marchiori A, Mosena L, Prins M H, Prandoni P (2007) The risk of recurrent venous thromboembolism among heterozygous carriers of factor V Leiden or prothrombin G20210A mutation. A systematic review of prospective studies. Haematologica 92: 1107-1114.

McCarthy J J, Hilfiker R (2000) The use of single-nucleotide polymorphism maps in pharmacogenomics. Nat Biotechnol 18: 505-508. doi:10.1038/75360

Minnick D T, Bebenek K, Osheroff W P, Turner R M, Astatke M, et al. (1999) Side chains that influence fidelity at the polymerase active site of *Escherichia coli* DNA polymerase I (Klenow fragment). J Biol Chem 274: 3067-3075.

Moret M. A., Zebende G. F., (2007) "Amino acid hydrophobicity and accessible surface area". Phys. Rev. E 75 011920;

Myakishev M V, Khripin Y, Hu S, Hamer D H (2001) High-throughput SNP genotyping by allele-specific PCR with universal energy-transfer-labeled primers. Genome Res 11: 163-169.

Newton C R, Graham A, Heptinstall L E, Powell S J, Summers C, et al. (1989) Analysis of any point mutation in DNA. The amplification refractory mutation system (ARMS). Nucleic Acids Res 17: 2503-2516.

Narang S A, Hsiung H M, Brousseau R. (1979) "Improved phosphotriester method for the synthesis of gene fragments" Meth. Enzymol. 68:90-99.

Nielsen P E, Eghoim M, Berg R H, Buchardt O. (1991) "Sequence-selective recognition of DNA by strand displacement with a thymine-substituted polyamide" Science 254:1497-1500.

Novembre J, Johnson T, Bryc K, Kutalik Z, Boyko A R, et al. (2008) Genes mirror geography within Europe. Nature 456: 98-101. doi:10.1038/nature07331

Nozaki Y., Tanford C. (1971) "The solubility of amino acids and two glycine peptides in aqueous ethanol and dioxane solutions. Establishment of a hydrophobicity scale" J. Biol. Chem. 246(7):2211

Papp A C, Pinsonneault J K, Cooke G, Sadée W (2003) Single nucleotide polymorphism genotyping using allele-specific PCR and fluorescence melting curves. BioTechniques 34: 1068-1072.

Patel P H, Kawate H, Adman E, Ashbach M, Loeb L A (2001) A single highly mutable catalytic site amino acid is critical for DNA polymerase fidelity. J Biol Chem 276: 5044-5051. doi:10.1074/jbc.M008701200

Pastinen T, Raitio M, Undroos K, Tainola P, Peltonen L, et al. (2000) A system for specific, high-throughput genotyping by allele-specific primer extension on microarrays. Genome Res 10: 1031-1042.

Phillips, J. C. (2009) "Scaling and self-organized criticality in proteins: Lysozyme c" Phys. Rev. E 80 051916

Plass M., Valko K., Abraham M. H. "Determination of solute descriptors of tripeptide derivatives based on high-throughput gradient high-performance liquid chromatography retention data" J. Chromatogr. A 803(1998) 51-60.

Piccioli P, Serra M, Gismondi V, Pedemonte S, Loiacono F, Lastraioli S, Bertario L, De Angioletti M, Varesco L, Notaro R. (2006) Multiplex tetra-primer amplification refractory mutation system PCR to detect 6 common germline mutations of the MUTYH gene associated with polyposis and colorectal cancer Clin Chem. April; 52(4): 739-43

Rand K, Qu W, Ho T, Clark S J, Molloy P (June 2002). Conversion-specific detection of DNA methylation using real-time polymerase chain reaction (ConULight-MSP) to avoid false positives. Methods 27 (2): 114-20. doi:10.1016/S1046-2023(02)00062-2. PMID 12095268

Raum T, Gruber R, Riethmüller G, Kufer P. (2001) Cancer Immunol. Immunother. 50(3), 141-150.

Reetz M T, Kahakeaw D, Lohmer R (2008) Addressing the Numbers Problem in Directed Evolution. ChemBioChem 9: 1797-1804. doi:10.1002/cbic.v9:11

Relling M V, Dervieux T (2001) Pharmacogenetics and cancer therapy. Nat Rev Cancer 1: 99-108. doi:10.1038/35101056

Ronaghi M (2001) Pyrosequencing sheds light on DNA sequencing. Genome Res 11: 3-11.

Roses A D (2000) Pharmacogenetics and the practice of medicine. Nature 405: 857-865. doi:10.1038/35015728

Roses A D (2002) Genome-based pharmacogenetics and the pharmaceutical industry. Nat. Rev. Drug Disc. 1: 541-549. doi:10.1038/nrd840

Roses A D (2002) Pharmacogenetics place in modern medical science and practice. Life Sciences 70: 1471-1480. doi:10.1016/50024-3205(01)01532-6

Rudinger N Z, Kranaster R, Marx A (2007) Hydrophobic amino acid and single-atom substitutions increase DNA polymerase selectivity. Chem Biol 14: 185-194. doi:10.1016/j.chembiol.2006.11.016

Sambrook, Russell "Molecular Cloning, A Laboratory Manual", Cold Spring Harbor Laboratory, N.Y. (2001).

Saiki, R K et al. (1988). "Primer-directed enzymatic amplification of DNA with a thermostable DNA polymerase.". Science 239 (4839): 487-91. doi:10.1126/science.2448875. PMID 2448875.

Sandoval J, Esteller M (2012) Cancer epigenomics: beyond genomics. Current Opinion in Genetics & Development 22: 50-55. doi:10.1016/j.gde.2012.02.008

Sharp K. A., Nicholls A., Friedman R., Honig B. (1991) "Extracting hydrophobic free energies from experimental data: relationship to protein folding and theoretical models" Biochemistry 30 9686.

Schlebusch C M, Skoglund P, Sjodin P, Gattepaille L M, Hernandez D, et al. (2012) Genomic Variation in Seven Khoe-San Groups Reveals Adaptation and Complex African History. Science. doi:10.1126/science.1227721

Sherry S T, Ward M H, Kholodov M, Baker J, Phan L, Smigielski E M, and Sirotkin K, et al. (2001) "dbSNP: the NCBI database of genetic variation". Nucleic Acids Res. 29 (1): 308-311.

Shi M M (2001) Enabling large-scale pharmacogenetic studies by high-throughput mutation detection and genotyping technologies. Clin Chem 47: 164-172.

Shi M M, Bleavins M R, Ia iglesia de FA (1999) Technologies for detecting genetic polymorphisms in pharmacogenomics. Mol Diagn 4: 343-351. doi:10.154/MODI00400343

Shively L, Chang L, LeBon J M, Liu Q, Riggs A D, et al. (2003) Real-time PCR assay for quantitative mismatch detection. 498-502, 504 pp.

Strerath M, Cramer J, Restle T, Marx A (2002) Implications of active site constraints on varied DNA polymerase selectivity. J Am Chem Soc 124: 11230-11231.

Strerath M, Marx A (2005) Genotyping—from genomic DNA to genotype in a single tube. Angew Chem Int Ed Engl 44: 7842-7849. doi:10.1002/anie.200501444

Strerath M, Gloeckner C, Liu D, Schnur A, Marx A (2007) Directed DNA Polymerase Evolution: Effects of Mutations in Motif C on the Mismatch-Extension Selectivity of Thermus aquaticus DNA Polymerase. ChemBioChem 8: 395-401. doi:10.1002/(ISSN)1439-7633

Summerer D, Rudinger N Z, Detmer I, Marx A (2005) Enhanced Fidelity in Mismatch Extension by DNA Polymerase through Directed Combinatorial Enzyme Design. Angew. Chem. Int. Ed. 44: 4712-4715. doi:10.1002/(ISSN)1521-37

Suzuki M, Yoshida S, Adman E T, Blank A, Loeb L A (2000) Thermus aquaticus DNA polymerase I mutants with altered fidelity. Interacting mutations in the O-helix. J Biol Chem 275: 32728-32735. doi:10.1074/jbc.M000097200

Syvänen A C (2001) Accessing genetic variation: genotyping single nucleotide polymorphisms. Nat Rev Genet 2: 930-942. doi:10.1038/35103535

Syvänen A C (1999) From gels to chips: "minisequencing" primer extension for analysis of point mutations and single nucleotide polymorphisms. Hum Mutat 13: 1-10. doi:10.1002/(SICI)1098-1004(1999)13:1<1::AID-HUMU1>3.0.CO; 2-I73

Tindall K R and Kunkel T A (1988). "Fidelity of DNA synthesis by the Thermus aquaticus DNA polymerase". Biochemistry 27 (16): 6008-13. doi:10.1021/bi00416a027. PMID 2847780

Venter J C, Adams M D, Myers E W, Li P W, Mural R J, et al. (2001) The sequence of the human genome. Science 291: 1304-1351. doi:10.1126/science.1058040

Villbrandt B, Sagner G, Schomburg D (1997) Investigations on the thermostability and function of truncated Thermus aquaticus DNA polymerase fragments. Protein Eng. 10: 1281-1288.

Warren J D, Xiong W, Bunker A M, Vaughn C P, Furtado L V, et al. (2011) Septin 9 methylated DNA is a sensitive and specific blood test for colorectal cancer. BMC Med 9: 133. doi:10.1186/1741-7015-9-133

Wartiovaara A, Syvänen A-C (2002) Analysis of nucleotide sequence variations by solid-phase minisequencing. Methods Mol Biol 187: 57-63. doi:10.1385/1-59259-273-2:057

Wilhelm J, Pingoud A (2003) Real-Time Polymerase Chain Reaction. ChemBioChem 4: 1120-1128. doi:10.1002/(ISSN)1439-7633

Wilhelm J, Reuter H, Tews B, Pingoud A, Hahn M (2002) Detection and quantification of insertion/deletion variations by allele-specific real-time PCR: application for genotyping and chimerism analysis. Biol Chem 383: 1423-1433. doi:10.1515/BC.2002.161

Willard G S (2012) Genomic and Personalized Medicine, Second Edition: V1-2. 2nd ed. Ginsburg G S, Willard H F, editors Academic Press. 1350 p.

Wolfenden R., Andersson L., Cullis P. M., Southgate C. C. B. (1981) "Affinities of amino acid side chains for solvent water" Biochemistry 20:849.

Wu D Y, Ugozzoli L, Pal B K, Wallace R B (1989) Allele-specific enzymatic amplification of beta-globin genomic DNA for diagnosis of sickle cell anemia. Proc Natl Acad Sci USA 86: 2757-2760.

The invention claimed is:

1. A DNA polymerase having at least 95%, or at least 99% identity to the Taq polymerase having the amino acid sequence of SEQ ID NO:1 or its Klenow fragment having the amino acid sequence of SEQ ID NO:2, wherein the DNA polymerase comprises at least one amino acid substitution at position 487 of the amino acid sequence of the Taq polymerase shown in SEQ ID NO:1 or at corresponding position 210 of the Klenow fragment shown in SEQ ID NO:2, and optionally one or more amino acid substitutions at positions corresponding to position(s) 508, 536, 587 and/or 660 of the amino acid sequence of the Taq polymerase shown in SEQ ID NO:1 or at corresponding position 231, 259, 310 and/or 383 of the Klenow fragment shown in SEQ ID NO:2.

2. The DNA polymerase of claim 1, wherein the amino acid sequence further comprises 1, 2, 3, 4, 5, 6, 7, 8, 9, 10, 11, 12, 13, 14, 15, 16, 17, 18, 19 or 20 substitutions with regard to the amino acid sequence showing in SEQ ID NO: 1 or SEQ ID NO:2.

3. The DNA polymerase of claim 1, wherein one or more of the amino acids corresponding to position(s) defined in claim 1 are substituted with a basic, polar and uncharged or hydrophobic amino acid.

4. The DNA polymerase of claim 1 comprising a substitution of R487H/V and further comprises one or more amino acid substitution selected from the group consisting of K508W/Y, R536K/L, R587K/I, and R660T/V for SEQ ID NO: 1 or R210H/V, K231W/Y, R259K/L, R310K/I, and R383T/V for SEQ ID NO: 2.

5. The DNA polymerase of claim 1, wherein said DNA polymerase has the amino acid sequence of anyone of SEQ ID NOs:3, 4, 14 and 15.

6. The DNA polymerase of claim 1, wherein the DNA polymerase discriminates between a mismatched primer and a matched primer, wherein said primers hybridize to a target sequence, and
wherein the mismatched primer comprises a non-canonical nucleotide at its 3' end in relation to the target sequence to which it hybridizes.

7. The DNA polymerase of claim 1, wherein the DNA polymerase, exhibits amplification of a target sequence with a matched primer with a lower threshold crossing (c(t)) cycle number value than with a mismatched primer, wherein said primers hybridize to the target sequence, and wherein the mismatched primer comprises a non-canonical nucleotide at its 3' end in relation to the target sequence to which it hybridizes.

8. The DNA polymerase of claim 7, wherein the difference between the c(t) value of the matched and the c(t) value of the mismatched primer is at least 9, preferably at least 10, 11, 12, 13, 14, 15, 16, 17, 18, 19, 20.

9. A kit comprising the DNA polymerase of claim 1.

* * * * *

SEQUENCE LISTING

```
<160> NUMBER OF SEQ ID NOS: 50

<210> SEQ ID NO 1
<211> LENGTH: 832
<212> TYPE: PRT
<213> ORGANISM: Thermus aquaticus

<400> SEQUENCE: 1

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285
```

-continued

```
Glu Ser Pro Lys Ala Leu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
            355                 360                 365

Pro Gly Asp Asp Pro Met Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
    690                 695                 700
```

-continued

```
Ala Trp Ile Glu Lys Thr Leu Glu Glu Gly Arg Arg Gly Tyr Val
705                 710                 715                 720

Glu Thr Leu Phe Gly Arg Arg Tyr Val Pro Asp Leu Glu Ala Arg
            725                 730                 735

Val Lys Ser Val Arg Glu Ala Ala Glu Arg Met Ala Phe Asn Met Pro
        740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830
```

<210> SEQ ID NO 2
<211> LENGTH: 557
<212> TYPE: PRT
<213> ORGANISM: Artificial Sequence
<220> FEATURE:
<223> OTHER INFORMATION: Klen Taq - KTQ

<400> SEQUENCE: 2

```
Met Arg Gly Ser His His His His His His Thr Asp Pro His Ala Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu Ala
        35                  40                  45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65              70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
        115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
        195                 200                 205

Ser Arg Asp Gln Leu Glu Arg Val Leu Phe Asp Glu Leu Gly Leu Pro
    210                 215                 220

Ala Ile Gly Lys Thr Glu Lys Thr Gly Lys Arg Ser Thr Ser Ala Ala
225                 230                 235                 240
```

```
Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270

Pro Asp Leu Ile His Pro Arg Thr Gly Arg Leu His Thr Arg Phe Asn
            275                 280                 285

Gln Thr Ala Thr Ala Thr Gly Arg Leu Ser Ser Asp Pro Asn Leu
            290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
                340                 345                 350

Arg Val Phe Gln Glu Gly Arg Asp Ile His Thr Glu Thr Ala Ser Trp
            355                 360                 365

Met Phe Gly Val Pro Arg Glu Ala Val Asp Pro Leu Met Arg Arg Ala
            370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
            435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Arg Ala Glu Ala Val Ala Arg Leu Ala Lys Glu
            515                 520                 525

Val Met Glu Gly Val Tyr Pro Leu Ala Val Pro Leu Glu Val Glu Val
            530                 535                 540

Gly Ile Gly Glu Asp Trp Leu Ser Ala Lys Glu Lys Ala
545                 550                 555

<210> SEQ ID NO 3
<211> LENGTH: 832
<212> TYPE: PRT
<213> ORGANISM: Artificial Sequence
<220> FEATURE:
<223> OTHER INFORMATION: Taq R487V

<400> SEQUENCE: 3

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45
```

-continued

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His

```
                465                 470                 475                 480
        Pro Phe Asn Leu Asn Ser Val Asp Gln Leu Glu Arg Val Leu Phe Asp
                            485                 490                 495
        Glu Leu Gly Leu Pro Ala Ile Gly Lys Thr Glu Lys Thr Gly Lys Arg
                        500                 505                 510
        Ser Thr Ser Ala Ala Val Leu Glu Ala Leu Arg Glu Ala His Pro Ile
                    515                 520                 525
        Val Glu Lys Ile Leu Gln Tyr Arg Glu Leu Thr Lys Leu Lys Ser Thr
                530                 535                 540
        Tyr Ile Asp Pro Leu Pro Asp Leu Ile His Pro Arg Thr Gly Arg Leu
        545                 550                 555                 560
        His Thr Arg Phe Asn Gln Thr Ala Thr Ala Thr Gly Arg Leu Ser Ser
                            565                 570                 575
        Ser Asp Pro Asn Leu Gln Asn Ile Pro Val Arg Thr Pro Leu Gly Gln
                        580                 585                 590
        Arg Ile Arg Arg Ala Phe Ile Ala Glu Glu Gly Trp Leu Leu Val Ala
                    595                 600                 605
        Leu Asp Tyr Ser Gln Ile Glu Leu Arg Val Leu Ala His Leu Ser Gly
                610                 615                 620
        Asp Glu Asn Leu Ile Arg Val Phe Gln Glu Gly Arg Asp Ile His Thr
        625                 630                 635                 640
        Glu Thr Ala Ser Trp Met Phe Gly Val Pro Arg Glu Ala Val Asp Pro
                            645                 650                 655
        Leu Met Arg Arg Ala Ala Lys Thr Ile Asn Phe Gly Val Leu Tyr Gly
                        660                 665                 670
        Met Ser Ala His Arg Leu Ser Gln Glu Leu Ala Ile Pro Tyr Glu Glu
                    675                 680                 685
        Ala Gln Ala Phe Ile Glu Arg Tyr Phe Gln Ser Phe Pro Lys Val Arg
                690                 695                 700
        Ala Trp Ile Glu Lys Thr Leu Glu Glu Gly Arg Arg Arg Gly Tyr Val
        705                 710                 715                 720
        Glu Thr Leu Phe Gly Arg Arg Arg Tyr Val Pro Asp Leu Glu Ala Arg
                            725                 730                 735
        Val Lys Ser Val Arg Glu Ala Ala Glu Arg Met Ala Phe Asn Met Pro
                        740                 745                 750
        Val Gln Gly Thr Ala Ala Asp Leu Met Lys Leu Ala Met Val Lys Leu
                    755                 760                 765
        Phe Pro Arg Leu Glu Glu Met Gly Ala Arg Met Leu Leu Gln Val His
                770                 775                 780
        Asp Glu Leu Val Leu Glu Ala Pro Lys Glu Arg Ala Glu Ala Val Ala
        785                 790                 795                 800
        Arg Leu Ala Lys Glu Val Met Glu Gly Val Tyr Pro Leu Ala Val Pro
                            805                 810                 815
        Leu Glu Val Glu Val Gly Ile Gly Glu Asp Trp Leu Ser Ala Lys Glu
                        820                 825                 830

<210> SEQ ID NO 4
<211> LENGTH: 832
<212> TYPE: PRT
<213> ORGANISM: Artificial Sequence
<220> FEATURE:
<223> OTHER INFORMATION: Taq R487H

<400> SEQUENCE: 4

Met Arg Gly Met Leu Pro Leu Phe Glu Pro Lys Gly Arg Val Leu Leu
```

-continued

```
1               5                   10                  15
Val Asp Gly His His Leu Ala Tyr Arg Thr Phe His Ala Leu Lys Gly
                20                  25                  30
Leu Thr Thr Ser Arg Gly Glu Pro Val Gln Ala Val Tyr Gly Phe Ala
                35                  40                  45
Lys Ser Leu Leu Lys Ala Leu Lys Glu Asp Gly Asp Ala Val Ile Val
                50                  55                  60
Val Phe Asp Ala Lys Ala Pro Ser Phe Arg His Glu Ala Tyr Gly Gly
 65                 70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Leu Gly Leu Ala Arg Leu Glu
                100                 105                 110
Val Pro Gly Tyr Glu Ala Asp Asp Val Leu Ala Ser Leu Ala Lys Lys
                115                 120                 125
Ala Glu Lys Glu Gly Tyr Glu Val Arg Ile Leu Thr Ala Asp Lys Asp
                130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
                180                 185                 190
Leu Pro Gly Val Lys Gly Ile Gly Glu Lys Thr Ala Arg Lys Leu Leu
                195                 200                 205
Glu Glu Trp Gly Ser Leu Glu Ala Leu Leu Lys Asn Leu Asp Arg Leu
                210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
                260                 265                 270
Leu Glu Arg Leu Glu Phe Gly Ser Leu Leu His Glu Phe Gly Leu Leu
                275                 280                 285
Glu Ser Pro Lys Ala Leu Glu Glu Ala Pro Trp Pro Pro Pro Glu Gly
                290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
```

```
Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser His Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 5
<211> LENGTH: 832
```

<212> TYPE: PRT
<213> ORGANISM: Artificial Sequence
<220> FEATURE:
<223> OTHER INFORMATION: Taq K508W

<400> SEQUENCE: 5

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380
```

-continued

```
Thr Thr Pro Glu Gly Val Ala Arg Arg Tyr Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Trp Thr Gly Lys Arg
            500                 505                 510

Ser Thr Ser Ala Ala Val Leu Glu Ala Leu Arg Glu Ala His Pro Ile
    515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
    755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
```

Leu Glu Val Glu Val Gly Ile Gly Glu Asp Trp Leu Ser Ala Lys Glu
                805                 810                 815
            820                 825                 830

<210> SEQ ID NO 6
<211> LENGTH: 832
<212> TYPE: PRT
<213> ORGANISM: Artificial Sequence
<220> FEATURE:
<223> OTHER INFORMATION: Taq K508Y

<400> SEQUENCE: 6

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu

-continued

```
                340                 345                 350
Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
            370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
            405                 410                 415

Trp Gly Arg Leu Glu Gly Glu Arg Leu Leu Trp Leu Tyr Arg Glu
            420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
            450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Tyr Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765
```

```
Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830

<210> SEQ ID NO 7
<211> LENGTH: 832
<212> TYPE: PRT
<213> ORGANISM: Artificial Sequence
<220> FEATURE:
<223> OTHER INFORMATION: Taq R536K

<400> SEQUENCE: 7

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300
```

```
Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
            325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
            515                 520                 525

Val Glu Lys Ile Leu Gln Tyr Lys Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720
```

-continued

```
Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830
```

<210> SEQ ID NO 8
<211> LENGTH: 832
<212> TYPE: PRT
<213> ORGANISM: Artificial Sequence
<220> FEATURE:
<223> OTHER INFORMATION: Taq R536L

<400> SEQUENCE: 8

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255
```

```
Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
            355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Leu Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
        595                 600                 605

Leu Asp Tyr Ser Gln Ile Glu Leu Arg Val Leu Ala His Leu Ser Gly
    610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
```

```
                     675                 680                 685
Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Tyr Val Pro Asp Leu Glu Ala Arg
                    725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                    805                 810                 815

Leu Glu Val Glu Val Gly Ile Gly Glu Asp Trp Leu Ser Ala Lys Glu
                820                 825                 830

<210> SEQ ID NO 9
<211> LENGTH: 832
<212> TYPE: PRT
<213> ORGANISM: Artificial Sequence
<220> FEATURE:
<223> OTHER INFORMATION: Taq R587I

<400> SEQUENCE: 9

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
```

-continued

```
               210                 215                 220
Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
            275                 280                 285

Glu Ser Pro Lys Ala Leu Glu Ala Pro Trp Pro Pro Glu Gly
290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
                355                 360                 365

Pro Gly Asp Asp Pro Met Leu Leu Ala Tyr Leu Leu Asp Pro Ser Asn
370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
                515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Ile Thr Pro Leu Gly Gln
                580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
                610                 615                 620

Asp Glu Asn Leu Ile Arg Val Phe Gln Glu Gly Arg Asp Ile His Thr
625                 630                 635                 640
```

-continued

```
Glu Thr Ala Ser Trp Met Phe Gly Val Pro Arg Ala Val Asp Pro
                645                 650                 655
Leu Met Arg Arg Ala Ala Lys Thr Ile Asn Phe Gly Val Leu Tyr Gly
            660                 665                 670
Met Ser Ala His Arg Leu Ser Gln Glu Leu Ala Ile Pro Tyr Glu Glu
            675                 680                 685
Ala Gln Ala Phe Ile Glu Arg Tyr Phe Gln Ser Phe Pro Lys Val Arg
        690                 695                 700
Ala Trp Ile Glu Lys Thr Leu Glu Glu Gly Arg Arg Arg Gly Tyr Val
705                 710                 715                 720
Glu Thr Leu Phe Gly Arg Arg Tyr Val Pro Asp Leu Glu Ala Arg
                725                 730                 735
Val Lys Ser Val Arg Glu Ala Ala Glu Arg Met Ala Phe Asn Met Pro
            740                 745                 750
Val Gln Gly Thr Ala Ala Asp Leu Met Lys Leu Ala Met Val Lys Leu
            755                 760                 765
Phe Pro Arg Leu Glu Glu Met Gly Ala Arg Met Leu Leu Gln Val His
    770                 775                 780
Asp Glu Leu Val Leu Glu Ala Pro Lys Glu Arg Ala Glu Ala Val Ala
785                 790                 795                 800
Arg Leu Ala Lys Glu Val Met Glu Gly Val Tyr Pro Leu Ala Val Pro
                805                 810                 815
Leu Glu Val Glu Val Gly Ile Gly Glu Asp Trp Leu Ser Ala Lys Glu
                820                 825                 830

<210> SEQ ID NO 10
<211> LENGTH: 832
<212> TYPE: PRT
<213> ORGANISM: Artificial Sequence
<220> FEATURE:
<223> OTHER INFORMATION: Taq R587K

<400> SEQUENCE: 10

Met Arg Gly Met Leu Pro Leu Phe Glu Pro Lys Gly Arg Val Leu Leu
1               5                   10                  15
Val Asp Gly His His Leu Ala Tyr Arg Thr Phe His Ala Leu Lys Gly
                20                  25                  30
Leu Thr Thr Ser Arg Gly Glu Pro Val Gln Ala Val Tyr Gly Phe Ala
            35                  40                  45
Lys Ser Leu Leu Lys Ala Leu Lys Glu Asp Gly Asp Ala Val Ile Val
        50                  55                  60
Val Phe Asp Ala Lys Ala Pro Ser Phe Arg His Glu Ala Tyr Gly Gly
65                  70                  75                  80
Tyr Lys Ala Gly Arg Ala Pro Thr Pro Glu Asp Phe Pro Arg Gln Leu
                85                  90                  95
Ala Leu Ile Lys Glu Leu Val Asp Leu Leu Gly Leu Ala Arg Leu Glu
            100                 105                 110
Val Pro Gly Tyr Glu Ala Asp Asp Val Leu Ala Ser Leu Ala Lys Lys
        115                 120                 125
Ala Glu Lys Glu Gly Tyr Glu Val Arg Ile Leu Thr Ala Asp Lys Asp
    130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
```

-continued

```
Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Lys Thr Pro Leu Gly Gln
            580                 585                 590
```

```
Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 11
<211> LENGTH: 832
<212> TYPE: PRT
<213> ORGANISM: Artificial Sequence
<220> FEATURE:
<223> OTHER INFORMATION: Taq R660V

<400> SEQUENCE: 11

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125
```

-continued

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
    275                 280                 285

Glu Ser Pro Lys Ala Leu Glu Glu Ala Pro Trp Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu

```
                545                 550                 555                 560
His Thr Arg Phe Asn Gln Thr Ala Thr Ala Thr Gly Arg Leu Ser Ser
                    565                 570                 575

Ser Asp Pro Asn Leu Gln Asn Ile Pro Val Arg Thr Pro Leu Gly Gln
                580                 585                 590

Arg Ile Arg Arg Ala Phe Ile Ala Glu Glu Gly Trp Leu Leu Val Ala
                595                 600                 605

Leu Asp Tyr Ser Gln Ile Glu Leu Arg Val Leu Ala His Leu Ser Gly
                610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                    645                 650                 655

Leu Met Arg Val Ala Ala Lys Thr Ile Asn Phe Gly Val Leu Tyr Gly
                    660                 665                 670

Met Ser Ala His Arg Leu Ser Gln Glu Leu Ala Ile Pro Tyr Glu Glu
                    675                 680                 685

Ala Gln Ala Phe Ile Glu Arg Tyr Phe Gln Ser Phe Pro Lys Val Arg
                690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                    725                 730                 735

Val Lys Ser Val Arg Glu Ala Ala Glu Arg Met Ala Phe Asn Met Pro
                740                 745                 750

Val Gln Gly Thr Ala Ala Asp Leu Met Lys Leu Ala Met Val Lys Leu
                    755                 760                 765

Phe Pro Arg Leu Glu Glu Met Gly Ala Arg Met Leu Leu Gln Val His
                    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                    805                 810                 815

Leu Glu Val Glu Val Gly Ile Gly Glu Asp Trp Leu Ser Ala Lys Glu
                    820                 825                 830

<210> SEQ ID NO 12
<211> LENGTH: 832
<212> TYPE: PRT
<213> ORGANISM: Artificial Sequence
<220> FEATURE:
<223> OTHER INFORMATION: Taq R660T

<400> SEQUENCE: 12

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
```

```
                    85                  90                  95
Ala Leu Ile Lys Glu Leu Val Asp Leu Gly Leu Ala Arg Leu Glu
                100                 105                 110

Val Pro Gly Tyr Glu Ala Asp Val Leu Ala Ser Leu Ala Lys Lys
                115                 120                 125

Ala Glu Lys Glu Gly Tyr Glu Val Arg Ile Leu Thr Ala Lys Asp
                130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
                180                 185                 190

Leu Pro Gly Val Lys Gly Ile Gly Glu Lys Thr Ala Arg Lys Leu Leu
                195                 200                 205

Glu Glu Trp Gly Ser Leu Glu Ala Leu Leu Lys Asn Leu Asp Arg Leu
                210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
                260                 265                 270

Leu Glu Arg Leu Glu Phe Gly Ser Leu Leu His Glu Phe Gly Leu Leu
                275                 280                 285

Glu Ser Pro Lys Ala Leu Glu Glu Ala Pro Trp Pro Pro Pro Glu Gly
                290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
                340                 345                 350

Ala Lys Asp Leu Ser Val Leu Ala Leu Arg Glu Gly Leu Gly Leu Pro
                355                 360                 365

Pro Gly Asp Asp Pro Met Leu Leu Ala Tyr Leu Leu Asp Pro Ser Asn
                370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
                420                 425                 430

Val Glu Arg Pro Leu Ser Ala Val Leu Ala His Met Glu Ala Thr Gly
                435                 440                 445

Val Arg Leu Asp Val Ala Tyr Leu Arg Ala Leu Ser Leu Glu Val Ala
                450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510
```

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Arg Thr Pro Leu Gly Gln
        580                 585                 590

Arg Ile Arg Arg Ala Phe Ile Ala Glu Glu Gly Trp Leu Leu Val Ala
    595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Thr Ala Ala Lys Thr Ile Asn Phe Gly Val Leu Tyr Gly
        660                 665                 670

Met Ser Ala His Arg Leu Ser Gln Glu Leu Ala Ile Pro Tyr Glu Glu
    675                 680                 685

Ala Gln Ala Phe Ile Glu Arg Tyr Phe Gln Ser Phe Pro Lys Val Arg
        690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
        740                 745                 750

Val Gln Gly Thr Ala Ala Asp Leu Met Lys Leu Ala Met Val Lys Leu
    755                 760                 765

Phe Pro Arg Leu Glu Glu Met Gly Ala Arg Met Leu Leu Gln Val His
        770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
        820                 825                 830

<210> SEQ ID NO 13
<211> LENGTH: 832
<212> TYPE: PRT
<213> ORGANISM: Artificial Sequence
<220> FEATURE:
<223> OTHER INFORMATION: Taq VL22: K508Y, R587K, R660T

<400> SEQUENCE: 13

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

```
Lys Ser Leu Leu Lys Ala Leu Lys Glu Asp Gly Asp Ala Val Ile Val
         50                  55                  60
Val Phe Asp Ala Lys Ala Pro Ser Phe Arg His Glu Ala Tyr Gly Gly
 65                  70                  75                  80
Tyr Lys Ala Gly Arg Ala Pro Thr Pro Glu Asp Phe Pro Arg Gln Leu
                     85                  90                  95
Ala Leu Ile Lys Glu Leu Val Asp Leu Gly Leu Ala Arg Leu Glu
                100                 105                 110
Val Pro Gly Tyr Glu Ala Asp Val Leu Ala Ser Leu Ala Lys Lys
                115                 120                 125
Ala Glu Lys Glu Gly Tyr Glu Val Arg Ile Leu Thr Ala Asp Lys Asp
        130                 135                 140
Leu Tyr Gln Leu Leu Ser Asp Arg Ile His Val Leu His Pro Glu Gly
145                 150                 155                 160
Tyr Leu Ile Thr Pro Ala Trp Leu Trp Glu Lys Tyr Gly Leu Arg Pro
                165                 170                 175
Asp Gln Trp Ala Asp Tyr Arg Ala Leu Thr Gly Asp Glu Ser Asp Asn
                180                 185                 190
Leu Pro Gly Val Lys Gly Ile Gly Glu Lys Thr Ala Arg Lys Leu Leu
                195                 200                 205
Glu Glu Trp Gly Ser Leu Glu Ala Leu Leu Lys Asn Leu Asp Arg Leu
        210                 215                 220
Lys Pro Ala Ile Arg Glu Lys Ile Leu Ala His Met Asp Asp Leu Lys
225                 230                 235                 240
Leu Ser Trp Asp Leu Ala Lys Val Arg Thr Asp Leu Pro Leu Glu Val
                245                 250                 255
Asp Phe Ala Lys Arg Arg Glu Pro Asp Arg Glu Arg Leu Arg Ala Phe
                260                 265                 270
Leu Glu Arg Leu Glu Phe Gly Ser Leu Leu His Glu Phe Gly Leu Leu
                275                 280                 285
Glu Ser Pro Lys Ala Leu Glu Glu Ala Pro Trp Pro Pro Pro Glu Gly
        290                 295                 300
Ala Phe Val Gly Phe Val Leu Ser Arg Lys Glu Pro Met Trp Ala Asp
305                 310                 315                 320
Leu Leu Ala Leu Ala Ala Ala Arg Gly Gly Arg Val His Arg Ala Pro
                325                 330                 335
Glu Pro Tyr Lys Ala Leu Arg Asp Leu Lys Glu Ala Arg Gly Leu Leu
                340                 345                 350
Ala Lys Asp Leu Ser Val Leu Ala Leu Arg Glu Gly Leu Gly Leu Pro
                355                 360                 365
Pro Gly Asp Asp Pro Met Leu Leu Ala Tyr Leu Leu Asp Pro Ser Asn
        370                 375                 380
Thr Thr Pro Glu Gly Val Ala Arg Arg Tyr Gly Gly Glu Trp Thr Glu
385                 390                 395                 400
Glu Ala Gly Glu Arg Ala Ala Leu Ser Glu Arg Leu Phe Ala Asn Leu
                405                 410                 415
Trp Gly Arg Leu Glu Gly Glu Glu Arg Leu Leu Trp Leu Tyr Arg Glu
                420                 425                 430
Val Glu Arg Pro Leu Ser Ala Val Leu Ala His Met Glu Ala Thr Gly
                435                 440                 445
Val Arg Leu Asp Val Ala Tyr Leu Arg Ala Leu Ser Leu Glu Val Ala
        450                 455                 460
```

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
            485                 490                 495

Glu Leu Gly Leu Pro Ala Ile Gly Lys Thr Glu Tyr Thr Gly Lys Arg
            500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
            530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
            565                 570                 575

Ser Asp Pro Asn Leu Gln Asn Ile Pro Val Lys Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
            645                 650                 655

Leu Met Arg Thr Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
            725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
            820                 825                 830

<210> SEQ ID NO 14
<211> LENGTH: 557
<212> TYPE: PRT
<213> ORGANISM: Artificial Sequence
<220> FEATURE:
<223> OTHER INFORMATION: KTQ R210V

<400> SEQUENCE: 14

```
Met Arg Gly Ser His His His His His Thr Asp Pro His Ala Ala
1               5                   10                  15

Leu Glu Glu Ala Pro Trp Pro Pro Glu Gly Ala Phe Val Gly Phe
            20              25              30

Val Leu Ser Arg Lys Glu Pro Met Trp Ala Asp Leu Leu Ala Leu
            35              40              45

Ala Ala Arg Gly Gly Arg Val His Arg Ala Pro Glu Pro Tyr Lys Ala
    50              55              60

Leu Arg Asp Leu Lys Glu Ala Arg Gly Leu Leu Ala Lys Asp Leu Ser
65              70              75              80

Val Leu Ala Leu Arg Glu Gly Leu Gly Leu Pro Pro Gly Asp Asp Pro
                85              90              95

Met Leu Leu Ala Tyr Leu Leu Asp Pro Ser Asn Thr Thr Pro Glu Gly
            100             105             110

Val Ala Arg Arg Tyr Gly Gly Glu Trp Thr Glu Glu Ala Gly Glu Arg
            115             120             125

Ala Ala Leu Ser Glu Arg Leu Phe Ala Asn Leu Trp Gly Arg Leu Glu
    130             135             140

Gly Glu Glu Arg Leu Leu Trp Leu Tyr Arg Glu Val Glu Arg Pro Leu
145             150             155             160

Ser Ala Val Leu Ala His Met Glu Ala Thr Gly Val Arg Leu Asp Val
                165             170             175

Ala Tyr Leu Arg Ala Leu Ser Leu Glu Val Ala Glu Glu Ile Ala Arg
            180             185             190

Leu Glu Ala Glu Val Phe Arg Leu Ala Gly His Pro Phe Asn Leu Asn
    195             200             205

Ser Val Asp Gln Leu Glu Arg Val Leu Phe Asp Glu Leu Gly Leu Pro
    210             215             220

Ala Ile Gly Lys Thr Glu Lys Thr Gly Lys Arg Ser Thr Ser Ala Ala
225             230             235             240

Val Leu Glu Ala Leu Arg Glu Ala His Pro Ile Val Glu Lys Ile Leu
                245             250             255

Gln Tyr Arg Glu Leu Thr Lys Leu Lys Ser Thr Tyr Ile Asp Pro Leu
            260             265             270

Pro Asp Leu Ile His Pro Arg Thr Gly Arg Leu His Thr Arg Phe Asn
    275             280             285

Gln Thr Ala Thr Ala Thr Gly Arg Leu Ser Ser Ser Asp Pro Asn Leu
    290             295             300

Gln Asn Ile Pro Val Arg Thr Pro Leu Gly Gln Arg Ile Arg Arg Ala
305             310             315             320

Phe Ile Ala Glu Glu Gly Trp Leu Leu Val Ala Leu Asp Tyr Ser Gln
            325             330             335

Ile Glu Leu Arg Val Leu Ala His Leu Ser Gly Asp Glu Asn Leu Ile
            340             345             350

Arg Val Phe Gln Glu Gly Arg Asp Ile His Thr Glu Thr Ala Ser Trp
            355             360             365

Met Phe Gly Val Pro Arg Glu Ala Val Asp Pro Leu Met Arg Arg Ala
    370             375             380

Ala Lys Thr Ile Asn Phe Gly Val Leu Tyr Gly Met Ser Ala His Arg
385             390             395             400

Leu Ser Gln Glu Leu Ala Ile Pro Tyr Glu Glu Ala Gln Ala Phe Ile
            405             410             415

Glu Arg Tyr Phe Gln Ser Phe Pro Lys Val Arg Ala Trp Ile Glu Lys
```

```
               420                 425                 430
Thr Leu Glu Glu Gly Arg Arg Arg Gly Tyr Val Glu Thr Leu Phe Gly
            435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Arg Ala Glu Ala Val Ala Arg Leu Ala Lys Glu
        515                 520                 525

Val Met Glu Gly Val Tyr Pro Leu Ala Val Pro Leu Glu Val Glu Val
    530                 535                 540

Gly Ile Gly Glu Asp Trp Leu Ser Ala Lys Glu Lys Ala
545                 550                 555

<210> SEQ ID NO 15
<211> LENGTH: 557
<212> TYPE: PRT
<213> ORGANISM: Artificial Sequence
<220> FEATURE:
<223> OTHER INFORMATION: KTQ R210H

<400> SEQUENCE: 15

Met Arg Gly Ser His His His His His His Thr Asp Pro His Ala Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu Ala
        35                  40                  45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
        115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
        195                 200                 205

Ser His Asp Gln Leu Glu Arg Val Leu Phe Asp Glu Leu Gly Leu Pro
    210                 215                 220

Ala Ile Gly Lys Thr Glu Lys Thr Gly Lys Arg Ser Thr Ser Ala Ala
```

```
                225                 230                 235                 240
Val Leu Glu Ala Leu Arg Glu Ala His Pro Ile Val Glu Lys Ile Leu
                    245                 250                 255

Gln Tyr Arg Glu Leu Thr Lys Leu Lys Ser Thr Tyr Ile Asp Pro Leu
                260                 265                 270

Pro Asp Leu Ile His Pro Arg Thr Gly Arg Leu His Thr Arg Phe Asn
                275                 280                 285

Gln Thr Ala Thr Ala Thr Gly Arg Leu Ser Ser Asp Pro Asn Leu
            290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                    325                 330                 335

Ile Glu Leu Arg Val Leu Ala His Leu Ser Gly Asp Glu Asn Leu Ile
                340                 345                 350

Arg Val Phe Gln Glu Gly Arg Asp Ile His Thr Glu Thr Ala Ser Trp
                355                 360                 365

Met Phe Gly Val Pro Arg Glu Ala Val Asp Pro Leu Met Arg Arg Ala
                370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                    405                 410                 415

Glu Arg Tyr Phe Gln Ser Phe Pro Lys Val Arg Ala Trp Ile Glu Lys
                420                 425                 430

Thr Leu Glu Glu Gly Arg Arg Arg Gly Tyr Val Glu Thr Leu Phe Gly
                435                 440                 445

Arg Arg Arg Tyr Val Pro Asp Leu Glu Ala Arg Val Lys Ser Val Arg
                450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                    485                 490                 495

Glu Met Gly Ala Arg Met Leu Leu Gln Val His Asp Glu Leu Val Leu
                500                 505                 510

Glu Ala Pro Lys Glu Arg Ala Glu Ala Val Ala Arg Leu Ala Lys Glu
                515                 520                 525

Val Met Glu Gly Val Tyr Pro Leu Ala Val Pro Leu Glu Val Glu Val
                530                 535                 540

Gly Ile Gly Glu Asp Trp Leu Ser Ala Lys Glu Lys Ala
545                 550                 555

<210> SEQ ID NO 16
<211> LENGTH: 557
<212> TYPE: PRT
<213> ORGANISM: Artificial Sequence
<220> FEATURE:
<223> OTHER INFORMATION: KTQ K231W

<400> SEQUENCE: 16

Met Arg Gly Ser His His His His His His Thr Asp Pro His Ala Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Leu Ala Leu Ala
```

-continued

```
                35                  40                  45
Ala Ala Arg Gly Gly Arg Val His Arg Ala Pro Glu Pro Tyr Lys Ala
 50                  55                  60
Leu Arg Asp Leu Lys Glu Ala Arg Gly Leu Leu Ala Lys Asp Leu Ser
 65                  70                  75                  80
Val Leu Ala Leu Arg Glu Gly Leu Gly Leu Pro Pro Gly Asp Asp Pro
                 85                  90                  95
Met Leu Leu Ala Tyr Leu Leu Asp Pro Ser Asn Thr Thr Pro Glu Gly
                100                 105                 110
Val Ala Arg Arg Tyr Gly Gly Glu Trp Thr Glu Glu Ala Gly Glu Arg
                115                 120                 125
Ala Ala Leu Ser Glu Arg Leu Phe Ala Asn Leu Trp Gly Arg Leu Glu
                130                 135                 140
Gly Glu Glu Arg Leu Leu Trp Leu Tyr Arg Glu Val Glu Arg Pro Leu
145                 150                 155                 160
Ser Ala Val Leu Ala His Met Glu Ala Thr Gly Val Arg Leu Asp Val
                165                 170                 175
Ala Tyr Leu Arg Ala Leu Ser Leu Glu Val Ala Glu Glu Ile Ala Arg
                180                 185                 190
Leu Glu Ala Glu Val Phe Arg Leu Ala Gly His Pro Phe Asn Leu Asn
                195                 200                 205
Ser Arg Asp Gln Leu Glu Arg Val Leu Phe Asp Glu Leu Gly Leu Pro
210                 215                 220
Ala Ile Gly Lys Thr Glu Trp Thr Gly Lys Arg Ser Thr Ser Ala Ala
225                 230                 235                 240
Val Leu Glu Ala Leu Arg Glu Ala His Pro Ile Val Glu Lys Ile Leu
                245                 250                 255
Gln Tyr Arg Glu Leu Thr Lys Leu Lys Ser Thr Tyr Ile Asp Pro Leu
                260                 265                 270
Pro Asp Leu Ile His Pro Arg Thr Gly Arg Leu His Thr Arg Phe Asn
                275                 280                 285
Gln Thr Ala Thr Ala Thr Gly Arg Leu Ser Ser Ser Asp Pro Asn Leu
                290                 295                 300
Gln Asn Ile Pro Val Arg Thr Pro Leu Gly Gln Arg Ile Arg Arg Ala
305                 310                 315                 320
Phe Ile Ala Glu Glu Gly Trp Leu Leu Val Ala Leu Asp Tyr Ser Gln
                325                 330                 335
Ile Glu Leu Arg Val Leu Ala His Leu Ser Gly Asp Glu Asn Leu Ile
                340                 345                 350
Arg Val Phe Gln Glu Gly Arg Asp Ile His Thr Glu Thr Ala Ser Trp
                355                 360                 365
Met Phe Gly Val Pro Arg Glu Ala Val Asp Pro Leu Met Arg Arg Ala
                370                 375                 380
Ala Lys Thr Ile Asn Phe Gly Val Leu Tyr Gly Met Ser Ala His Arg
385                 390                 395                 400
Leu Ser Gln Glu Leu Ala Ile Pro Tyr Glu Glu Ala Gln Ala Phe Ile
                405                 410                 415
Glu Arg Tyr Phe Gln Ser Phe Pro Lys Val Arg Ala Trp Ile Glu Lys
                420                 425                 430
Thr Leu Glu Glu Gly Arg Arg Gly Tyr Val Glu Thr Leu Phe Gly
                435                 440                 445
Arg Arg Arg Tyr Val Pro Asp Leu Glu Ala Arg Val Lys Ser Val Arg
450                 455                 460
```

```
Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
            485                 490                 495

Glu Met Gly Ala Arg Met Leu Leu Gln Val His Asp Glu Leu Val Leu
        500                 505                 510

Glu Ala Pro Lys Glu Arg Ala Glu Ala Val Ala Arg Leu Ala Lys Glu
    515                 520                 525

Val Met Glu Gly Val Tyr Pro Leu Ala Val Pro Leu Glu Val Glu Val
530                 535                 540

Gly Ile Gly Glu Asp Trp Leu Ser Ala Lys Glu Lys Ala
545                 550                 555
```

<210> SEQ ID NO 17
<211> LENGTH: 557
<212> TYPE: PRT
<213> ORGANISM: Artificial Sequence
<220> FEATURE:
<223> OTHER INFORMATION: KTQ K231Y

<400> SEQUENCE: 17

```
Met Arg Gly Ser His His His His His His Thr Asp Pro His Ala Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu Ala
        35                  40                  45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
        115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
        195                 200                 205

Ser Arg Asp Gln Leu Glu Arg Val Leu Phe Asp Glu Leu Gly Leu Pro
    210                 215                 220

Ala Ile Gly Lys Thr Glu Tyr Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270
```

```
Pro Asp Leu Ile His Pro Arg Thr Gly Arg Leu His Thr Arg Phe Asn
        275                 280                 285

Gln Thr Ala Thr Ala Thr Gly Arg Leu Ser Ser Ser Asp Pro Asn Leu
290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
        355                 360                 365

Met Phe Gly Val Pro Arg Glu Ala Val Asp Pro Leu Met Arg Arg Ala
370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
        435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Arg Ala Glu Ala Val Ala Arg Leu Ala Lys Glu
        515                 520                 525

Val Met Glu Gly Val Tyr Pro Leu Ala Val Pro Leu Glu Val Glu Val
530                 535                 540

Gly Ile Gly Glu Asp Trp Leu Ser Ala Lys Glu Lys Ala
545                 550                 555

<210> SEQ ID NO 18
<211> LENGTH: 557
<212> TYPE: PRT
<213> ORGANISM: Artificial Sequence
<220> FEATURE:
<223> OTHER INFORMATION: KTQ R259K

<400> SEQUENCE: 18

Met Arg Gly Ser His His His His His His Thr Asp Pro His Ala Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Leu Ala Leu Ala
            35                  40                  45

Ala Ala Arg Gly Gly Arg Val His Arg Ala Pro Glu Pro Tyr Lys Ala
        50                  55                  60

Leu Arg Asp Leu Lys Glu Ala Arg Gly Leu Leu Ala Lys Asp Leu Ser
65                  70                  75                  80
```

```
Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
                115                 120                 125

Ala Ala Leu Ser Glu Arg Leu Phe Ala Asn Leu Trp Gly Arg Leu Glu
                130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
                180                 185                 190

Leu Glu Ala Glu Val Phe Arg Leu Ala Gly His Pro Phe Asn Leu Asn
                195                 200                 205

Ser Arg Asp Gln Leu Glu Arg Val Leu Phe Asp Glu Leu Gly Leu Pro
                210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Lys Glu Leu Thr Lys Leu Lys Ser Thr Tyr Ile Asp Pro Leu
                260                 265                 270

Pro Asp Leu Ile His Pro Arg Thr Gly Arg Leu His Thr Arg Phe Asn
                275                 280                 285

Gln Thr Ala Thr Ala Thr Gly Arg Leu Ser Ser Ser Asp Pro Asn Leu
                290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
                340                 345                 350

Arg Val Phe Gln Glu Gly Arg Asp Ile His Thr Glu Thr Ala Ser Trp
                355                 360                 365

Met Phe Gly Val Pro Arg Glu Ala Val Asp Pro Leu Met Arg Arg Ala
                370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
                420                 425                 430

Thr Leu Glu Glu Gly Arg Arg Arg Gly Tyr Val Glu Thr Leu Phe Gly
                435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495
```

```
Glu Met Gly Ala Arg Met Leu Leu Gln Val His Asp Glu Leu Val Leu
                500                 505                 510
Glu Ala Pro Lys Glu Arg Ala Glu Ala Val Ala Arg Leu Ala Lys Glu
            515                 520                 525
Val Met Glu Gly Val Tyr Pro Leu Ala Val Pro Leu Glu Val Glu Val
        530                 535                 540
Gly Ile Gly Glu Asp Trp Leu Ser Ala Lys Glu Lys Ala
545                 550                 555

<210> SEQ ID NO 19
<211> LENGTH: 557
<212> TYPE: PRT
<213> ORGANISM: Artificial Sequence
<220> FEATURE:
<223> OTHER INFORMATION: KTQ R259L

<400> SEQUENCE: 19

Met Arg Gly Ser His His His His His His Thr Asp Pro His Ala Ala
1               5                   10                  15
Leu Glu Glu Ala Pro Trp Pro Pro Glu Gly Ala Phe Val Gly Phe
            20                  25                  30
Val Leu Ser Arg Lys Glu Pro Met Trp Ala Asp Leu Leu Ala Leu Ala
        35                  40                  45
Ala Ala Arg Gly Gly Arg Val His Arg Ala Pro Glu Pro Tyr Lys Ala
    50                  55                  60
Leu Arg Asp Leu Lys Glu Ala Arg Gly Leu Leu Ala Lys Asp Leu Ser
65                  70                  75                  80
Val Leu Ala Leu Arg Glu Gly Leu Gly Leu Pro Pro Gly Asp Asp Pro
                85                  90                  95
Met Leu Leu Ala Tyr Leu Leu Asp Pro Ser Asn Thr Thr Pro Glu Gly
            100                 105                 110
Val Ala Arg Arg Tyr Gly Gly Glu Trp Thr Glu Glu Ala Gly Glu Arg
        115                 120                 125
Ala Ala Leu Ser Glu Arg Leu Phe Ala Asn Leu Trp Gly Arg Leu Glu
    130                 135                 140
Gly Glu Glu Arg Leu Leu Trp Leu Tyr Arg Glu Val Glu Arg Pro Leu
145                 150                 155                 160
Ser Ala Val Leu Ala His Met Glu Ala Thr Gly Val Arg Leu Asp Val
                165                 170                 175
Ala Tyr Leu Arg Ala Leu Ser Leu Glu Val Ala Glu Glu Ile Ala Arg
            180                 185                 190
Leu Glu Ala Glu Val Phe Arg Leu Ala Gly His Pro Phe Asn Leu Asn
        195                 200                 205
Ser Arg Asp Gln Leu Glu Arg Val Leu Phe Asp Glu Leu Gly Leu Pro
    210                 215                 220
Ala Ile Gly Lys Thr Glu Lys Thr Gly Lys Arg Ser Thr Ser Ala Ala
225                 230                 235                 240
Val Leu Glu Ala Leu Arg Glu Ala His Pro Ile Val Glu Lys Ile Leu
                245                 250                 255
Gln Tyr Leu Glu Leu Thr Lys Leu Lys Ser Thr Tyr Ile Asp Pro Leu
            260                 265                 270
Pro Asp Leu Ile His Pro Arg Thr Gly Arg Leu His Thr Arg Phe Asn
        275                 280                 285
Gln Thr Ala Thr Ala Thr Gly Arg Leu Ser Ser Ser Asp Pro Asn Leu
    290                 295                 300
```

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
        355                 360                 365

Met Phe Gly Val Pro Arg Glu Ala Val Asp Pro Leu Met Arg Arg Ala
    370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Gly Tyr Val Glu Thr Leu Phe Gly
        435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Arg Ala Glu Ala Val Ala Arg Leu Ala Lys Glu
        515                 520                 525

Val Met Glu Gly Val Tyr Pro Leu Ala Val Pro Leu Glu Val Glu Val
    530                 535                 540

Gly Ile Gly Glu Asp Trp Leu Ser Ala Lys Glu Lys Ala
545                 550                 555

<210> SEQ ID NO 20
<211> LENGTH: 557
<212> TYPE: PRT
<213> ORGANISM: Artificial Sequence
<220> FEATURE:
<223> OTHER INFORMATION: KTQ R310L

<400> SEQUENCE: 20

Met Arg Gly Ser His His His His His His Thr Asp Pro His Ala Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Leu Ala Leu Ala
            35                  40                  45

Ala Ala Arg Gly Gly Arg Val His Arg Ala Pro Glu Pro Tyr Lys Ala
        50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
            100                 105                 110

```
Val Ala Arg Arg Tyr Gly Gly Glu Trp Thr Glu Ala Gly Glu Arg
            115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Ile Ala Arg
            180                 185                 190

Leu Glu Ala Glu Val Phe Arg Leu Ala Gly His Pro Phe Asn Leu Asn
    195                 200                 205

Ser Arg Asp Gln Leu Glu Arg Val Leu Phe Asp Glu Leu Gly Leu Pro
210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
            245                 250                 255

Gln Tyr Arg Glu Leu Thr Lys Leu Lys Ser Thr Tyr Ile Asp Pro Leu
    260                 265                 270

Pro Asp Leu Ile His Pro Arg Thr Gly Arg Leu His Thr Arg Phe Asn
    275                 280                 285

Gln Thr Ala Thr Ala Thr Gly Arg Leu Ser Ser Ser Asp Pro Asn Leu
    290                 295                 300

Gln Asn Ile Pro Val Leu Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
            355                 360                 365

Met Phe Gly Val Pro Arg Glu Ala Val Asp Pro Leu Met Arg Arg Ala
    370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
            435                 440                 445

Arg Arg Arg Tyr Val Pro Asp Leu Glu Ala Arg Val Lys Ser Val Arg
    450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Arg Ala Glu Ala Val Ala Arg Leu Ala Lys Glu
            515                 520                 525

Val Met Glu Gly Val Tyr Pro Leu Ala Val Pro Leu Glu Val Glu Val
```

```
                530                 535                 540
Gly Ile Gly Glu Asp Trp Leu Ser Ala Lys Glu Lys Ala
545                 550                 555

<210> SEQ ID NO 21
<211> LENGTH: 557
<212> TYPE: PRT
<213> ORGANISM: Artificial Sequence
<220> FEATURE:
<223> OTHER INFORMATION: KTQ R310I

<400> SEQUENCE: 21

Met Arg Gly Ser His His His His His Thr Asp Pro His Ala Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Leu Ala Leu
                35                  40                  45

Ala Ala Arg Gly Gly Arg Val His Arg Ala Pro Glu Pro Tyr Lys Ala
            50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
                115                 120                 125

Ala Ala Leu Ser Glu Arg Leu Phe Ala Asn Leu Trp Gly Arg Leu Glu
            130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
                180                 185                 190

Leu Glu Ala Glu Val Phe Arg Leu Ala Gly His Pro Phe Asn Leu Asn
                195                 200                 205

Ser Arg Asp Gln Leu Glu Arg Val Leu Phe Asp Glu Leu Gly Leu Pro
            210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
                260                 265                 270

Pro Asp Leu Ile His Pro Arg Thr Gly Arg Leu His Thr Arg Phe Asn
                275                 280                 285

Gln Thr Ala Thr Ala Thr Gly Arg Leu Ser Ser Ser Asp Pro Asn Leu
            290                 295                 300

Gln Asn Ile Pro Val Ile Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
```

```
                340                 345                 350
Arg Val Phe Gln Glu Gly Arg Asp Ile His Thr Glu Thr Ala Ser Trp
        355                 360                 365
Met Phe Gly Val Pro Arg Glu Ala Val Asp Pro Leu Met Arg Arg Ala
    370                 375                 380
Ala Lys Thr Ile Asn Phe Gly Val Leu Tyr Gly Met Ser Ala His Arg
385                 390                 395                 400
Leu Ser Gln Glu Leu Ala Ile Pro Tyr Glu Glu Ala Gln Ala Phe Ile
                405                 410                 415
Glu Arg Tyr Phe Gln Ser Phe Pro Lys Val Arg Ala Trp Ile Glu Lys
            420                 425                 430
Thr Leu Glu Glu Gly Arg Arg Gly Tyr Val Glu Thr Leu Phe Gly
        435                 440                 445
Arg Arg Arg Tyr Val Pro Asp Leu Glu Ala Arg Val Lys Ser Val Arg
    450                 455                 460
Glu Ala Ala Glu Arg Met Ala Phe Asn Met Pro Val Gln Gly Thr Ala
465                 470                 475                 480
Ala Asp Leu Met Lys Leu Ala Met Val Lys Leu Phe Pro Arg Leu Glu
                485                 490                 495
Glu Met Gly Ala Arg Met Leu Leu Gln Val His Asp Glu Leu Val Leu
            500                 505                 510
Glu Ala Pro Lys Glu Arg Ala Glu Ala Val Ala Arg Leu Ala Lys Glu
        515                 520                 525
Val Met Glu Gly Val Tyr Pro Leu Ala Val Pro Leu Glu Val Glu Val
    530                 535                 540
Gly Ile Gly Glu Asp Trp Leu Ser Ala Lys Glu Lys Ala
545                 550                 555

<210> SEQ ID NO 22
<211> LENGTH: 557
<212> TYPE: PRT
<213> ORGANISM: Artificial Sequence
<220> FEATURE:
<223> OTHER INFORMATION: KTQ R383V

<400> SEQUENCE: 22

Met Arg Gly Ser His His His His His His Thr Asp Pro His Ala Ala
1               5                   10                  15
Leu Glu Glu Ala Pro Trp Pro Pro Glu Gly Ala Phe Val Gly Phe
            20                  25                  30
Val Leu Ser Arg Lys Glu Pro Met Trp Ala Asp Leu Leu Ala Leu Ala
        35                  40                  45
Ala Ala Arg Gly Gly Arg Val His Arg Ala Pro Glu Pro Tyr Lys Ala
    50                  55                  60
Leu Arg Asp Leu Lys Glu Ala Arg Gly Leu Leu Ala Lys Asp Leu Ser
65                  70                  75                  80
Val Leu Ala Leu Arg Glu Gly Leu Gly Leu Pro Pro Gly Asp Asp Pro
                85                  90                  95
Met Leu Leu Ala Tyr Leu Leu Asp Pro Ser Asn Thr Thr Pro Glu Gly
            100                 105                 110
Val Ala Arg Arg Tyr Gly Gly Glu Trp Thr Glu Glu Ala Gly Glu Arg
        115                 120                 125
Ala Ala Leu Ser Glu Arg Leu Phe Ala Asn Leu Trp Gly Arg Leu Glu
    130                 135                 140
Gly Glu Glu Arg Leu Leu Trp Leu Tyr Arg Glu Val Glu Arg Pro Leu
```

```
         145                 150                 155                 160
        Ser Ala Val Leu Ala His Met Glu Ala Thr Gly Val Arg Leu Asp Val
                        165                 170                 175

Ala Tyr Leu Arg Ala Leu Ser Leu Glu Val Ala Glu Ile Ala Arg
                        180                 185                 190

Leu Glu Ala Glu Val Phe Arg Leu Ala Gly His Pro Phe Asn Leu Asn
                        195                 200                 205

Ser Arg Asp Gln Leu Glu Arg Val Leu Phe Asp Glu Leu Gly Leu Pro
        210                 215                 220

Ala Ile Gly Lys Thr Glu Lys Thr Gly Lys Arg Ser Thr Ser Ala Ala
        225                 230                 235                 240

Val Leu Glu Ala Leu Arg Glu Ala His Pro Ile Val Glu Lys Ile Leu
                        245                 250                 255

Gln Tyr Arg Glu Leu Thr Lys Leu Lys Ser Thr Tyr Ile Asp Pro Leu
                        260                 265                 270

Pro Asp Leu Ile His Pro Arg Thr Gly Arg Leu His Thr Arg Phe Asn
                        275                 280                 285

Gln Thr Ala Thr Ala Thr Gly Arg Leu Ser Ser Asp Pro Asn Leu
                        290                 295                 300

Gln Asn Ile Pro Val Arg Thr Pro Leu Gly Gln Arg Ile Arg Arg Ala
        305                 310                 315                 320

Phe Ile Ala Glu Glu Gly Trp Leu Leu Val Ala Leu Asp Tyr Ser Gln
                        325                 330                 335

Ile Glu Leu Arg Val Leu Ala His Leu Ser Gly Asp Glu Asn Leu Ile
                        340                 345                 350

Arg Val Phe Gln Glu Gly Arg Asp Ile His Thr Glu Thr Ala Ser Trp
                        355                 360                 365

Met Phe Gly Val Pro Arg Glu Ala Val Asp Pro Leu Met Arg Val Ala
                        370                 375                 380

Ala Lys Thr Ile Asn Phe Gly Val Leu Tyr Gly Met Ser Ala His Arg
        385                 390                 395                 400

Leu Ser Gln Glu Leu Ala Ile Pro Tyr Glu Glu Ala Gln Ala Phe Ile
                        405                 410                 415

Glu Arg Tyr Phe Gln Ser Phe Pro Lys Val Arg Ala Trp Ile Glu Lys
                        420                 425                 430

Thr Leu Glu Glu Gly Arg Arg Arg Gly Tyr Val Glu Thr Leu Phe Gly
                        435                 440                 445

Arg Arg Arg Tyr Val Pro Asp Leu Glu Ala Arg Val Lys Ser Val Arg
        450                 455                 460

Glu Ala Ala Glu Arg Met Ala Phe Asn Met Pro Val Gln Gly Thr Ala
        465                 470                 475                 480

Ala Asp Leu Met Lys Leu Ala Met Val Lys Leu Phe Pro Arg Leu Glu
                        485                 490                 495

Glu Met Gly Ala Arg Met Leu Leu Gln Val His Asp Glu Leu Val Leu
                        500                 505                 510

Glu Ala Pro Lys Glu Arg Ala Glu Ala Val Ala Arg Leu Ala Lys Glu
                        515                 520                 525

Val Met Glu Gly Val Tyr Pro Leu Ala Val Pro Leu Glu Val Glu Val
                        530                 535                 540

Gly Ile Gly Glu Asp Trp Leu Ser Ala Lys Glu Lys Ala
        545                 550                 555

<210> SEQ ID NO 23
```

```
<211> LENGTH: 557
<212> TYPE: PRT
<213> ORGANISM: Artificial Sequence
<220> FEATURE:
<223> OTHER INFORMATION: KTQ R383T

<400> SEQUENCE: 23
```

| | | | | | | | | | | | | | | | |
|---|---|---|---|---|---|---|---|---|---|---|---|---|---|---|---|
| Met | Arg | Gly | Ser | His | His | His | His | His | Thr | Asp | Pro | His | Ala | Ala |
| 1 | | | | 5 | | | | | 10 | | | | | 15 |
| Leu | Glu | Glu | Ala | Pro | Trp | Pro | Pro | Glu | Gly | Ala | Phe | Val | Gly | Phe |
| | | | 20 | | | | | 25 | | | | | 30 | |
| Val | Leu | Ser | Arg | Lys | Glu | Pro | Met | Trp | Ala | Asp | Leu | Leu | Ala | Leu | Ala |
| | | 35 | | | | | 40 | | | | | 45 | | | |
| Ala | Ala | Arg | Gly | Gly | Arg | Val | His | Arg | Ala | Pro | Glu | Pro | Tyr | Lys | Ala |
| | 50 | | | | | 55 | | | | | 60 | | | | |
| Leu | Arg | Asp | Leu | Lys | Glu | Ala | Arg | Gly | Leu | Leu | Ala | Lys | Asp | Leu | Ser |
| 65 | | | | | 70 | | | | | 75 | | | | | 80 |
| Val | Leu | Ala | Leu | Arg | Glu | Gly | Leu | Gly | Leu | Pro | Pro | Gly | Asp | Asp | Pro |
| | | | | 85 | | | | | 90 | | | | | 95 | |
| Met | Leu | Leu | Ala | Tyr | Leu | Leu | Asp | Pro | Ser | Asn | Thr | Thr | Pro | Glu | Gly |
| | | | 100 | | | | | 105 | | | | | 110 | | |
| Val | Ala | Arg | Arg | Tyr | Gly | Gly | Glu | Trp | Thr | Glu | Glu | Ala | Gly | Glu | Arg |
| | | | 115 | | | | | 120 | | | | | 125 | | |
| Ala | Ala | Leu | Ser | Glu | Arg | Leu | Phe | Ala | Asn | Leu | Trp | Gly | Arg | Leu | Glu |
| | 130 | | | | | 135 | | | | | 140 | | | | |
| Gly | Glu | Glu | Arg | Leu | Leu | Trp | Leu | Tyr | Arg | Glu | Val | Glu | Arg | Pro | Leu |
| 145 | | | | | 150 | | | | | 155 | | | | | 160 |
| Ser | Ala | Val | Leu | Ala | His | Met | Glu | Ala | Thr | Gly | Val | Arg | Leu | Asp | Val |
| | | | | 165 | | | | | 170 | | | | | 175 | |
| Ala | Tyr | Leu | Arg | Ala | Leu | Ser | Leu | Glu | Val | Ala | Glu | Glu | Ile | Ala | Arg |
| | | | 180 | | | | | 185 | | | | | 190 | | |
| Leu | Glu | Ala | Glu | Val | Phe | Arg | Leu | Ala | Gly | His | Pro | Phe | Asn | Leu | Asn |
| | | 195 | | | | | 200 | | | | | 205 | | | |
| Ser | Arg | Asp | Gln | Leu | Glu | Arg | Val | Leu | Phe | Asp | Glu | Leu | Gly | Leu | Pro |
| | 210 | | | | | 215 | | | | | 220 | | | | |
| Ala | Ile | Gly | Lys | Thr | Glu | Lys | Thr | Gly | Lys | Arg | Ser | Thr | Ser | Ala | Ala |
| 225 | | | | | 230 | | | | | 235 | | | | | 240 |
| Val | Leu | Glu | Ala | Leu | Arg | Glu | Ala | His | Pro | Ile | Val | Glu | Lys | Ile | Leu |
| | | | | 245 | | | | | 250 | | | | | 255 | |
| Gln | Tyr | Arg | Glu | Leu | Thr | Lys | Leu | Lys | Ser | Thr | Tyr | Ile | Asp | Pro | Leu |
| | | | 260 | | | | | 265 | | | | | 270 | | |
| Pro | Asp | Leu | Ile | His | Pro | Arg | Thr | Gly | Arg | Leu | His | Thr | Arg | Phe | Asn |
| | | 275 | | | | | 280 | | | | | 285 | | | |
| Gln | Thr | Ala | Thr | Ala | Thr | Gly | Arg | Leu | Ser | Ser | Asp | Pro | Asn | Leu |
| | 290 | | | | | 295 | | | | | 300 | | | | |
| Gln | Asn | Ile | Pro | Val | Arg | Thr | Pro | Leu | Gly | Gln | Arg | Ile | Arg | Arg | Ala |
| 305 | | | | | 310 | | | | | 315 | | | | | 320 |
| Phe | Ile | Ala | Glu | Glu | Gly | Trp | Leu | Leu | Val | Ala | Leu | Asp | Tyr | Ser | Gln |
| | | | | 325 | | | | | 330 | | | | | 335 | |
| Ile | Glu | Leu | Arg | Val | Leu | Ala | His | Leu | Ser | Gly | Asp | Glu | Asn | Leu | Ile |
| | | | 340 | | | | | 345 | | | | | 350 | | |
| Arg | Val | Phe | Gln | Glu | Gly | Arg | Asp | Ile | His | Thr | Glu | Thr | Ala | Ser | Trp |
| | | 355 | | | | | 360 | | | | | 365 | | | |
| Met | Phe | Gly | Val | Pro | Arg | Glu | Ala | Val | Asp | Pro | Leu | Met | Arg | Thr | Ala |
| | 370 | | | | | 375 | | | | | 380 | | | | |

```
Ala Lys Thr Ile Asn Phe Gly Val Leu Tyr Gly Met Ser Ala His Arg
385                 390                 395                 400

Leu Ser Gln Glu Leu Ala Ile Pro Tyr Glu Ala Gln Ala Phe Ile
            405                 410                 415

Glu Arg Tyr Phe Gln Ser Phe Pro Lys Val Arg Ala Trp Ile Glu Lys
            420                 425                 430

Thr Leu Glu Glu Gly Arg Arg Gly Tyr Val Glu Thr Leu Phe Gly
            435                 440                 445

Arg Arg Arg Tyr Val Pro Asp Leu Glu Ala Arg Val Lys Ser Val Arg
            450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
                500                 505                 510

Glu Ala Pro Lys Glu Arg Ala Glu Ala Val Ala Arg Leu Ala Lys Glu
                515                 520                 525

Val Met Glu Gly Val Tyr Pro Leu Ala Val Pro Leu Glu Val Glu Val
530                 535                 540

Gly Ile Gly Glu Asp Trp Leu Ser Ala Lys Glu Lys Ala
545                 550                 555

<210> SEQ ID NO 24
<211> LENGTH: 557
<212> TYPE: PRT
<213> ORGANISM: Artificial Sequence
<220> FEATURE:
<223> OTHER INFORMATION: KTQ VL22: K231Y, R310K, R383T

<400> SEQUENCE: 24

Met Arg Gly Ser His His His His His His Thr Asp Pro His Ala Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu Ala
            35                  40                  45

Ala Ala Arg Gly Gly Arg Val His Arg Ala Pro Glu Pro Tyr Lys Ala
            50                  55                  60

Leu Arg Asp Leu Lys Glu Ala Arg Gly Leu Leu Ala Lys Asp Leu Ser
65              70                  75                  80

Val Leu Ala Leu Arg Glu Gly Leu Gly Leu Pro Pro Gly Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
                115                 120                 125

Ala Ala Leu Ser Glu Arg Leu Phe Ala Asn Leu Trp Gly Arg Leu Glu
                130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
                180                 185                 190
```

Leu Glu Ala Glu Val Phe Arg Leu Ala Gly His Pro Phe Asn Leu Asn
            195                 200                 205

Ser Arg Asp Gln Leu Glu Arg Val Leu Phe Asp Glu Leu Gly Leu Pro
        210                 215                 220

Ala Ile Gly Lys Thr Glu Tyr Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270

Pro Asp Leu Ile His Pro Arg Thr Gly Arg Leu His Thr Arg Phe Asn
        275                 280                 285

Gln Thr Ala Thr Ala Thr Gly Arg Leu Ser Ser Ser Asp Pro Asn Leu
290                 295                 300

Gln Asn Ile Pro Val Lys Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
            325                 330                 335

Ile Glu Leu Arg Val Leu Ala His Leu Ser Gly Asp Glu Asn Leu Ile
        340                 345                 350

Arg Val Phe Gln Glu Gly Arg Asp Ile His Thr Glu Thr Ala Ser Trp
            355                 360                 365

Met Phe Gly Val Pro Arg Glu Ala Val Asp Pro Leu Met Arg Thr Ala
        370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
        435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Arg Ala Glu Ala Val Ala Arg Leu Ala Lys Glu
        515                 520                 525

Val Met Glu Gly Val Tyr Pro Leu Ala Val Pro Leu Glu Val Glu Val
530                 535                 540

Gly Ile Gly Glu Asp Trp Leu Ser Ala Lys Glu Lys Ala
545                 550                 555

<210> SEQ ID NO 25
<211> LENGTH: 20
<212> TYPE: DNA
<213> ORGANISM: Artificial Sequence
<220> FEATURE:
<223> OTHER INFORMATION: F20-for

<400> SEQUENCE: 25
cgttggtcct gaaggaggat                                              20

<210> SEQ ID NO 26
<211> LENGTH: 20
<212> TYPE: DNA
<213> ORGANISM: Artificial Sequence
<220> FEATURE:
<223> OTHER INFORMATION: F20-rev

<400> SEQUENCE: 26
cgcgcagcac gcgccgccgt                                              20

<210> SEQ ID NO 27
<211> LENGTH: 90
<212> TYPE: DNA
<213> ORGANISM: Artificial Sequence
<220> FEATURE:
<223> OTHER INFORMATION: F90A

<400> SEQUENCE: 27
ccgtcagctg tgccgtcgcg cagcacgcgc cgccgtggac agaggactgc agaaaatcaa  60
cctatcctcc ttcaggacca acgtacagag                                   90

<210> SEQ ID NO 28
<211> LENGTH: 90
<212> TYPE: DNA
<213> ORGANISM: Artificial Sequence
<220> FEATURE:
<223> OTHER INFORMATION: F90G

<400> SEQUENCE: 28
ccgtcagctg tgccgtcgcg cagcacgcgc cgccgtggac agaggactgc agaaaatcaa  60
cctgtcctcc ttcaggacca acgtacagag                                   90

<210> SEQ ID NO 29
<211> LENGTH: 20
<212> TYPE: DNA
<213> ORGANISM: Artificial Sequence
<220> FEATURE:
<223> OTHER INFORMATION: DNA primer

<400> SEQUENCE: 29
cgttggtcct gaaggaggat                                              20

<210> SEQ ID NO 30
<211> LENGTH: 33
<212> TYPE: DNA
<213> ORGANISM: Artificial Sequence
<220> FEATURE:
<223> OTHER INFORMATION: template F33A

<400> SEQUENCE: 30
aaatcaacct atcctccttc aggaccaacg tac                               33

<210> SEQ ID NO 31
<211> LENGTH: 33
<212> TYPE: DNA
<213> ORGANISM: Artificial Sequence
<220> FEATURE:
<223> OTHER INFORMATION: F33G

<400> SEQUENCE: 31
aaatcaacct gtcctccttc aggaccaacg tac                               33

<210> SEQ ID NO 32
<211> LENGTH: 20
<212> TYPE: DNA
<213> ORGANISM: Artificial Sequence
<220> FEATURE:
<223> OTHER INFORMATION: F20-for

<400> SEQUENCE: 32
cgttggtcct gaaggaggat                                              20

<210> SEQ ID NO 33
<211> LENGTH: 20
<212> TYPE: DNA
<213> ORGANISM: Artificial Sequence
<220> FEATURE:
<223> OTHER INFORMATION: F20-rev

<400> SEQUENCE: 33
cgcgcagcac gcgccgccgt                                              20

<210> SEQ ID NO 34
<211> LENGTH: 90
<212> TYPE: DNA
<213> ORGANISM: Artificial Sequence
<220> FEATURE:
<223> OTHER INFORMATION: F90A

<400> SEQUENCE: 34
ccgtcagctg tgccgtcgcg cagcacgcgc cgccgtggac agaggactgc agaaaatcaa  60
cctatcctcc ttcaggacca acgtacagag                                   90

<210> SEQ ID NO 35
<211> LENGTH: 90
<212> TYPE: DNA
<213> ORGANISM: Artificial Sequence
<220> FEATURE:
<223> OTHER INFORMATION: F90G

<400> SEQUENCE: 35
ccgtcagctg tgccgtcgcg cagcacgcgc cgccgtggac agaggactgc agaaaatcaa  60
cctgtcctcc ttcaggacca acgtacagag                                   90

<210> SEQ ID NO 36
<211> LENGTH: 23
<212> TYPE: DNA
<213> ORGANISM: Artificial Sequence
<220> FEATURE:
<223> OTHER INFORMATION: F2forG

<400> SEQUENCE: 36
cccaataaaa gtgactctca gcg                                          23

<210> SEQ ID NO 37
<211> LENGTH: 23
<212> TYPE: DNA
<213> ORGANISM: Artificial Sequence
<220> FEATURE:
<223> OTHER INFORMATION: F2forA

<400> SEQUENCE: 37
cccaataaaa gtgactctca gca                                          23

<210> SEQ ID NO 38
<211> LENGTH: 20

```
<212> TYPE: DNA
<213> ORGANISM: Artificial Sequence
<220> FEATURE:
<223> OTHER INFORMATION: reverse Primer F2rev

<400> SEQUENCE: 38
ccagagagct gcccatgaat                                              20

<210> SEQ ID NO 39
<211> LENGTH: 18
<212> TYPE: DNA
<213> ORGANISM: Artificial Sequence
<220> FEATURE:
<223> OTHER INFORMATION: F5forG

<400> SEQUENCE: 39
cagatccctg gacaggcg                                                18

<210> SEQ ID NO 40
<211> LENGTH: 18
<212> TYPE: DNA
<213> ORGANISM: Artificial Sequence
<220> FEATURE:
<223> OTHER INFORMATION: F5forA

<400> SEQUENCE: 40
cagatccctg gacaggca                                                18

<210> SEQ ID NO 41
<211> LENGTH: 23
<212> TYPE: DNA
<213> ORGANISM: Artificial Sequence
<220> FEATURE:
<223> OTHER INFORMATION: reverse Primer F5rev

<400> SEQUENCE: 41
ggagacctaa catgttctag cca                                          23

<210> SEQ ID NO 42
<211> LENGTH: 30
<212> TYPE: DNA
<213> ORGANISM: Artificial Sequence
<220> FEATURE:
<223> OTHER INFORMATION: forward primer MSP SEPT9con Forw

<400> SEQUENCE: 42
gcgcgattcg ttgtttatta gttattatgt                                   30

<210> SEQ ID NO 43
<211> LENGTH: 31
<212> TYPE: DNA
<213> ORGANISM: Artificial Sequence
<220> FEATURE:
<223> OTHER INFORMATION: reverse Primers MSP SEPT9con Rev G

<400> SEQUENCE: 43
tcgaaatccg aaataatccc atccaactac g                                 31

<210> SEQ ID NO 44
<211> LENGTH: 31
<212> TYPE: DNA
<213> ORGANISM: Artificial Sequence
<220> FEATURE:
<223> OTHER INFORMATION: MSP SEPT9con Rev A

<400> SEQUENCE: 44
```
tcgaaatccg aaataatccc atccaactac a                                   31

<210> SEQ ID NO 45
<211> LENGTH: 85
<212> TYPE: DNA
<213> ORGANISM: Artificial Sequence
<220> FEATURE:
<223> OTHER INFORMATION: Temp Sept9 Methylated 5mC

<400> SEQUENCE: 45
ttcgcgcgat tcgttgttta ttagttatta tgtcggattt cgcggttaac gcgtagttgg    60
atgggattat ttcggatttc gaagg                                         85

<210> SEQ ID NO 46
<211> LENGTH: 85
<212> TYPE: DNA
<213> ORGANISM: Artificial Sequence
<220> FEATURE:
<223> OTHER INFORMATION: Sept9 unmethylated U

<400> SEQUENCE: 46
ttcgcgcgat tcgttgttta ttagttatta tgtcggattt cgcggttaac gugtagttgg    60
atgggattat ttcggatttc gaagg                                         85

<210> SEQ ID NO 47
<211> LENGTH: 20
<212> TYPE: DNA
<213> ORGANISM: Artificial Sequence
<220> FEATURE:
<223> OTHER INFORMATION: Primer P

<400> SEQUENCE: 47
cgttggtcct gaaggaggat                                               20

<210> SEQ ID NO 48
<211> LENGTH: 23
<212> TYPE: DNA
<213> ORGANISM: Artificial Sequence
<220> FEATURE:
<223> OTHER INFORMATION: Primer P+3

<400> SEQUENCE: 48
cgttggtcct gaaggaggat agg                                           23

<210> SEQ ID NO 49
<211> LENGTH: 26
<212> TYPE: DNA
<213> ORGANISM: Artificial Sequence
<220> FEATURE:
<223> OTHER INFORMATION: Primer P+6

<400> SEQUENCE: 49
cgttggtcct gaaggaggat aggttg                                        26

<210> SEQ ID NO 50
<211> LENGTH: 53
<212> TYPE: DNA
<213> ORGANISM: Artificial Sequence
<220> FEATURE:
<223> OTHER INFORMATION: F2forGlang

<400> SEQUENCE: 50
atccaactct ctacgcaatg gcactagaga cccaataaaa gtgactctca gcg            53